United States Patent [19]
Tallman et al.

[11] Patent Number: 5,964,700
[45] Date of Patent: *Oct. 12, 1999

[54] MEDICAL NETWORK MANAGEMENT ARTICLE OF MANUFACTURE

[75] Inventors: Joseph P. Tallman; Elizabeth M. Snowden, both of Boulder, Colo.; Barry W. Wolcott, Derwood, Md.

[73] Assignee: Access Health, Broomfield, Colo.

[*] Notice: This patent is subject to a terminal disclaimer.

[21] Appl. No.: 08/951,199

[22] Filed: Oct. 10, 1997

Related U.S. Application Data

[62] Division of application No. 08/562,003, Nov. 22, 1995, Pat. No. 5,764,923, which is a continuation of application No. 08/180,090, Jan. 10, 1994, Pat. No. 5,471,382.

[51] Int. Cl.⁶ .................................................. A61B 5/00
[52] U.S. Cl. ............................................. 600/300; 705/2
[58] Field of Search ........................... 364/400; 395/924; 600/300, 920, 923; 705/2, 3

[56] References Cited

U.S. PATENT DOCUMENTS

| | | |
|---|---|---|
| 4,130,881 | 12/1978 | Haessler et al. . |
| 4,290,114 | 9/1981 | Sinay ...................................... 364/900 |
| 4,489,387 | 12/1984 | Lamb et al. . |
| 4,838,275 | 6/1989 | Lee .......................................... 128/670 |
| 4,839,822 | 6/1989 | Dormond et al. . |
| 4,852,173 | 7/1989 | Bahl et al. .................................. 381/43 |
| 4,858,121 | 8/1989 | Barber et al. ............................. 364/406 |
| 4,872,122 | 10/1989 | Altschuler et al. ....................... 364/554 |
| 4,895,518 | 1/1990 | Arnold et al. ............................ 434/118 |
| 4,945,476 | 7/1990 | Bodick et al. ....................... 364/413.02 |
| 5,018,067 | 5/1991 | Mohlenbrock et al. ............ 364/413.02 |
| 5,025,374 | 6/1991 | Roizen et al. ...................... 364/413.02 |
| 5,065,315 | 11/1991 | Garcia . |
| 5,072,383 | 12/1991 | Brimm et al. ...................... 364/413.02 |
| 5,241,621 | 8/1993 | Smart ......................................... 395/51 |
| 5,253,164 | 10/1993 | Holloway et al. ....................... 364/406 |
| 5,255,187 | 10/1993 | Sorensen ............................ 364/413.02 |
| 5,263,123 | 11/1993 | Hayashi ..................................... 395/51 |
| 5,301,105 | 4/1994 | Cummings .............................. 364/401 |
| 5,307,262 | 4/1994 | Ertel .................................... 364/413.01 |
| 5,341,291 | 8/1994 | Roizen et al. ........................... 600/300 |
| 5,471,382 | 11/1995 | Tallman et al. ......................... 364/406 |
| 5,508,912 | 4/1996 | Schneiderman ..................... 364/401 R |

FOREIGN PATENT DOCUMENTS

| | | |
|---|---|---|
| WO A 94/07210 | 9/1992 | WIPO . |
| WO A 94/00817 | 6/1993 | WIPO . |

OTHER PUBLICATIONS

Chong–Yen Lee and Martha Evens, "Recommending Tests In A Multimembership Bayesian Diagnostic Expert System", May 12, 1991.

Broome, M.E., "Telephone Protocols for Pediatric Assessment and Advice", *Journal of Emergency Nursing*, vol. 12, No. 13, May/Jun. 1986, pp. 142–146.

(List continued on next page.)

*Primary Examiner*—Linda C. M. Dvorak
*Assistant Examiner*—Bryan K. Yarnell
*Attorney, Agent, or Firm*—Cooley Godward LLP

[57] ABSTRACT

In a medical network management system (NMS) (20), health plan beneficiaries access a team of health care professionals over the telephone to help them assess their health needs and select appropriate care. The NMS (20) is implemented with an article of manufacture for use with a data processing system (13). A storage medium (15) has stored therein a medical provider information stored program (22) and a medical provider database (24). The medical provider database describes clinical services or procedures available from each provider by clinical codes or procedure codes. The data processing system (13) is configured by the medical provider information stored program (22) when executed by the data processing system (13) to use the clinical codes or procedure codes to identify a medical provider from the medical provider database for providing a specific medical service to a patient.

7 Claims, 60 Drawing Sheets

OTHER PUBLICATIONS

Curry et al., "Telephone Assessment of Illness: What Is Being Taught and Learned?", *Pediatrics,* vol. 62, No. 4, Oct. 1978, pp. 603–605.

Kravitz et al., "Telephone in Diagnosis of Respiratory Diseases", *American Journal of Diseases of Children,* pp. 471–472.

Oberklaid et al., "Paediatric Telephone Consultation—A Neglected Area of Health Service Delivery", *Aust. Peadiatrics,* vol. 20, 1984, pp. 113–114.

Fosarelli, P.D., "The Telephone in Pediatric Medicine", *Clinical Pediatrics,* vol. 22, No. 4, Apr. 1983, pp. 293–296.

Mapes et al., "Feasibility Study of a Pediatric Telephone Consultation Service", *Pediatrics,* vol. 50, No. 2, Aug. 1972, pp. 307–311.

Nickerson et al., "How Dependable is Diagnosis and Management of Earache by Telephone", *Clinical Pediatrics,* vol. 14, No. 10, Oct. 1975, pp. 920–023.

Wood, P.R., "Pediatric Resident Training in Telephone Management: A Survey of Training Programs in the United States", *Pediatrics,* vol. 77, No. 6, Jun. 1986, pp. 822–825.

Katz, H.P., "A Schema for Improving Efficiency in an Ambulatory Care Setting", *Clinical Pediatrics,* vol. 14, No. 7, Jul. 1975, pp. 658–661.

Knowles et al., "ED Medical Advice Telephone Calls: Who Calls and Why?", *Journal of Emergency Nursing,* vol. 10, No. 6, Nov./Dec. 1984, pp. 283–286.

Smith et al., "Patient Management by Telephone: A Training Exercise for Medical Students", *Journal of Family Practice,* vol. 10, No. 3, 1980, pp. 463–466.

Levy et al., "Development and Field Testing of Protocols for the Management of Pediatric Telephone Calls: Protocols for Pediatric Telephone Calls", *Pediatrics,* vol. 64, No. 5, Nov. 1979, pp. 558–563.

Tripp, S., "Telephone Techniques in Pediatric Practice", *American Journal of Nursing,* vol. 71, No. 9, Sep. 1971, pp. 1722–1724.

Geller et al., "American Poison Control Centers: Still Not All the Same?", *Annals of Emergency Medicine,* vol. 17, No. 6, Jun. 1988, pp. 559–603.

Trautlein et al., "Malpractice in the Emergency Department—Review of 2000 Cases", *Annals of Emergency Medicine,* vol. 13, No. 9, Sep. 1987, pp. 709–710.

Thompson et al., "Evaluation of Regional and Nonregional Poison Centers", *the New England Journal of Medicine,* vol. 306, No. 4, Jan. 27, 1981, pp. 191–194.

Dunn, J.M., "Warning: Giving Telephone Advice is Hazardous to Your Professional Health", *Nursing85,* Aug., pp. 40–41.

Dunn et al., "Using Simulated Patients to Teach Family Practice Residents to Manage Patients by Telephone", *Journal of Medical Education,* vol. 62, Jun. 1987, pp. 524–526.

Dickinson et al., "Pediatric House Staff Communication Skills: Assessment and Intervention", *Journal of Medical Education,* vol. 58, Aug. 1983, pp. 659–662.

Evens et al., "Using Patient–Simulators to Teach Telephone Communication Skills to Health Professionals", *Journal of Medical Education,* vol. 58, Nov. 1983, pp. 894–898.

Pope et al., "Determinants of Medical Care Utilization: The Use of Telephone for Reporting Symptoms", *Journal of Health and Social Behavior,* vol. 12, No. 2, Jun. 1971, pp. 155–162.

Strain et al., "The Preparation, Utilization, and Evaluation of a Registered Nurse Trained to Give Telephone Advice in a Private Pediatric Office", *Pediatrics,* vol. 47, No. 6, Jun. 1971, pp. 1051–1055.

Komaroff et al., "Protocols/Clinical Algorithm in Ambulatory Medical Care", papter presented in Boston, MA, approximately 1977/1978.

Heagarty et al., "Use of the Telephone by Low–income Families", *Journal of Pediatrics,* vol. 73, No. 5, pp. 740–744.

Wang et al., "Use of the Telephone in a Health Maintenance Service for the Chronically Ill: A Preliminary Report", *J. Chron Dis,* vol. 24, 1971, pp. 489–494.

Greenlick et al., "Comparing the Use of Medical Care Services by a Medically Indigent and a General Membership Population in a Comprehensive Prepaid Group Practice Program", *Medical Care,* vol. X, No. 3, May–Jun. 1972, pp. 187–200.

Shah et al., "An Expanded Emergency Service: Role of Telephone Services in the Emergency Department", *Ann Emerg Med,* vol. 9, No. 12, Dec. 1980, pp. 617–623.

Greenlick et al., "Determinants of Medical Care Utilization: The Role of the Telephone in Total Medical Care", *Medical Care,* vol. XI, No. 2, Mar.–Apr. 1973, pp. 121–134.

Ott et al., "Patient Managment by Telephone by Child Health Associates and Pediatric House Officers", *Journal of Medical Education,* vol. 49, Jun. 1974, pp. 596–600.

Fosarelli, P.D., "The Emphasis of Telephone Medicine in Pediatric Training Programs", *AJDC,* vol. 139, Jun. 1985, pp. 555–557.

Wood et al., "Telephone Management Curriculum for Pediatric Interns: A Controlled Trial", *Pediatrics,* vol. 83, No. 6, Jun. 1989, pp. 925–930.

ESI, Eligibility Services, Inc., brochure.

Wilson et al., "Pediatric Algorithm–Directed Triage" A Prospective Study.

Poole et al., "After–Hours Telelphone Coverage: The Application of an Aera–Wide Telephone Triage and Advice System for Pediatric Practices", *Oregon Health Forum,* vol. 6, Aug. 1992.

Wilson et al., "Pediatric Physician Extenders in a Walk–in Clinic: Algorithm–Directed Triage—The Beginning".

Perrin et al., "Telephone Management of Acute Pediatric Illness", *The New England Journal of Medicine,* vol. 298, No. 3, Jan. 19, 1978, pp. 130–135.

Verdile et al., "Emergency Department Telephone Advice", *Annals of Emergency Medicine,* vol. 18, No. 3, Mar. 1989, pp. 278–282.

Greitzer et al., "Telephone Assessment of Illness by practicing Pediatricians", *Journal of Pediatrics,* vol. 88, No. 5, May 1976, pp. 880–882.

Isaacman et al., "Pediatric Telephone Advice in the Emergency Department: Results of a Mock Scenario", *Pediatrics,* vol. 89, No. 1, Jan. 1992, pp. 35–39.

Strasser et al., "Controlled Clinical Trial of Pediatric Telephone Protocols", *Pediatrics,* vol. 64, No. 5, Nov. 1979, pp. 553–557.

Katz et al., "Quality Assessment of Telephone Care System Utilizing Non–Physician Personnel", *AJPH,* vol. 68, No. 1, Jan. 1978, pp. 31–38.

Selbst et al., "The Telephone in Pediatric Emergency Medicine", *Pediatric Emergency Care,* vol. 1, No. 2, Jun. 1985, pp. 108–110.

Vaughn et al., "Effective Algorithm–Based Triage and Self–Care Protocols: Quality Medicine at Lower Costs", *Annals of Emergency Medicine,* vol. 9, No. 1, Jan. 1980, pp. 32–36.

Wood et al., "An Efficient Strategy for Managing Acute Respiratory Illness in Adults", *Annals of Internal Medicine,* vol. 93, 1980, pp. 757–763.

Wolcott, B.W., "Basic Decisions in Emergency Department Cases: A Logical Approach", *JACEP,* vol. 7, No. 4, Apr. 1978, pp. 149–151.

Wolcott, G.W., "Editorials—For Whom the (Phone) Bell Tolls", Mar. 1989.

Wolcott, B.W., "Refining Criteria for X–Ray Utilization as a Result of a Patient Care Evaluation Study", *Quality Review Bulletin,* Jul. 1980.

Wolcott et al., "The Use of In–Barracks Screeners to Improve Military Sick Call", *Military Medicine,* Feb. 1979, pp. 99–102.

Wolcott, B.W., "What is an Emergency? Depends on Whom You Ask", *JACEP,* Jun. 1979 (Reprint).

Deriet et al., Keeping Non–urgent Patients Out of the Emergency Department: Would it Make a Difference? *Academic Forum.*

Albin et al., "Evaluation of Emergency Room Triage Performed by Nurses", *AJPH,* vol. 65, No. 10, Oct. 1975, pp. 1063–1068.

Levy et al., "Development and Field Testing of Protocols for the Management of Pediatric Telephone Calls: Protocols for Pediatric Telephone Calls", *Pediatrics,* vol. 64, No. 5, Nov. 1979, pp. 558–563.

Rivara et al., "Pediatric Nurse Triage", *AJDC,* vol. 140, Mar. 1986, pp. 205–210.

Berman, D.A., "Computerized Algorithm–Directed Triage in the Emergency Department", *Annals of Emergency Medicine,* vol. 18, No. 2, Feb. 1989, pp. 141–144.

George et al., "Differences in Priorities Assigned to Patients by Triage Nurses and by Consultant Physicians in Accident and Emergency Departments", *Journal of Epidemology and Community Health,* vol. 47, 1993, pp. 312–315.

Wilson et al., "Computerized Triage of Pediatric Patients: Automated Triage Algorithms", *Annals of Emergency Medicine,* vol. 10, No. 12, Dec. 1981, pp. 636–640.

"Algorithm–Directed Troop Medical Care", *Ambulatory Patient Care,* U.S. Army Health Services Command, Jun. 1985, pp. 5–22.

"Triage Aidman's Manual", Hq. U.S. Army Health Services Command, Jan. 1979.

"Adult Triage Manual", Department of Medicine, Brooke Army Medical Center, Jun. 1979.

"Pediatric Triage Manual", Department of Pediatrics, Brooke Army Medical Center, Jun. 1979.

Student Handout—Algorithm Protocols—Reference Material For Use In The Following Courses: Operational & Emergency Medicine ($4^{th}$ Year).

Burger et al., "Physician Extenders in the Delivery of Non–Appointed Ambulatory Medical Care in the Military", *Military Medicine,* vol. 141, No. 5, May 1977.

Phillips, D.F., "Protocols For Patient Care", *Hospitals, J.A.H.A.,* vol. 49, Mar. 1, 1975.

"Summary of Ambulatory Patient Care Research Involving Physician Extenders (AMOSIST's) at Brooke Army Medical Center", 1975.

| IAS Nursetool – Call Type Selection |||||
|---|---|---|---|---|
| Emergency (F6) | Illness Care (F7) | Provider Selections (F8) | Information (F9) | Other (F10) |

Caller

| IAS Nursetool – Emergency Handling |
|---|

Caller Name: [          ]

Caller Phone: [          ]

Assessment of Situation:

[                              ]

[ OK ]                    [ Cancel ]

FIG. 11

IAS Nursetool – Eligibility Verification

Patient Last Name: Johnson

Patient First Name: Robert

Health Plan:

Health Plan ID:

Social Security Number:

Sponsor's Employer

Patient Zip Code:

Patient Phone:

Check Eligibility (ESC-F11)

Results:

OK    New Patient

FIG. 12

IAS Nursetool - New Patient Data Entry

| | | |
|---|---|---|
| Last Name: | Johnson | Patient's SSN: | 333-22-1111 |
| First Name, MI: | Robert | Sponsor's Employer: | State of Colorado |
| Street Address: | 3423 W. 44th Avenue | Client: | State of Colorado |
| City, State: | Boulder, CO | Plan Name: | Kaiser |
| Zip Code: | 80301 | Plan Type: | Standard |
| Phone: | (303)-443-4600 | Health Plan ID: | 90611 |
| Date Of Birth: | 02-may-1938 | Primary Physician: | Dr. Hillary Kruse |
| Gender: | Male | | |
| Ethnic Origin: | White | | |
| Marital Status: | Widowed | | |

OK  Cancel

FIG. 13

```
┌─────────────────────────────────────────┐
│      IAS Nursetool - Patient Chart      │
├─────────────────────────────────────────┤
│  Name:            Robert Johnson        │
│  Address:         3423 W. 44th Avenue   │
│                   Boulder, CO           │
│  Zip:             80301                 │
│  Home Phone:      (303)-443-4600        │
│  SSN:             333-22-1111           │
│  Employer:        State of Colorado     │
│  Health Plan:     Kaiser                │
│  Plan Type:       Standard              │
│  Subscriber Number: 333221111           │
│                                         │
│  [Identifying Information] [Demographic Information] │
│  [Health Information]      [Prior IAS Contacts]      │
└─────────────────────────────────────────┘
```

FIG. 14

```
┌─────────────────────────────────────────┐
│      IAS Nursetool - Patient Chart      │
├─────────────────────────────────────────┤
│  No health history found for this patient │
│                                         │
│                                         │
│  [Identifying Information] [Demographic Information] │
│  [Health Information]      [Prior IAS Contacts]      │
└─────────────────────────────────────────┘
```

FIG. 17

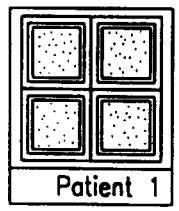
Patient 1

FIG. 18

```
IAS Nursetool  -  Algorithm Section
```

| Topical Listing | Alphabetical Listing |
|---|---|
| Cardiorespiratory | Pediatric Abdominal Pain |
| Constitutional | Pediatric Abnormal Growth Developn |
| Dermatologic | Pediatric Acne |
| Ear-Nose-Throat | Pediatric Asthma |
| Eye-Visual | Pediatric Athletes Foot |
| Gastrointestinal | Pediatric Back Pain |
| Genitourinary | Pediatric Bites Animal |
| Gynecological | Pediatric Bites Human |
| Musculoskeletal | Pediatric Bites Insect |
| Neuropsychiatric | Pediatric Bites Snake |
| Miscellaneous | Pediatric Boils |
|  | Pediatric Burn |
|  | Pediatric Chest Pain |
|  | Pediatric Circumcision Problems |
|  | Pediatric Constipation |

Selected Algorithm: [          ]      Select

Keywords: [          ]

Purpose of Selected Algorithm:
[                              ]

Associated Algorithms:
[                              ]

AS Nursetool – Algorithm Navigation

Algorithm Name: Pediatric Headache New

Clinical Question:
Has there been head trauma in the past 72 hours?

Lay Question:
In the past three days, has the child had a serious blow to the head...like a car accident or a bad fall?

Rationale:
Intra-cranial bleeding can be delayed; especially in children, the symptons of the intra-cranial bleeding can be temporally distant from the head injury. The "trauma" here is more than simply "bumping the head", but need not have "knocked out the child" for a long time.

[ YES ]  [ NO ]  [ UNSURE ]  [ BACK ]

Comments:

[ Insert ]
[ Erase ]

FIG. 22

AS Nursetool – Nurse Action List

SPEAK TO IAS PROVIDER

[Select]

Clinical Rationale:
Stiff neck, fever, and headache suggest meningitis. The IAS Provider will determine if it will be necessary to activate Emergency Procedures.

Message to Patient:
Because the child appears to have a stiff neck, we want you to speak now to our physician. If you will stay on the line, we will connect you as quickly as possible.

Symptom Pattern:
Fever and stiff neck in a child with a headache>

Need to Consider:
Meningitis

Provider Codes:

[Done]  [Cancel]

FIG. 24

| Action in Nurse Action List Window | Effect of Clicking the Select Button |
|---|---|
| Acivate Emergency Procedures | Opens Emergency Handing window |
| Speak To IAS Provider | Opens Speak With IAS Provider window |
| Urgent Care | Not implemented, but is logged as recommended |
| Transfer to Algorithm | Opens Algorithm Navigation window |
| Speak To Provider-Sorting | Open Speak With Provider window |
| Speak To Provider-Treatment | Open Speak With Provider window |
| Early Illness Appointment | Not implemented, but is logged as recommended |
| Routine Illness Appointment | Not implemented, but logged as recommended |
| Self Care | Open Self Care Endpoint window |

FIG. 25

IAS Nursetool-Self Care End Point

Instructions:

PEDIATRIC CONSTIPATON SELF CARE INSTRUCTIONS

SELF-CARE PROTOCOL : PEDIATRIC CONSTRUCTION

General Information to reassure:
- we understand your concern about the constipation
- be assured that this is common in children and there's no indication of a serious underlying problem
- many children routinely go three or four days between bowel movements; this is normal
- a "change" in bowel habits happens occasionally to almost every child:
- routine use of laxatives or enemas in children is not necessary(and may be harmful)
- a diet with adequate fiber and "bulk" is recommended.

Instruction for Sympton/Pain relief:
- Give more fluids, i.e. juices, Kool-Aid, water;
- Prune juice, an old "favorite", is effective;
- Add more "bulk"-include a level teaspoon of bran in daily food for child one year or older; add up to 3 tablespoonful of bran to food for children 8 years or older;
- Avoid getting too "worried" about child's bowel habits;
- Unless specifically recommended by a medical provider, do not use laxatives, rectal suppositories, or enemas; they may interfere with child's ability to reestablish regular bowel habits;
- We can arrange to call you back in a few days, if that would help.

Does patient accept?   ◆ YES    ◇ NO

Callback Date: [    ]         Callback Time: [    ]

End Point Disposition:

[                                        ]

[ OK ]                                              [ Cancel ]

FIG. 26

| IAS Nursetool – Speak With IAS Provider |

Provider Name: Dr. Emmet Frehl

Provider Comments:
Asthmatic child with complaint of "unable to handle secretions.

Cannot rule out acute asthmatic episode.

Recommendation: Emergency Handling

Does patient accept?   ◆ YES   ◇ NO

[ OK ]                              [ Cancel ]

IAS Nursetool – Speak With Provider

Provider Name: [_____]

Does Patient Accept?   ◆ Yes     ◇ No

[ OK ]                              [ Cancel ]

FIG. 29

IAS Nursetool – Information Type Selection

◆ Medical Information

◇ Health Plan Rules

[ OK ]                              [ Cancel ]

FIG. 30

IAS Nursetool – Self Care Selection

| Topical Listing | Alphabetical Listing |
|---|---|
| Cardiorespiratory | Adult Musculoskeletal Back Pain |
| Constitutional | Adult Sciatica |
| Dermatologic | Adult Traumatic Back Pain |
| Ear-Nose-Throat | Pediatric Abdominal Pain |
| Eye-Visual | Pediatric Black Widow/Brown Recluse: |
| Gastrointestinal | Pediatric Asthma (Resolved) |
| Genitourinary | Pediatric Asthma (Medication) |
| Gynecological | Pediatric Constipation |
| Musculoskeletal | Pediatric Analgesia |
| Neuropsychiatric | Pediatric Birthmarks |
| Miscellaneous | Pediatric Avulsed Tooth |
| | Pediatric Acute Bleeding |
| | Pediatric Cough |
| | Pediatric Ear Pain |
| | Pediatric Fever |

Selected: [_____]

Keywords: [_____]     [ Select ]

| IAS Nursetool – Call Termination |

Termination: ◆ Normal  ◇ Abnormal

What would this patient have done if this service were not available?

◇ Sought emergency care

◇ Made appointment with physician

◇ Attempted self care

◆ Other:

[                                                                 ]

Tag for rapid retrieval?  ◆ Yes  ◇ No

Indicate Reason:

☐ This call involved a potential life-saving intervention

☐ This call involved a potential saving of medical costs

☐ This call was a noteworthy example of service value

☐ This was a problematic call – may require follow-up

Comments:

[                                                                 ]

| Done |

FIG. 35

| IAS Nursetool – Problem Notebook |

Select By: [User ▽]    Select Key: [Triage User ▽]

```
PN=224:23-aug-1993 - Triage User - Selected pad abdominal plan, blew up ...
PN=158:06-aug-1993 - Triage User - When I enter a new patient record with
                                    only SSN...
PN=148:06-aug-1993 - Triage User - Swallowing spelled wrong in Algorithm
                                    Navigation...
```

Problem Type: [System Problem ▽]    Priority: [Medium ▽]

When I enter a new patient with only SSN and client filled in, everything works fine. However, the next time I do eligibilty verfication, TWO records for this new patient appear in the eligibilty results list. NOTE: I can't get this to repeat every time (intermittent) – John Brinegar Status: [Resolved ▽]    Resolved By: [John Brinegar ▽]

This was found a long time ago by Gad. jov – NO DEFECT FOUND – 06/31/93

[Clear]    [Insert]    [Update]

[OK]                   [Cancel]

FIG. 36

| IAS Nursetool - Work List |

Select By: [Today's date ▽]   Select Key: [04-sep-1993 ▽]

```
04-sep-1993 09:00:00 - Liz Snowden - Chris Dugan - (303)689-4734
04-sep-1993 12:30:00 - Liz Snowden - Wing Nutt - (303) 689-0613
04-sep-1993 20:00:00 - Joe Tailman - Betty Boyer - (909) 485-7632
04-sep-1993 21:00:00 - Liz Snowden - Alson Smith - (303) 499-4505
```

[ Creater New Callback ]

Assigned To:        Liz Snowden
Status:             Incomplete
Last Attempt:       04-sep-1993 12:37:54
Number of Attempts: 2

[ OK ]   [ Update ]   [ Perform ]   [ Cancel ]

FIG. 37

| IAS Nursetool – Callback Scheduling | | | |
|---|---|---|---|
| Callback Date: | 23-oct-1993 | Callback Time: | 19:30 |
| Caller Name: | Denise Coulter | Caller Name: | (303)993-1010 |
| Responsible for Callback: | | Triage User ▽ | |

Callback Comments:

OK | Cancel

FIG. 38

IAS Nursetool – Perform Callback

Caller Name: Jennifer Bially  Caller Phone: (303)-883-8743

Last Attempt:  Attempts: 0

Call Summary:

```
CALL START:       29-dec-1993  13:25:25
CALL END:         29-dec-1993  13:28:25
NURSE:            Mary Bulick
CALL ID:          2079
STATUS:           Active
PATIENT'S PROBLEM/NURSE ASSESSMENT:

CALL TYPE:        Illness Care Call
```

[ Display Patient Chart ]   [ Display Self Care Instructions ]

Call Result:  ◆ Success   ◇ Failure

Next Attempt Date: 29-dec-1993  Next Attempt Time: 14:00:00

Purpose/Resolution:

Check status of patient

[ OK ]   [ Continue ]   [ Cancel ]

FIG. 39

```
┌─────────────────────────────────────────────────────────┐
│ ▒▒▒▒▒▒▒▒▒ IAS Nursetool - Callback Update ▒▒▒▒▒▒▒▒▒ │
│                                                         │
│  Caller Name:  [Chris Dugan]  Caller Phone: [(303)-889-4734] │
│                                                         │
│  Last Attempt: [        ]     Attempts:     [0        ] │
│                                                         │
│  Call Summary:                                          │
│  ┌───────────────────────────────────────────────┐▲    │
│  │ CALL START:      04-SEP-1993 12:49:04         │     │
│  │ CALL END:        04-SEP-1993 12:53:29         │     │
│  │ NURSE:           Liz Snowden                  │     │
│  │ CALL ID:         1567                         │     │
│  │ STATUS:          Active                       │     │
│  │ PATIENT'S REQUEST:                            │     │
│  │ CALL TYPE:       Illness Care                 │     │
│  │ AUXILLIARY INFO:                              │▼    │
│  └───────────────────────────────────────────────┘     │
│                                                         │
│   [ Display Patient Chart ]  [ Display Self Care Instructions ] │
│                                                         │
│  Assigned To:    [Liz Snowden ▼]  Assigned To:   [Incomplete ▼] │
│  Next Attempt Date: [04-sep-1993]  Next Attempt Date: [09:00:00] │
│                                                         │
│  Resolution:                                            │
│  ┌───────────────────────────────────────────────┐     │
│  │                                               │     │
│  └───────────────────────────────────────────────┘     │
│                                                         │
│  [   OK   ]                              [  Cancel  ]   │
└─────────────────────────────────────────────────────────┘
```

FIG. 41

```
┌────────────────────────────────────────────┐
│ ▒ IAS Nursetool - Information Type Selection ▒ │
│                                            │
│   ◆ Medical Information                    │
│                                            │
│   ◇ Health Plan Rules                      │
│                                            │
│   [   OK   ]                  [  Cancel  ] │
└────────────────────────────────────────────┘
```

FIG. 42

| IAS Nuretool – Provider Criteria |

| Criteria Type | CODES | |
|---|---|---|
| Provider Type | GEND | Provider's gender is <list> |
| Personal | UAGE | Provider is younger than <integer> |
| Credentials | OAGE | Provider is older than <integer> |
| Office Information | MARS | Provider's martial status is <list> |
| Office Policy | ETHOS | Provider's ethnic background <list> |
| Patient Type | RELIG | Provider's religion <list> |
| Payment | FNAME | Provider's first name <string> |
| Health Plan | LNAME | Provider's last name <string> |
| Special Dental | | |
| Special Mental Health | | |
| Special Facility | | |
| Clinical Codes | | |
| Procedural Codes | | |

Selected Criterion: GEND :Provider's gender is    [Insert]

Value: Female    [Delete]

Criteria List:

| AGEN | Accepts patient gender:Female |
| AAGE | Accepts patient of age:2 |
| PHYS | Provider is a physican |
| GEND | Provider's gender is:Female |

Providers Matched(ESC-s)    3

[Display]    [Comments]    [Cancel]

FIG. 47

| IAS Nursetool - Provider Search Results |
|---|
| Churchill,Edmund - Physician - Denver,CO,80220 |
| Downey,Rebecca - Physician - Aurora,CO,20013 |
| Bronson,Richard - Physician - Denver,CO,80236 |
| Bein,Jennifer - Phsician - Denver,CO,80222 |
| Briley,LaToya - Physician - Boulder,CO,80302 |
| Fincher,Roger - Physician - Denver,CO,80239 |
| Aboud,Rajami - Physician - Boulder,CO,80301 |
| ,Boulder Medical Ctr - Facility - Boulder,CO,80302 |
| Rhodes,Jonathan - Mental Health - Denver,CO,80212 |
| Haller-Grant,Diane R. - Mental Health - Denver,CO,80212 |
| Lucero,Elizabeth - Physician - Littleton,CO,80120 |

| | |
|---|---|
| Address: | 200 S.Jackson #404 |
| City,State: | Denver, CO |
| Specialty: | Family Practice |
| Years in Practice: | 21 |
| Age: | 49 |
| Gender: | Male |

[ OK ]  [ Referral ]  [ View Bio ]  [ Own Provider ]  [ Cancel ]

FIG. 48

| | IAS Nursetool – Provider Biography | |
|---|---|---|
| Name: | Edmund Churchill | |
| Building Name: | Jackson Medical Building | |
| Address: | 200 S. Jackson #404 | |
| Office Phone: | (303) 940 – 1234 | |
| Scheduling Phone: | (303) 940 – 1235 | |
| After Hours: | (303) 940 – 1236 | |
| FAX Number: | (303) 940 – 1237 | |
| TDD Number: | () – | |
| Undergrad: | University of Denver – Denver, CO | |
| Medical School: | University of Utah – Ogden, UT | |

Residencies:
    Univ. of Colorado – Denver, CO
Postgrad Training:

Licensure

| General Info./Credentials | Characteristics |
| Office Information | Payment Policies |
| Clinical Information | Procedural Information |
| Appointment | Referral | Cancel |

FIG. 49

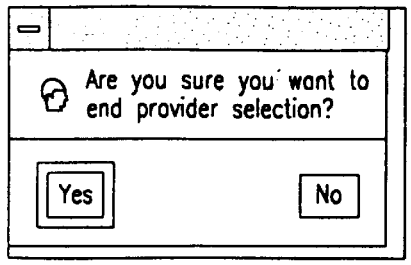

FIG. 55

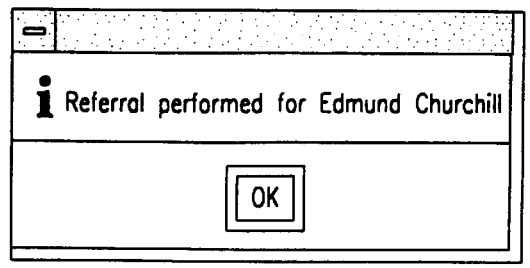

FIG. 57

```
┌─────────────────────────────────────────────────────────────┐
│ □         IAS Nursetool - Provider Biography                │
├─────────────────────────────────────────────────────────────┤
│  Gender:              Male                                ▲ │
│  Age:                 31                                    │
│  Marital Status:      Married                               │
│  Years in Practice:   5                                     │
│  Ethnic Origin:       Asian                                 │
│  Religion:            Buddhist                              │
│  Religion relevant:   No                                    │
│                                                             │
│  Presdriptions:                                             │
│        Prescribes refills over the phone during office      │
│  hours for established patients - Yes                       │
│        Prescribes refills over the phone during office      │
│  hours for new patients - No                                │
│        Prescribes new orders over the phone during office   │
│  hours for established patients - No                        │
│        Prescribes new order over the phone during office    │
│  hours for new patients - No                                │
│        Prescribes refills over the phone after office       │
│  hours for established patients - Yes                       │
│        Prescribes refills over the phone after office       │
│  hours for new patients - No                              ▼ │
└─────────────────────────────────────────────────────────────┘
```

| General Info./Credentials | Characteristics |
| Office Information | Payment Policies |
| Clinical Information | Procedural Information |
| Appointment | Referral | Cancel |

FIG. 56

Header Parameter

| ALGORITHM NAME | : | |
| PURPOSE | : | |
| CATEGORY | : | |
| RELATED ALGRMS | : | |
| KEYWORDS | : | |

FIG. 65

Yes / No Question Parameters

| CLINICAL QUESTION: | |
| CLINICAL RATIONALE: | |
| LAY QUESTION(S): | |
| INSTRUCT NOT SURE: | |
| AUXILLARY2: | |

| End Point Parameters |
|---|
| RECOMMENDATION: |
| CLINICAL RATIONALE: |
| MESSAGE TO PATIENT: |
| SYMPTOM PATTERN: |
| NEED TO CONSIDER: |
| PROVIDER CODES: |
| DATA: |

FIG. 69

New File

Please Enter File Name:

ADULT_BACK_PAIN

[NEW FILE]  [CANCEL]

FIG. 70

| | Yes/No Question Parameters |
|---|---|
| CLINICAL QUESTION: | Did the pain follow a direct blow or an acceleration/deceleration injury ? |
| CLINICAL RATIONALE: | These types of injuries can damage the spine itself, possibly compromising the spinal cord or peripheral nerve roots. |
| LAY QUESTION(s): | Did you get "hit" on the bones of your back ? Did you fall "off" something higher than your head ? Did this happen in a motor vehicle accident ? How did the injury happen ? |
| INSTRUCT NOT SURE: | Treat as a "NO" response. |
| AUXILLARY2: | ^ |

FIG. 74

| | End Point Parameters |
|---|---|
| RECOMMENDATION: | SPEAK TO IAS PROVIDER |
| CLINICAL RATIONALE: | The patient's apparent new motor deficit indicates possible damage to the cord or peripheral nerve roots, and the IAS provider evaluation will determine if an emergency response is indicated. |
| MESSAGE TO PATIENT: | Because you have had an injury and now some muscles may not be working correctly, we think it would be best if you spoke with our physician now. If you'll stay on the line, we'll |
| SYMPTOM PATTERN: | Adult with back injury and new motor deficit. |
| NEED TO CONSIDER: | Cord compression<br>Nerve root damage |
| PROVIDER CODES: | 805-809,3;950-957,3;<br>Fracture-Neck and Trunk<br>Nerve and Spinal Cord Injury-General |
| DATA: | ^ |

FIG. 75

| | Action Parameters |
|---|---|
| RECOMMENDED ACTION: | ACCESS SELF-CARE INSTRUCTIONS |
| CLINICAL RATIONALE: | This patient has post-traumatic back pain without indications of serious injury. A simple musculoskeletal injury is most likley, and those will respond to self-care instructions. |
| SYMPTOM PATTERN: | Post-traumatic back pain without any high-risk indicators in an adult. |
| NEED TO CONSIDER: | N/A |
| PROVIDER CODES: | GS-205.2; Primary Care-Adult Musculoskeletal |
| DATA: | Adult Traumatic Back Pain |
| MESSAGE TO PATIENT: | Your answers to our questions indicate that it is highly unlikely that you have a condition that would benefit from an appointment with a physician. We'd like to offer you some |

FIG. 76

| | Transfer Parameters |
|---|---|
| TRANSFER TO: | Transfer to PEDIATRIC BACK PAIN algorithm |
| CLINICAL RATIONAL: | |
| SYMPTOM PATTERN: | |
| DEST. ALGORITHM: | PEDIATRIC_BACK_PAIN |
| DESTINATION NODE: | |
| AUX1: | |

FIG. 77

Algorithm Summary:

Algorithm Name:   ADULT BACK PAIN

Purpose:   Sort adult patients with low back pain

Algorithm "Road Map":   Total Questions:   36      Stern Questions:   19

Loops:  Trauma:  6   Aneurysm:  4   Fever:  3   Abdominal Pain:  1   Chronic:  1

Anticipated Call Distribution:   SELF CARE:  58%

| | |
|---|---|
| Activate Emergency Procedures: | 0% |
| Urgent Care: | 2% |
| Speak to IAS Provider: | 10% |
| Speak to Provider-Sorting: | 0% |
| Speak to Provider-Treatment: | 0% |
| Early Illness Appointment: | 10% |
| Routine Illness Appointment: | 15% |

FIG. 78

MEDICAL NETWORK MANAGEMENT ARTICLE OF MANUFACTURE

CROSS REFERENCE TO RELATED APPLICATIONS

This application is a division of U.S. application Ser. No. 08/562,003, filed Nov. 22, 1995, now U.S. Pat. No. 5,764,923; which is a continuation of U.S. application Ser. No. 08/180,090, filed Jan. 10, 1994, now U.S. Pat. No. 5,471,382.

BACKGROUND OF THE INVENTION

1. Field of the Invention

The present invention relates generally to a system and process for managing health care and addressing many of the problems faced by those involved with health care today; payers, patients, and providers. More particularly, it relates to such a system and process which interfaces with health plan beneficiaries who have decided to seek health care services from a doctor and/or some other type of health care provider. These calls are answered by nurses and/or other types of health care professionals, who use the proprietary information tools and processes of the network management system (NMS) to help patients assess their health needs and then select appropriate care.

2. Description of the Prior Art

Using conventional approaches to access the health care system, many individuals with self-correcting conditions will see a doctor and begin to receive care that in most cases will not have medical benefit Many will also receive treatment from a provider who is not the most qualified to treat their particular condition. For such reasons, there has been an effort to develop alternative approaches.

Consumer Health Services currently operates a telephone-based, hospital and doctor marketing and referral service under the brand name of Prologue. Consumer Health collects information about doctors and makes patient referrals to doctors.

Other approaches have been suggested in the prior art For example, U.S. Pat. No. 4,852,173, issued Jul. 25, 1989 to Bahl et al. discloses the use of branched tree logic, primarily for a speech recognition system. However, the teaching of this patent also suggests application of branched tree logic for medical applications as follows: "While the invention will most often refer to speech recognition and specifically to next word prediction, the described invention is equally applicable to any pattern recognition system in which a next event or next data predictor is based upon a past event or given set of data. For example, given a list of a patient's medical symptoms, what is the best course of treatment or what is the best diagnosis." (Column 1, lines 60–69). However, the system and process there disclosed imposes the limitation that all nodes in the branched tree logic be related to each other in terms of probability or be probabilistically dependent on each other. It is believed that such a limitation is not appropriate for an effective medical network management system and process, because numerical data to establish the dependencies is not available. There is therefore a need for patient screening system and process in which the branched chain logic does not require nodes that are related probabilistically or probabilistically dependent on one another.

U.S. Pat. No. 4,838,275, issued Jun. 13, 1989 to Lee and U.S. Pat. No. 4,290,114, issued Sep. 15, 1981 to Sinay both disclose systems and processes including patient screening by non-physicians, but without the use of branched chain logic for such screening.

A variety of approaches are also known in the art for systems and processes that automate medical diagnosis. For example, U.S. Pat. No. 5,263,123 discloses an expert system using a form of fuzzy logic for medical diagnosis. However, it should be recognized that diagnosis is a different problem than managing access to medical providers who can then make a diagnosis and institute effective treatment.

Accordingly, the art relating to patient screening and provider referral is fairly well developed. However, a need remains for further development of such systems and processes, especially in light of current movement to a universal care medical system.

SUMMARY OF THE INVENTION

Accordingly, it is an object of this invention to provide a medical network management system and process system based on understanding and managing the process of care, in an integrated manner, from the onset of patient perception of possible needs.

It is a further object of the invention to provide such a medical network management system and process which allows beneficiaries to obtain appropriate care, at the appropriate time, from an appropriate provider.

It is still another object of the invention to provide such a medical network management system and process which effectively reduces utilization and costs, while increasing user satisfaction and overall quality of care.

It is a still further object of the invention to provide such a medical network management system and process which uses unique information systems to help guide patients through and manage the process of care, thereby assuring quality health care.

The attainment of these and related objects may be achieved through use of the novel medical network management system herein disclosed. A medical network management system in accordance with this invention has a data processing system including a memory containing a patient assessment stored program and a patient database, a display, and input means. The patient assessment stored program includes means for checking patient eligibility, means for selecting a branched chain logic algorithm for assessing a patient for an appropriate timing and type of medical care, and a plurality of branched chain logic algorithms. Each of the branched chain logic algorithms assess the patient for an appropriate timing and level of medical care. The data processing system is configured by the patient assessment stored program to present a series of questions on the display for checking patient eligibility to receive medical care, for selecting one of the plurality of branched chain algorithms, and for guiding the patient through the selected one of the plurality of branched chain algorithms, to enter answers from the patient to the series of questions, and to make a medical care timing and level of medical care recommendation in response to patient answers to the questions, and to provide the medical care timing and level of medical care recommendation on the display.

In another aspect of the invention, a data processing system including a display utilizes a process for managing health care. A first series of questions is presented on the display to select one of a plurality of branched chain algorithms which assess the patient for an appropriate timing and level of medical care. A second series of questions is presented on the display to guide the patient through the selected one of the plurality of branched chain algorithms.

Answers from the patient to the second series of questions are entered in the data processing system. A medical care timing and level of medical care recommendation is made in response to patient answers to the second series of questions.

In a further aspect of the invention, a data processing system includes a patient assessment stored program utilizing a plurality of branched chain logic algorithms. A stored program editor generates branched chain logic algorithms. The branched chain logic algorithms each are configured to present a series of questions answerable with "yes" or "no". The stored program editor for generating branched chain logic algorithms includes a yes-no logic block for generating the questions answerable with yes or no and an endpoint logic block for generating endpoints in the plurality of branched chain logic algorithms.

The attainment of the foregoing and related objects, advantages and features of the invention should be more readily apparent to those skilled in the art, after review of the following more detailed description of the invention, taken together with the drawings, in which:

BRIEF DESCRIPTION OF THE DRAWINGS

FIG. 1A is a more detailed block and flow diagram of a portion of the medical network management system shown in FIG. 1.

FIGS. 59–78 are screens used in implementing a portion of the medical network management system in accordance with the invention.

DETAILED DESCRIPTION OF THE INVENTION

Figure 1:
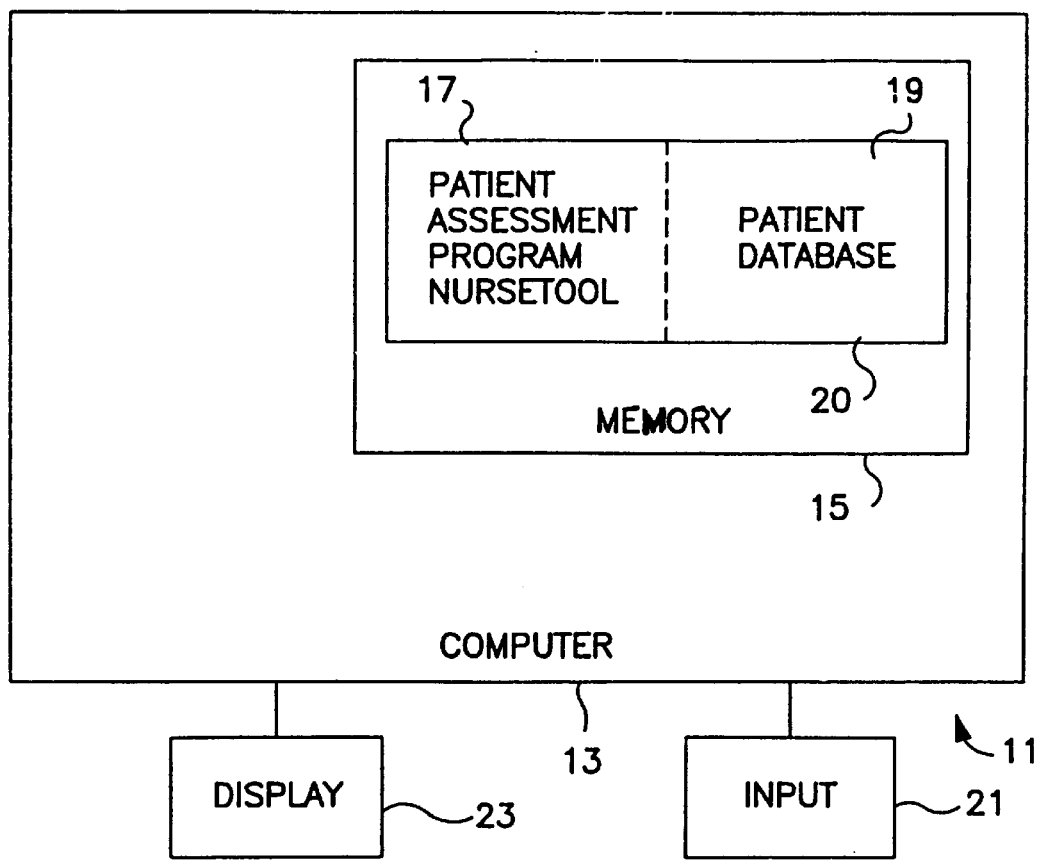
FIG. 1 and 1A is a generalized block diagram of a medical network management system in accordance with the invention.
Figure 2:
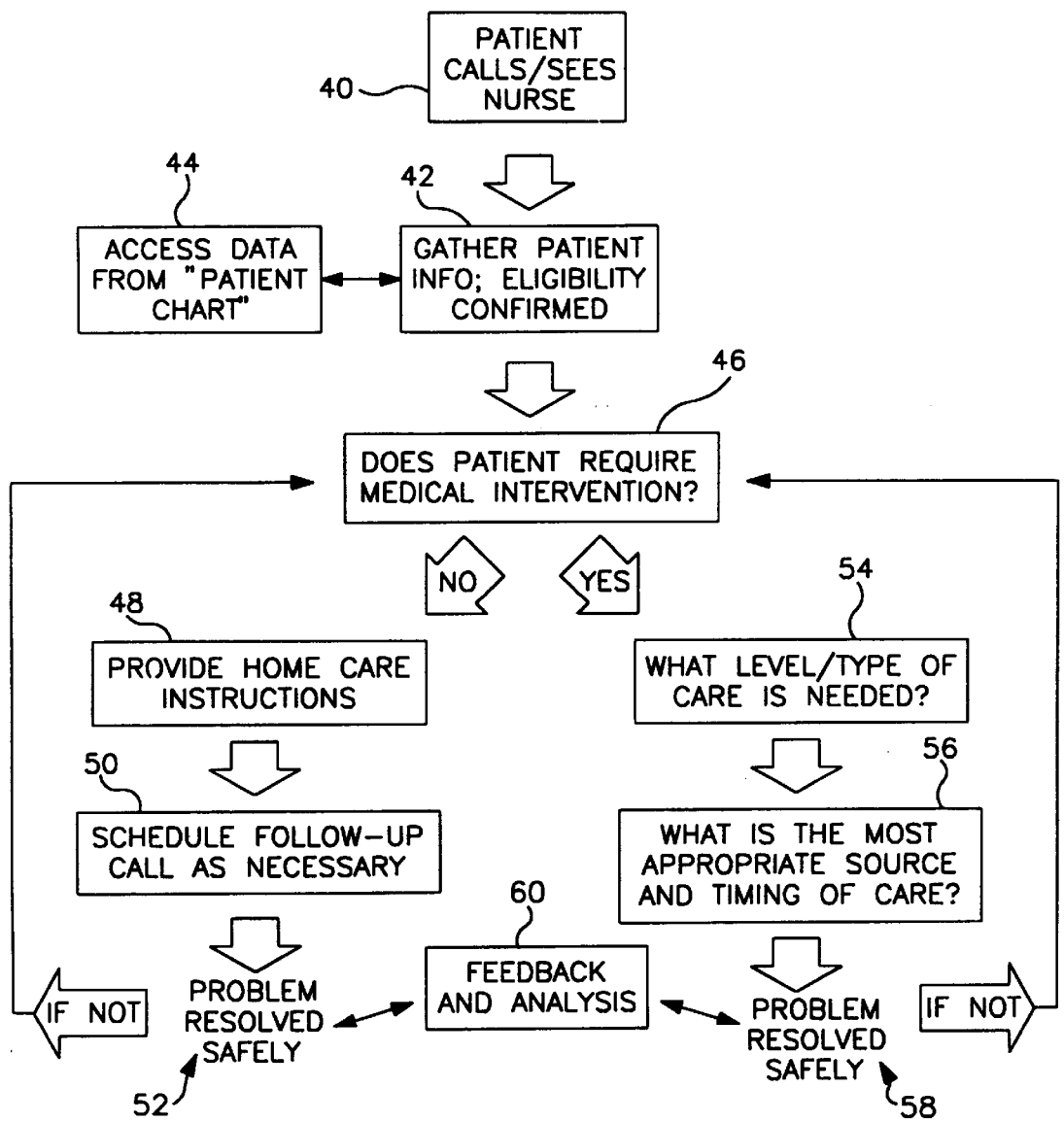
FIG. 2 is a generalized flow chart for a medical network management process in accordance with the invention.

Turning now to the drawings, more particularly to FIG. 1, there is generally shown a medical network management system (NMS) 11 of the invention. Through the NMS 11, health plan beneficiaries access a team of health care professionals over the telephone to help them assess their health needs and select appropriate care. FIG. 2 provides a schematic of this call process.

The NMS 11 includes a computer 13, which is typically a Sun workstation or other Unix compatible workstation. The computer 13 has a memory 15, which contains network management software and data 20. The network management software and data 20 includes a patient assessment program 17 and a patient database 19. The computer 13 has an input device 21 and a display 23 for user interaction with the network management software and data 20.

Figure 1A:
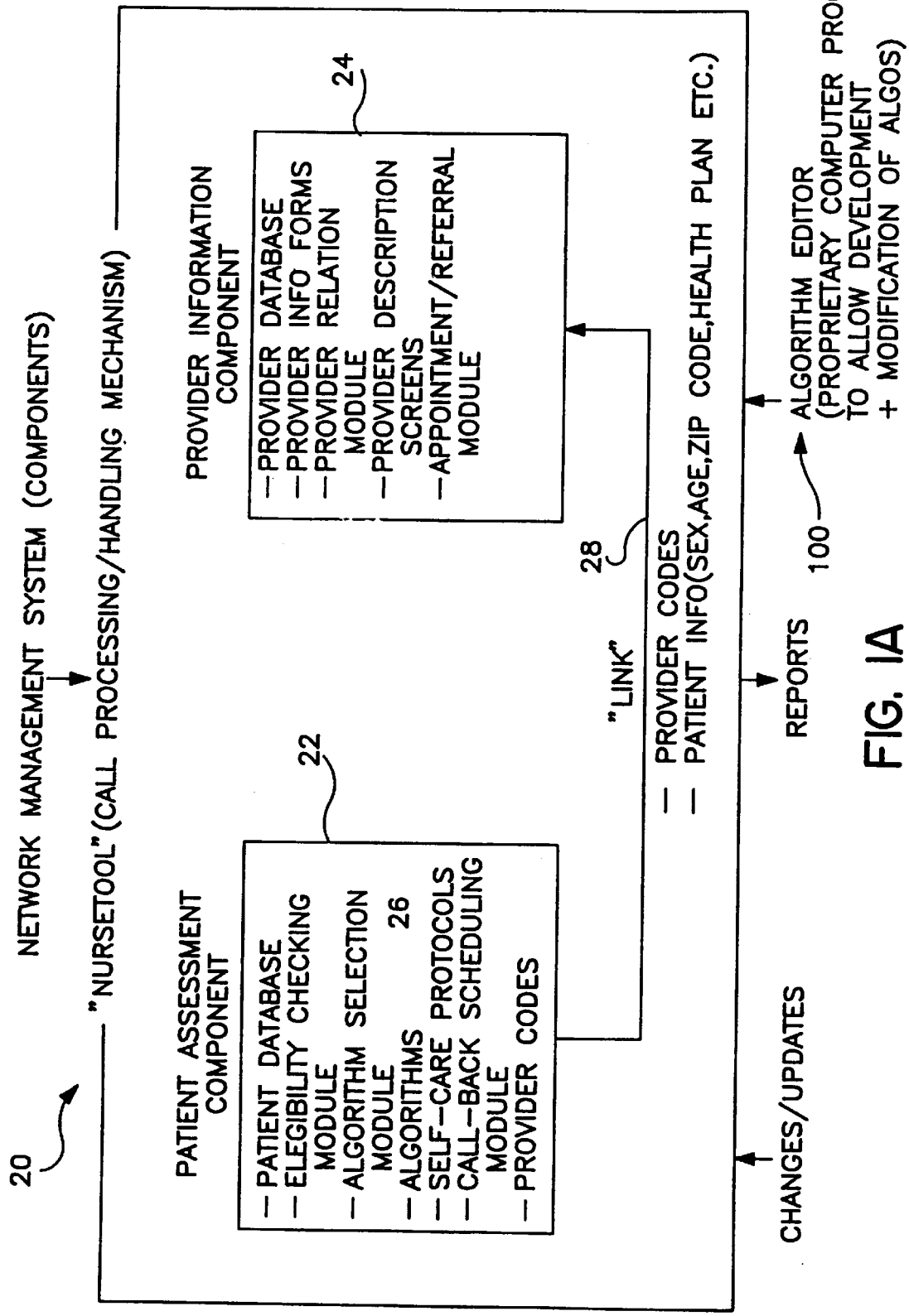

Further details of the network management software and data 20 are provided in FIG. 1A.

The NMS 11 has two primary components. They are the:

Patient Assessment Component 22, and the

Provider Information Component 24.

Patient Assessment Component 22

This first component of the system consists of a set of information tools which are used by health care professionals to assess patient conditions and assist in the selection of health care services and to help patients find appropriate care at the appropriate time.

The key piece of this front-end system component is a comprehensive, automated set of proprietary assessment algorithms 26. These unique, clinical tools enable a trained nurse to sort patients into different risk categories, safely and effectively without requiring a medical diagnosis. Patients can then be guided to an appropriate level and type of care for their problem(s) based on their level of risk and set of potential needs.

To understand risk sorting, consider 10,000 beneficiaries of a health plan. In a year, almost 1000 times members of this group will become patients seeking medical care for lower back pain symptoms. Among those who receive care, there will only be a very small number of patients whose pain actually results from serious, but infrequent causes.

A series of questions, asked in the correct order, can clearly identify those patients for whom these serious causes cannot be safely eliminated. They must all receive immediate, proper medical care to actually search for any of these conditions and potentially prevent very serious consequences.

Once these patients with potential infrequent problems are identified, the remaining patients, over 950, are those almost certainly experiencing some form of musculo-skeletal back pain, which is almost always self-limiting and self-correcting. None are in immediate danger of death or further injury. If symptoms persist, a higher level of medical care could then be appropriate.

Table 1 below describes the statistically probable number of clinical causes for lower back pain as discussed above.

TABLE 1

| Clinical Causes of Back Pain | |
|---|---|
| Emergent (e.g., dissecting aortic aneurism) | 10 |
| Non-musculo-skeletal (e.g., bladder infection) | 35 |
| Musculo-skeletal, potentially benefits from medical care | 65 |
| Muscuo-skeletal, self-limiting, self-correcting, little benefit from medical care | 890 |
| Total | 1000 |

Through the process of asking questions and sorting patients by risk categories, the striking results displayed in Table 2 below can safely be achieved.

TABLE 2

| Source of Probable Treatment of 1000 Patients With Acute Lower Back Pain | | | |
|---|---|---|---|
| INITIAL PROVIDER | UNDER FEE FOR SERVICE | UNDER MEDICAID | UNDER NMS |
| Emergency Department | 100 | 300 | 0 |
| Provider Appointment, all other causes | 700 | 600 | 350 |
| Self Care | 200 | 100 | 620 |
| Total Patients | 1000 | 1000 | 1000 |
| Total Charges (in 000's) | $67 | $63 | $25.5-FFS**$19.4-Medicaid |

**Note that FFS stands for fee for service and these two numbers represent the costs incurred when using the NMS to provide access for either fee for service or Medicaid patients.

When any of the algorithms indicate that medical intervention is appropriate for a given patient, the nurse will then use the second major component of the NMS, which is described below, to assist that patient in selecting an appropriate, individual provider.

Provider Information Component 24

The second major component of the system consists of a proprietary relational database which contains the information necessary to effectively differentiate the various providers participating in a given network and to manage the patient flow into their practices. This system component enables the nurse to help patients select an individual doctor, clinic, or hospital; an appropriate provider of the services required to meet their needs. The patient assessment component 22 and the provider information component 24 are linked at 28 by provider codes, which identify by standard procedure billing codes, what procedures the different providers perform in the normal course of their practice. The link 28 further includes patient information, such as sex, age, zip code, health plan and other patient information useful for matching a patient to a provider.

Data describing areas of clinical expertise and the practice in general, is collected from each provider. This information is monitored and updated regularly. It can also be augmented by relevant information from other sources such as claims data and can contain items such as procedural frequency or clinical outcomes.

Medical Network Management Process

Nurses search the information using the criteria necessary to meet specific patient needs as identified through the assessment process. An example of the assessment process is provided in FIG. 2. The process begins when the patient calls or sees a nurse utilizing the NMS 11 at 40. Patient information is gathered and eligibility is confirmed at 42 by accessing data from a patient chart at 44. A determination is then made at 46 whether the patient requires medical intervention, using the algorithms 26. If medical intervention is not required, home care instructions are provided at 48 and a follow-up call is scheduled at 50. In follow-up a determination is made at 52 whether the problem has been resolved safely. If not, another determination is made at 46 whether medical intervention is required.

At either stage, if the determination at 46 is that medical intervention is required, a determination is then made of what level and type of care is needed at 54. The most appropriate source and timing of the care is made at 56. A determination is made at 58, usually by the caregiver, whether the problem has been safely resolved. If not, another determination is made at 46 whether medical intervention is required. At either 52 or 58, when it is determined that the problem has been resolved safely, feedback and analysis to the NMS 11 is provided at 60.

To better understand provider selection, again consider the 1000 patients with lower back pain. Without the NMS 11 to help guide patients, many individuals who have a self-correcting condition will see a doctor and begin to receive care that in most cases will not have medical benefit. Many expensive CT or MRI scans may be performed to try to determine the cause of pain which, in most cases, will go away on its own with a proper self-care regimen.

Many patients will also receive treatment from a provider who does not necessarily focus on the management of lower back pain. The result is often lower quality care than can be predictably delivered by a doctor who focuses in this area. For example, if the initial consultation is with any surgical specialist, the statistical likelihood of surgical intervention is two to three times that occurring when care begins with a non-surgical provider . . . and with no improvement in long term outcome and at much higher costs.

The following table depicts the potential impact from the Provider Access Service on the utilization of medical services by the 1000 lower back pain patients described above, in addition to the initial doctor visit.

TABLE 3

Distribution of Additional Medical Care

| ADDITIONAL CARE | UNDER FEE FOR SERVICE | UNDER MEDICAID | UNDER IAS |
|---|---|---|---|
| Diagnostic Tests | 600 | 720 | 150 |
| Medical Treatment | 280 | 270 | 70 |
| Surgical Treatment | 120 | 180 | 80 |
| Total Additional Care (in 000's) | $977 | $930 | $553-FFS** $395- Medicaid |
| Total Care (in 000's) | $1,044 | $993 | $578-FFS $414- Medicaid |

**Note that savings from the NMS will be even greater over time as information is added which identifies providers who use less invasive, less costly procedures or ones who achieve more favorable, less costly outcomes.

Inefficiency such as that depicted in the preceding examples of the treatment of lower back pain, is endemic in American health care. It exists largely because of the uninformed and ineffective matching of patient need with provider services. To date, efforts at managing care have not been able to eliminate much of this inefficiency because of the non-integrated approach they have taken.

Research abounds which indicates that the opportunity for improvement in the current delivery of care through the NMS is significant.

Rand Corporation studies suggest that over ½ of all procedures currently performed each year may have no discernable medical benefit.

In the National Center for Health Statistics' surveys of practicing doctors by specialty, providers themselves estimated that approximately ½ of all ambulatory care office visits were not medically necessary.

National experts in Medicaid health care patterns state that over ½ of the emergency room use by Medicaid recipients nationally, is inappropriate.

The patient assessment component 22 and the provider information component 24 of the NMS 11 can be used or sold separately or together as part of the NMS 11. The algorithms 26 provide a mechanism by which one can examine the presence of one or more concerns or etiologies as the underlying cause of patient symptoms.

Each yes/no stem question must be answered yes or no and leads to another question or action recommendation or transfer to another algorithm. Bayes Theorem provides the underlying rationale as to why this process works. The nodes are not all related to each other, nor are they probabilistically dependent on each other. If a stem question, high sensitivity, is answered yes, then in many cases and in general, questions of higher specificity are asked to determine more accurately the appropriate action or intervention which should take place, by whom, and in what time frame. The algorithms sort patients by "risk", in that, if you cannot eliminate with an acceptable level or degree of risk the potential that a significant concern or etiology is present, then an action or recommendation appropriate for that concern or etiology is arrived at by the system. The actions and endpoints of the algorithms are of a limited number and variety, and are intended to represent generally the categories of options available to a patient within a typical health care system.

In the cases where an interaction by another "provider" is recommended, the system also presents specifications describing an "appropriate" provider. These specifications can be any number of items, including clinical codes, procedural codes, doctor specialty, or even a specific provider or clinic. If the algorithms are not attached to a provider database, then these specifications would be available as general guidelines for the appropriate next recommended intervention.

If a provider database is attached, data from the call and the algorithm will "link" into the provider selection process, as indicated at 28. Here, the specifications already determined, including the patient health plan, sex, age and any relevant clinical codes and/or procedure codes are carried across into the provider selection process. The clinical codes are used in a unique manner in the process. The participating providers provide information about themselves, their practices, and the clinical services they offer. This information is collected with NMS forms, augmented by any other sources of data available, and loaded into a database. This information represents the "supply" of services then available to meet the "demand" of patient needs within a given group of patients and providers. Another way to express this unique application of the clinical codes is that they allow the provider to represent the services they provide, and thus describe the profile of the patient/patient problems they treat or do not treat.

This use of such clinical codes in a "prospective" manner to try to manage the appropriate matching of demand and supply—patient need with provider services—within a health care system is unique. Many of these codes were developed and historically have been used to provide retrospective information about what was done. This information is often used to bill for services and account for patient problems.

Another feature of the system and process is that the clinical or procedural codes extend to the health plan or insurer or whoever manages or controls the provider network the ability to control the specific services available from specific providers. Over time and with experience, the health plan manager can then retrospectively go back into the database and change the "care paths" allowable or available to different patients to continue refining and improving the quality of care provided.

The clinical codes used in the system and process are based on the following classification systems:

ICD.9.CM, provided in "International Classification of Diseases," 9th. Revision, 3rd Edition, with Clinical Modification.

DSM-III-R, provided in "Diagnostic and Statistical Manual of Mental Disorders," 3rd. Edition, Revised (Washington, American Psychiatric Association, 1987).

The procedural codes used in the system and process are based on the following classification systems:

CPT-4, provided in "Physicians Current Procedural Terminology," Fourth Edition, developed and revised by Department of Coding and Nomenclature, American Medical Association.

CDT, provided in "Current Dental Terminology," First Edition, 1990–1995, American Dental Association.

Additional clinical codes which both represent services offered or provided by providers and needed by patients are used in the system and process. Typically, these additional codes describe clinically what might be wrong with the patient, what might be needed by the patient, what the provider treats, does or has available (equipment). Not everything is included in the above published coding schemes.

The system and process further provides a "call processing" mechanism, described more fully below, which assists the user in handling a patient interaction and making appropriate use of the algorithms and provider database. This mechanism records every "keystroke", including all free text comments, so that records of all calls are retained. The system can generate reports describing the use of the system and its components, so that it can be improved over time. The architecture of the system is flexible. Most components, including algorithms, self-care instructions and provider codes can be easily modified without altering the underlying computer code.

The NMS Algorithms

The purpose of the yes-no branched chain algorithm logic of the NMS system and process is neither to diagnose nor to treat medical conditions. Rather, the algorithms logically sort a population of individuals who have, by telephone, identified themselves or someone else as possibly in, usually because of a new sign or symptom which the caller feels is possibly due to an illness or to an injury, and who are seeking advice on what to "do next."

The NMS algorithm logic uses the principles of Bayes Theorem to identify some sub-populations whose risk of serious illness or injury is so low as to make home care an appropriate choice and to, by exclusion, identify other populations whose risk of serious illness or injury is high enough to warrant provider evaluation. Further, the NMS algorithm logic is able to identify from among those populations requiring provider evaluation various sub-populations whose requirement for provider evaluation vary in their time urgency and the required medical service capability of the provider. The NMS algorithm logic is also able to identify for those populations requiring provider evaluation the essential provider medical skill set required for an efficient and effective evaluation of each sub-population.

Coupled with the NMS provider matching logic, this allows NMS to determine for each caller:

whether provider evaluation is needed;

if provider evaluation is needed, how soon it is needed;

if provider evaluation is needed, what constitutes the requisite skill set a provider needs to be effective and efficient in caring for the conditions likely to be causing the sign or symptom prompting the telephone call;

which providers have that requisite skill set and are available in the required time-frame.

Bayes Theorem describes how, when individual members of a population already at a low pre-test possibility for a condition have a negative result to a test of high sensitivity for the presence of that condition, the post-test probability of that condition is extremely low. Bayes Theorem also describes how, when individual members of a population at low pre-test possibility for a condition have a positive result to a test of high sensitivity for the presence of that condition, the post-test probability of that condition is not (clinically) significantly higher than was the pre-test probability.

The NMS system uses complaint-specific algorithms to determine by telephone the appropriate "next medical step" for a caller. Review of medical statistics shows that, in the United States, almost regardless of the nature of the sign or symptom, serious illness/injury is at very low pre-test probability: of ambulatory patients evaluated in physician's offices, far less than one percent require hospital admission; of callers summoning dispatch of ambulances via 911 telephone, a small percentage are admitted to hospital; of ambulatory patients evaluated in hospital Emergency Departments, less than 5% require hospital admission.

The NMS algorithms use as "tests" various yes-no questions selected by clinical experts on the basis of their high sensitivity for the presence of diseases/conditions which, if not evaluated by providers, may significantly harm the caller. The algorithms apply these highly sensitive "tests" to caller populations already at low pre-test probability of serious illness/injury, as described above.

Thus, Bayes Theorem describes the clinical implications of both "positive" and "negative" "test results" in the NMS system:

Callers with negative results (responding with "no" answers) to these tests (yes-no questions) have an extremely low post-test probability of the illness/injury under consideration.

Callers with positive results (responding with "yes" answers) to these tests (yes-no questions) have a post-test probability of the illness/injury under consideration that is not (clinically) significantly different than before the "test" was performed, i.e., the test cannot sufficiently lower the probabilities.

For a population at low pre-test probability of specific illnesses/injuries, the NMS algorithms perform one or several tests of high sensitivity for a specific illness/injury. The NMS algorithms then iteratively repeat that testing process by applying tests highly sensitive for each condition which must be eliminated. The algorithms are deliberately designed to try to eliminate the possible presence of illnesses/injuries of extreme medical time-urgency and to test subsequently for less time urgent illnesses/injuries. The algorithm logic considers members of a population identified by this iterative process as being at extremely low post-test probability for all conditions which must be detected as suited to self-care. The algorithm logic considers as requiring provider evaluation those members of a population identified by this iterative process as having positive "test" results which do not allow sufficient reduction of the probability of an illness/condition. The time urgency for that required provider evaluation is a clinically established derivative of the nature of the illness/injury whose probability has not been (clinically) sufficiently reduced by the testing procedure.

Figure 3:
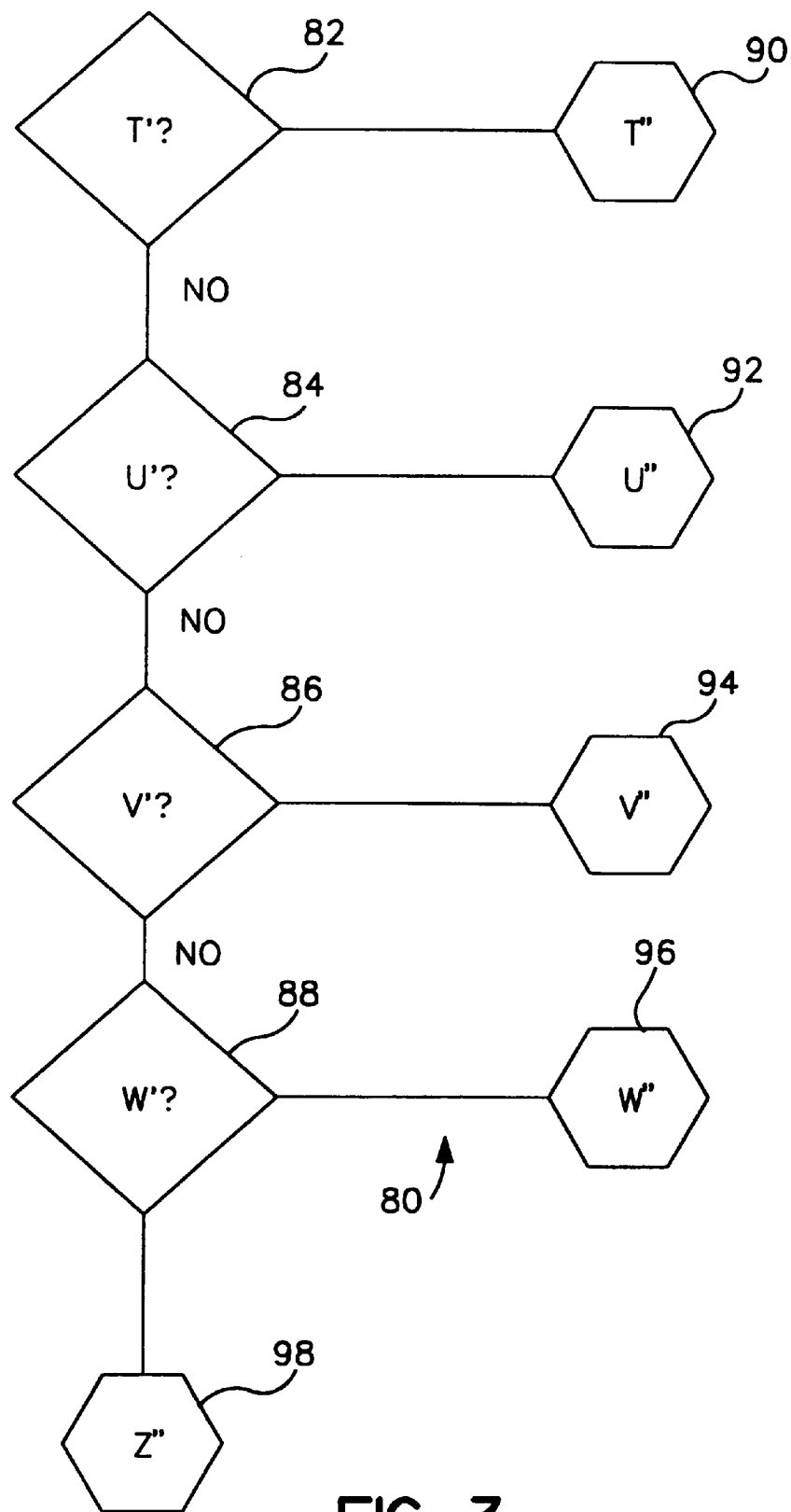
FIG. 3 is a flow chart of a portion of the medical network management process of FIG. 2.
Figure 4A:
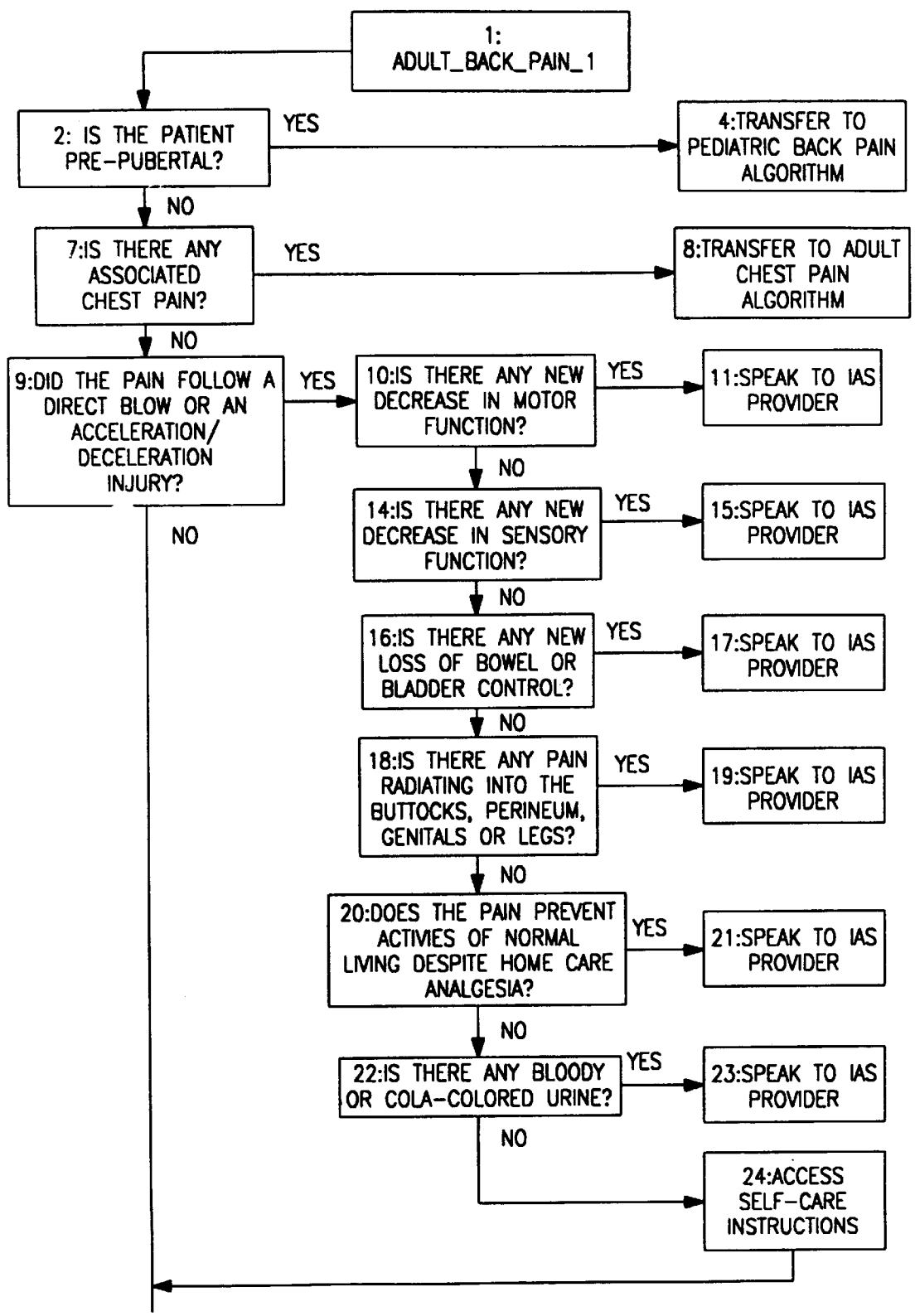
FIGS. 4A–4E are flow charts of a representative algorithm incorporated in the system and process of FIGS. 1–3.
Figure 4B:
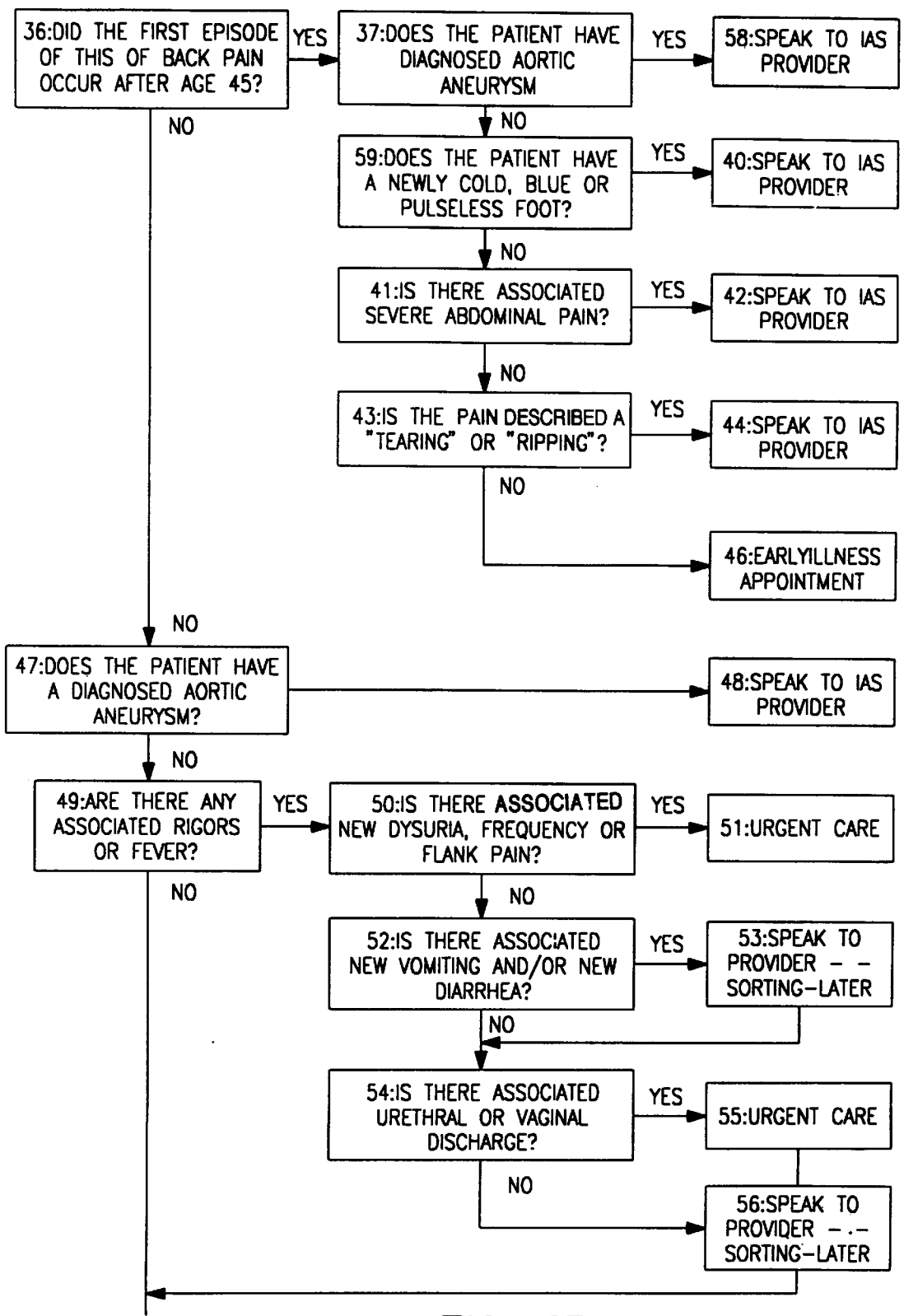
Figure 4C:
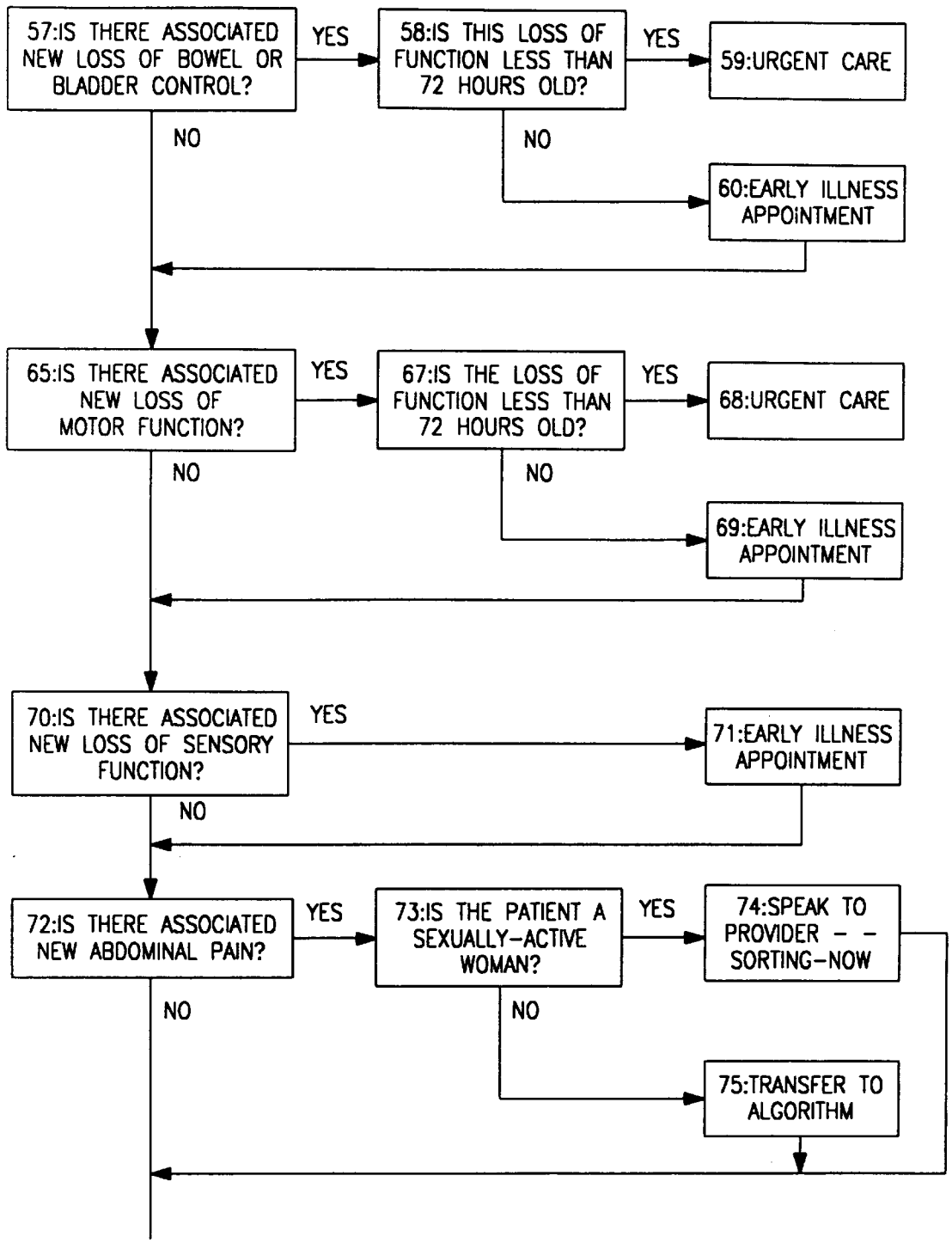
Figure 4D:
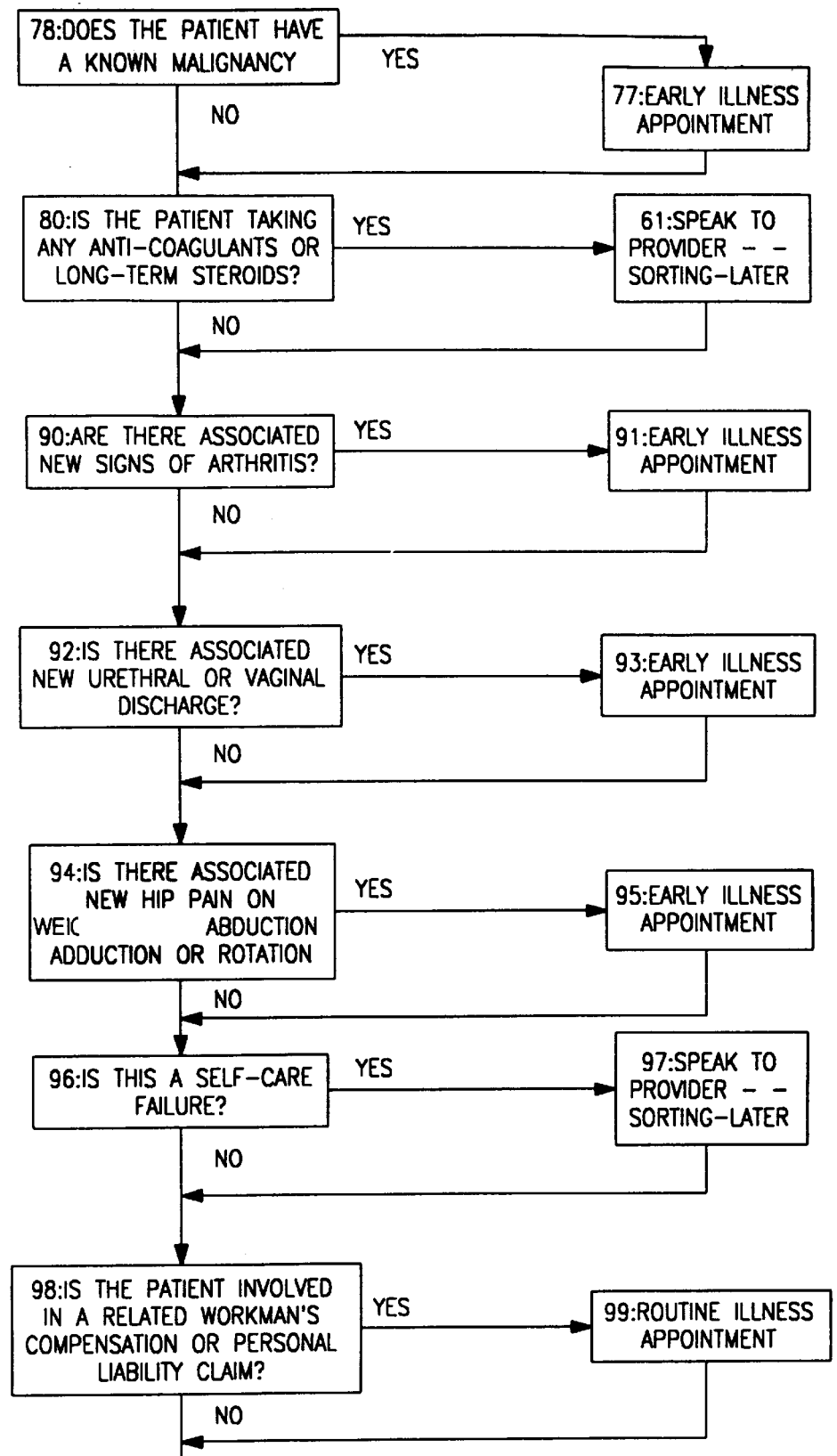
Figure 4E:
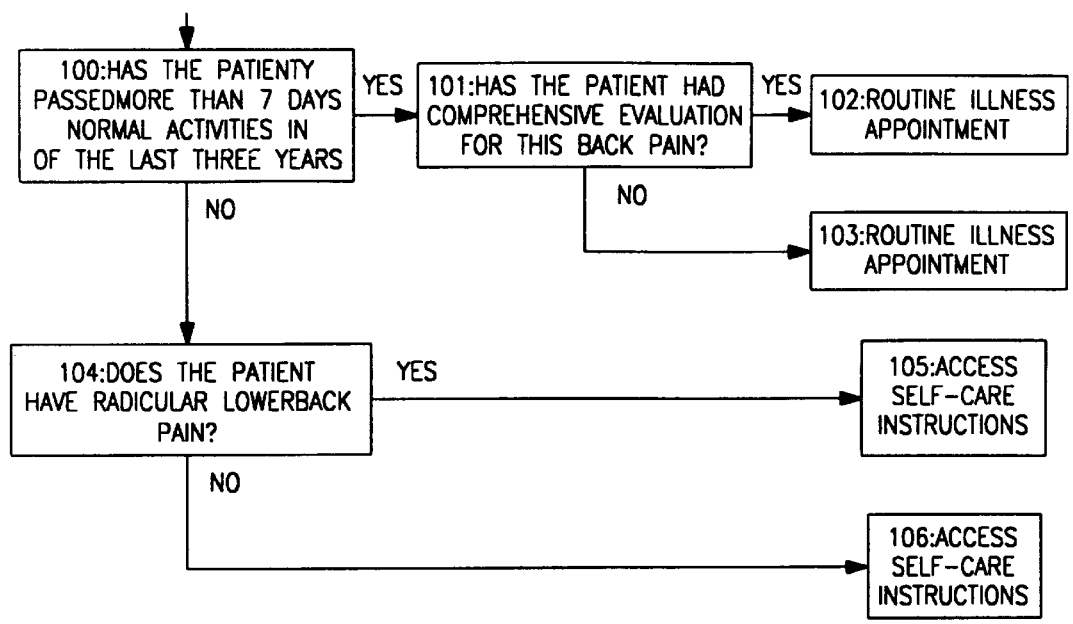

Further details on the applicability of Bayes Theorem to the NMS algorithms are provided in FIG. 3. Assume that, for a population exhibiting sign/symptom "A", clinical expertise establishes that:

if the established probabilities of illness/injury T, U, V, or W exceed "low," provider evaluation is medically appropriate;

if the established probabilities of illness/injury T, U, V or W are each "extremely low" or less, self-care is medically appropriate; questions T', U', V' and W' in algorithm 80 at 82, 84, 86 and 88 respectively are each highly sensitive for illness/injury T, U, V, and W respectively.

Then, the algorithm 80 produces the indicated five sub-populations:

Population T" at 90, where the probability of illness/injury T is greater than "low" and whose members therefore require provider evaluation for illness/injury T;

Population U" at 92, where the probability of illness/injury U is greater than "low" and whose members therefore require provider evaluation for illness/injury U;

Population V" at 94, where the probability of illness/injury V is greater than "low" and whose members therefore require provider evaluation for illness/injury V;

Population W" at 96, where the probability of illness/injury W is greater than "low" and whose members therefore require provider evaluation for illness/injury W;

Population Z" at 98, where the probability of illness/injury T, U, V, or W is extremely low, and, therefore, for whose members self care is appropriate.

Attached as an appendix to this application is a representative algorithm for the NMS system, covering adult back pain. FIGS. 4A–4E illustrate the branched chain logic for this algorithm. Each of the NMS algorithms has four components:

The Cover Sheet:

The cover sheet provides a variety of information about the algorithm, including conditions considered, estimated action point distribution, and excluded conditions. The algorithm cover sheet is intended to provide a comprehensive overview of the algorithm. The key uses of the information are as follows:

Algorithm Selection The fields "Algorithm Name," "Category," "Keywords" and "Similar Complaints" are all used to assist the nurse during the automated process of selecting an appropriate algorithm.

"Opening Screen" In the NMS system, once a nurse has selected a given algorithm, an opening screen appears, which provides a brief description of the algorithm, including the following fields:

"What Does it Do?"

Algorithm Road Map (intended to give nurse a sense of the length of the algorithm)

Excluded Populations

Relevant Medical Risk Factors

Utilization Management Each and every algorithm as an "Anticipated Call Distribution." This represents the best judgement of an experienced medical staff based on their cumulative experience and will serve as the baseline for evaluating the efficiency of the algorithm and will be updated with the availability of empirical data.

Clinical Overview The "Areas of Inefficiency/Anticipated Economic Impact" provides a clinical synopsis of the algorithm, essentially representing a differential diagnosis of the presenting complaint, together with estimates of its prevalence, severity, and recommended level of intervention.

The Logic:

The algorithms' formal logic is branch-chained and binary. (An unsure answer has information to help determine whether to defer to yes or no.) Its use by nurses standardizes their evaluation while allowing the nurse to add his/her professional expertise to the information gathered (but not to idiosyncratically replace the formal logic) to "sort" best a patient's problem. The logic "sorts" to several defined "action points" whose definitions are central to the process. The algorithm logic lays out the questions in the order they will be presented to the nurse by the system. The algorithms represent branched chain logic, with the most sensitive questions being asked first, moving on, in response to positive answers, to more specific questions to identify more specifically timing and type of appropriate care. The numbering of the nodes or boxes in FIGS. 4A–4E corresponds with the corresponding points in the node text of the appendix.

The NMS system includes a unique Algorithm Editor, which allows a clinician, rather than a programmer, to create and/or modify an algorithm without having to write code. FIGS. 4A–4E and the corresponding node text of the appendix is output from that tool.

The Node Text:

The node text is the "why" behind the algorithm logic. For each yes-no branch and each action point, the algorithm authors have written their medical explanation of the logic in standardized format. This also includes scripted questions for the nurses to use, should they so wish.

The algorithm node text is the supporting data for each and every question and end point in the NMS system. Most of this information is visible to the nurse as he/she "traverses" a given algorithm. As with the algorithm logic, any text changes in the node text can also be modified by a medical administrator through the Algorithm Editor, without writing code. This allows knowledgeable users of the NMS system essentially to create their own "customized" algorithms, using those provided with the system as a base. The following is a brief description of the categories within the node text of the appendix. An understanding of the action point definitions is central to evaluating the algorithms. They are:

INITIATE EMERGENCY PROCEDURES: The NMS nurse will connect the caller to the local EMS Dispatcher without further delay. (Used when there is reasonable reason to suppose the need for on-site and en-route care beyond the capabilities of the typical caregiver.)

SPEAK TO NMS PROVIDER: The NMS nurse will connect the caller to a physician who works with the NMS system to complete the triage encounter. (Used when there exists a possible need for EMS Dispatch, but when a physician interview may identify more appropriate actions, i.e., cuts down on the "false positive" EMS Dispatches.)

URGENT CARE: The patient needs care now (e.g., a deep and dirty laceration), but does not need EMS care on site or en route. While urgent care can be delivered in hospital-based emergency departments, free standing emergency clinics, and doctors' offices, it does require that the site be open at the time the care is needed, since the care cannot be delayed.

SPEAK TO PROVIDER-SORTING: The NMS nurse will assist the caller in speaking to a physician whose role will be to determine the appropriate next step in the patient's care. This physician can be the patient's primary care physician, the physician "covering for" the patient's primary care physician, or a physician in the employ of the patient's insurance carrier. (Note: The NMS algorithm logic can designate that this contact occur either "NOW" or "LATER". The "NOW" designation means that the caller should speak to the physician as soon as possible; the "LATER" designation means that the contact can be delayed for up to 4 hours.

SPEAK TO PROVIDER-TREATMENT: The NMS nurse will assist the caller in speaking to a physician whose role will be to decide whether appropriate care can be initiated by telephone with follow up care by appointment This physician can be the patient's primary care physician, the physician "covering for" the patient's primary care physician, or a physician in the employ of the patient's insurance carrier.

EARLY ILLNESS APPOINTMENT: The NMS nurse will assist the caller in establishing an appointment with an appropriate provider "the next time that office is open". Most often this will be an appointment "later today" or "tomorrow"; however, a call late Friday evening might result in an appointment Monday morning.

ROUTINE ILLNESS APPOINTMENT: The NMS nurse will assist the caller in establishing a "routine" appointment with an appropriate provider. The standard is that the appointment will be no later than two weeks from the date of the call.

SELF CARE: The NMS nurse will instruct the caller in understanding why self care is the most appropriate "next step", explaining the steps of self care, "granting call-back permission" to the caller, and scheduling any needed outward calls from the NMS system to the caller.

The formal structure of the NMS algorithm logic can designate that the NMS nurse either act on these action points as soon as they are reached (as a true end-point) or act on them "at the end of the algorithm". In the event that the NMS nurse reaches the end of an algorithm and the algorithm logic has made more than one recommended action, the NMS nurse will carry out the recommended action of the highest priority.

Also important in understanding the NMS algorithms is realizing the distinction made in the node text between a "provider examination" (requires in-person contact between patient and provider) and a "provider evaluation" (which could be confined to a telephone conversation between caregiver and provider).

The Self Care Instructions:

For many patients, self care under the supervision of a caregiver will be the most appropriate care. The NMS Self Care Instructions guide the NMS nurse in providing for the caregiver an explanation of what is likely going on, things to do to lessen symptoms, call-back guidelines for the caregiver to use, and a mechanism to schedule NMS callbacks to the caregiver, if appropriate and desired by the caller.

Use of the NMS System Software

Figure 5:
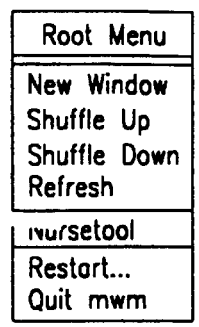
FIGS. 5–58 are screens used in carrying out the process of the invention using a preferred embodiment of the system of the invention.

The Network Management System software is started by selecting the Nursetool choice from the Motif Root Menu. An example of a Motif Root Menu is shown in FIG. 5.

Use the mouse to position the pointer in an open area of the screen.

Hold the left mouse button down.

The Motif Root Menu displays.

Drag down the menu to the Nursetool selection.

Release the mouse button.

Figure 6:
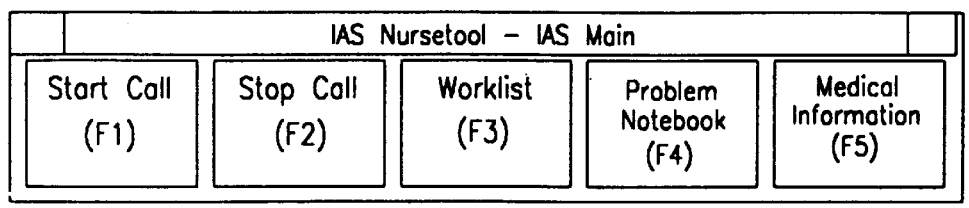

The NMS Main button bar displays (see FIG. 6).

Stopping the 'AS Network Management System

The NMS software is stopped by selecting the Close choice from the NMS Main button bar Window Manager Menu.

Use the mouse to position the pointer on the Window Manager Menu button at the left edge of the title bar in the NMS Main button bar. (See FIG. 6.)

Hold the left mouse button down.

The Window Manager Menu displays.

Drag down the menu to the Close selection.

Release the mouse button.

The NMS Main button bar and any open windows of the NMS software disappear from the computer screen.

1 Starting a Call

Overview of the Call Process

The NMS is intended to be used as the first point of contact for a patient entering the health care system—i.e., those seeking medical care, health care advice, or information. As such, it has been designed to support a range of health care needs including:

Emergency calls

Illness Care calls (symptomatic patients)

Provider Selection calls

Health care information calls

Callbacks to the patient

When a call is received or a patient transaction begins, a judgment must be made about the caller's needs. The initial version of the NMS currently provides for four types of calls:

Emergency—Calls requiring immediate assessment of a patient's medical problem and possibly immediate referral of the patient to a provider for medical attention are handled through the Emergency process. Emergency calls do not require verification of the patient's eligibility for referral.

Illness Care—Medical problems that are not emergencies, but require assessment of the patient's condition are processed as Illness Care calls. A series of algorithms are used to walk you through the assessment process. Illness Care calls require verification of the patient's eligibility record in the system. If eligibility records do not exist in the system, you may create a New Patient Chart to add the patient's eligibility record.

a Provider Selection—Calls requesting help in selecting physician the appropriate medical provider are processed as Provider Selection calls. The Provider Selection function can also be used when an Illness Care call results in requiring provider selection.

Information—Patient requests for information on self-care and/or insurance rules for a particular plan are processed as Information calls. Information calls require verification of the patient's eligibility record in the system or creating a New Patient Chart.

Other—Calls that are inappropriate for the NMS software are processed as Other calls.

Processing a Call

Click the Start Call button in the NMS Main button bar (FIG. 6) or press F1.

Figure 7:
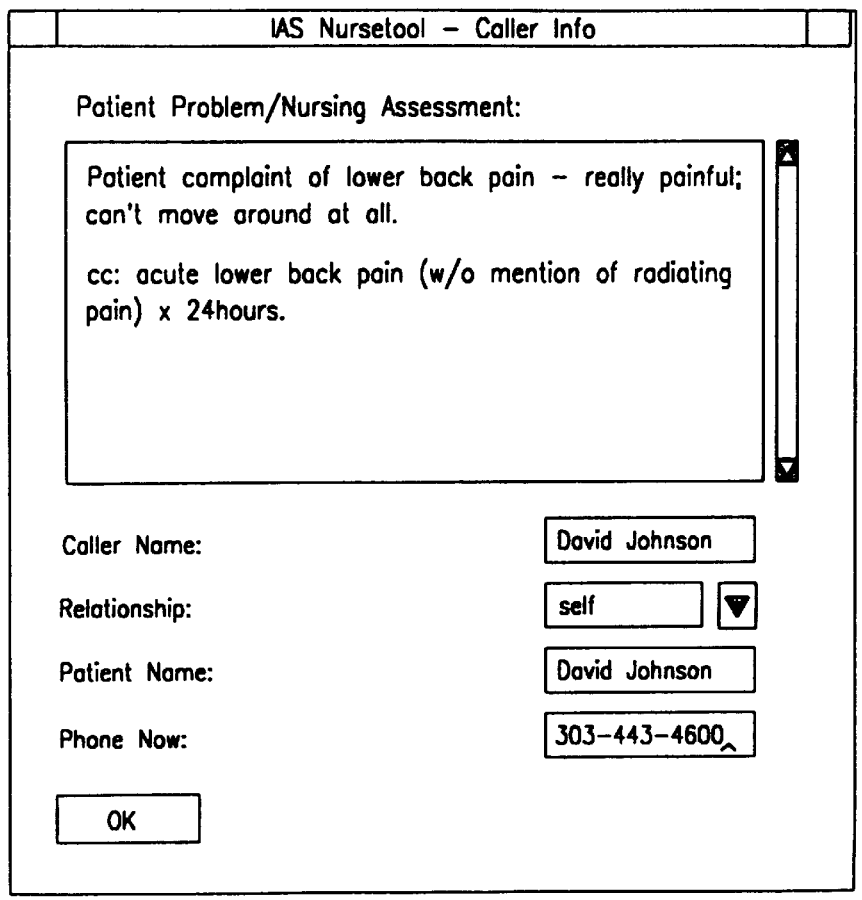

The Caller Info window (FIG. 7) and the Call Type Selection bar (FIG. 8) display. The NMS Main button bar remains on the screen.

Initial Information

Initial information about the caller and the nature of the call is entered into the Caller Info window. The text box in the Caller Info window is a repository for free-form comments about the call. Comments entered here are saved as a permanent record with the other information entered during the call session.

The Caller Info Window

Click the Start Call button in the NMS Main button bar or press F1.

Patient Problem/Nursing Assessment—Type the following:

the caller's description of the patient's problem, and the nurse's assessment of the patient's problem.

The description should be sufficiently detailed to assist in selecting an appropriate algorithm.

You may add text to this box at any time during the call session. Additional comments will be saved to the database when the call session is ended.

Caller Name—Type the first and last names of the caller (separated by a space), even if the caller is other than the patient.

Relationship—Enter the caller's relationship to the patient. The list button opens a list box with the acceptable entries for this box. The choices are:

Self

Parent

Grandparent

Relative

Friend

Other

Select (or type) Self if the caller is the patient.

Patient Name—Type the first, middle and last names of the patient (each separated by a space). If you entered Self in the Relationship text box, the Patient Name box will be automatically be filled in with the name you entered in the Caller Name text box.

Phone Now—Type the phone number of the caller, even if the caller is other than the patient. Use the format: (401) 555-8571.

OK—Click the OK button to save the information you entered in the Caller Info window. The Caller Info window remains open on the screen and the OK button dims.

The Caller Info window will remain available on the screen as a window or an icon until the call session is ended You may add data to the Patient Problem/Nursing Assessment text box or change the information in any of the other text boxes in the Caller Info window at any dime during the call session. The additional information will be saved to the database when the call session is ended.

Minimizing the Caller Info Window

You may minimize the Caller Info window to an icon at any time during the call session.

Click the close box in the top right corner of the window.

Figures 8, 9, 10:
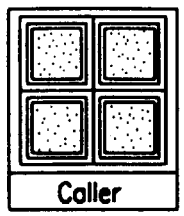

The Caller Info window will be minimized to an icon at the bottom of the computer screen (FIG. 9).

Opening the Caller Info Window Icon

You may open the Caller Info window from its icon if desired.

Double-click the Caller Info icon at the bottom of the computer screen.

The Caller Info window will display.

What Next?

When you have completed the required entries in the Caller Info window, select a call type from the Call Type Selection button bar as described above.

Selecting the Type of Call

The Call Type Selection button bar is displayed when you select Start Call from the NMS Main button bar. Each button on the Call Type Selection button bar starts a different type of session for interacting with the caller. The Call Type Selection button bar remains displayed during a call session in case the nurse needs to change a call type.

Emergency (F6)

Click the Emergency button or press F6 when you perceive the caller has a life-threatening emergency that requires life support transportation (essentially equivalent to calling 911). This will start the Emergency call process so that you can direct the patient to immediate medical attention.

Emergency calls do not require verification of the patient's eligibility for referral Illness Care (F7)

Medical problems that are not life-threatening emergencies, but require assessment of the patient's condition are processed as Illness Care calls. Illness Care calls make use of automated risk assessment algorithms to help the nurse assess the patient's level of risk. Illness Care calls require verification of the patient's eligibility record in the system. If eligibility records do not exist in the system, you may create a New Patient Chart to add the patient's eligibility record. Illness Care calls are described below.

Provider Selection (F8)

Patient requests for assistance in selecting a provider are processed as Provider Selection calls. Provider Selection calls begun by clicking the Provider Selection button in the Call Type Selection button bar or by pressing F8 require verification of the patient's eligibility record in the system or creation of a New Patient Chart.

However, when an Illness Care call session results in requiring assistance for provider selection, you can perform Provider Selection without passing through the Eligibility Verification window again. Provider Selection calls are described below. Information (F9)

Patient requests for information on self-care and/or insurance rules for a particular plan are processed as Information calls. Information calls require verification of the patient's eligibility record in the system or creating a New Patient Chart Information calls are described below.

Other (F10)

Calls that are inappropriate for the NMS Network Management System software are processed and recorded as Other calls. Other calls are described below.

2 Emergency Call Handling

Select Emergency (F6) from the Call Type Selection button bar (FIG. 8) when the call presents a life-threatening emergency.

The Emergency Handling Window

Click the Emergency button in the Call Type Selection button bar (FIG. 8) or press F6.

The Emergency Handling window (FIG. 10) displays. If the caller's name and telephone number are not already displayed in the Caller Name and Caller Phone boxes as a result of being entered in the Caller Info window, you should record the caller's name and telephone number in the Caller Name and Caller Phone boxes before or after activating emergency procedures.

Caller Name—Type the first and last names of the caller (each separated by a space).

Caller Phone—Enter the caller's telephone number. Use the format: (401) 555-8571.

Assessment of Situation—Enter your assessment of the situation. You may enter this information before or after activating emergency procedures.

OK—When you have activated emergency procedures (such as transferring the call to 911) and have completed entering the information in the Emergency Handling window, indicate completion of the Emergency call by clicking the OK button in Emergency Handling window.

Cancel—If, during the call, you determine the situation is not an emergency, click the Cancel button in the Emergency Handling window. Then at the Call Type Selection button bar, select the appropriate call type to handle the call.

3 Finding, Creating and Viewing Patient Charts

This section contains information on how to find a patient's chart when it already exists in the system, or create a new chart if none exists. The Eligibility Verification window has fields for entering specific information which will locate the chart of a patient who has used the system before.

Eligibility Verification

Your organization may require that you check the patient's eligibility to use the system. If so, Illness Care, Provider Selection, and Information calls require eligibility verification. After initiating one of these call types, the next step is to verify the patient's eligibility status by searching for the patient's records in the database using the Eligibility Verification window.

The Eligibility Verification Window

Click the Illness Care button (F7), the Provider Selection button F8), or the Information button (F9) in the Call Type Selection button bar (FIG. 8).

The Eligibility Verification window displays (see FIG. 11).

If the patient's last name was entered in the Caller Info window (FIG. 7), the patient's last name displays in the Patient Last Name field of the Eligibility Verification window. Otherwise, initiate a search for the patient's records in the system, as follows.

Enter a specific piece of information unique to the patient, such as the patient's social security number in the SSN field, or the Health Plan ID, to narrow the search quickly.

Click the Check Eligibility button or press Esc+F11 to display in the Results box all eligible patients meeting the criteria you have entered so far. In the event the caller cannot give you the correct spelling of the patient's name or does not know the patient's SSN or Health Plan D), try entering additional information in the remaining text boxes to identify the patient. If need be, you can click Check Eligibility or press Esc+F11 to display a list of all eligible patients in the Results box.

When you find the patient listed in the Results box, click the patient's entry (if it is not already highlighted) and then click the OK button, or just double-click the entry, to close the Eligibility Verification window and view the patient's chart.

Patient Last Name—Type the patient's last name if it is not already displayed. Begin the name with a capital letter. If you are unsure of the spelling, use the wildcard search characters.

Patient First Name—Type the patient's first name if it is not already displayed. Begin the name with a capital letter.

Health Plan—Type the name of the patient's (or sponsor's) health insurance plan.

Health Plan ID—Type the patient's identification number for the health insurance plan entered in the Health Plan box. This number will be the number on the patient's health insurance ID card.

Social Security Number—Type the social security number of the patient's (or sponsor's social security number when appropriate). Use the format 123-45-6789.

Sponsor's Employer—Type the name of the employer when the employer is a client of the system.

Note: The entry in the Sponsor's Employer box is only helpful for checking eligibility.

Patient Zip Code—Type the five-digit zip code for the patient's address. Use the format 12345.

Note: If you type too many or too few digits, or letters rather than numbers, and then click Check Eligibility, the system displays an error message to that effect. You will also get an error message if you type a zip code that the system doesn't recognize. In either case, click OK in the message box to return to the Eligibility Verification window.

Patient Phone—Type the patient's telephone number, beginning with the area code. Use the format: (401) 555-8571.

Check Eligibility—Click or press Esc+F11 when you have entered enough data in the text boxes to cause a reasonable search of the database for the patient. The list of names matching the search criteria will display in the Results box. You do not have to fill in each box to initiate a search.

Results—Displays the list of names matching the search criteria. If no patients are listed in the Results box after you click the Check Eligibility button, a message stating that no patients meet the criteria displays. Click the OK button in the message box, then double-check the accuracy of the Social Security Number entry or other text box entries and try Check Eligibility again before creating a new chart.

OK—When the correct patient is highlighted in the Results box, click the OK button (or double click the patient's name in the Results box instead of using the OK button). The Eligibility Verification window will close and both the Algorithm Selection and the Patient Chart windows will open.

New Patient—This button allows you to create a new patient chart using the New Patient Data Entry window (see FIG. 12). For example, if the patient requesting services has not used the system before, and they are not in your installation's database, the patient will not display as a choice in the Results box. In these cases, you may create a new patient chart by clicking the New Patient button. See below for information on the New Patient Data Entry window.

Always check the Social Security Number text box entry and try the Check Eligibility button again before creating a new chart.

If the patient has used the system before, but a chart cannot be found during eligibility verification, a new patient chart may be created. This situation should almost never occur, and should be noted in the Problem Notebook. See the pertinent section below for information on using the Problem Notebook.

Creating a New Patient Chart

If the patient requesting services has not used the system before, a patient chart may not exist for the patient. Always check the Social Security Number text box entry in the Eligibility Verification window and try the Check Eligibility button again before creating a new chart.

When the patient is not found in the database, create a new patient chart by clicking the New Patient button in the Eligibility Verification window. This will open the New Patient Data Entry window.

Note: If the patient has used the system before, but a chart cannot be found during eligibility verification, a new patient chart may be created. This situation should almost never occur, and should be noted in the Problem Notebook. See the pertinent section below for information on using the Problem Notebook.

Any information entered into the Eligibility Verification search fields during an attempt to find a patient's chart will be transferred to the New Patient Data Entry window.

The New Patient Data Entry Window (FIG. 12)

Click the New Patient button in the Eligibility Verification window.

The New Patient Data Entry window displays.

Fill in as many of the New Patient Data Entry window text boxes as you would like.

Note: The Patient's SSN and the Client boxes must be filled in. If you do not have the patient's social security number, enter a "0" (zero). If you do not have the information for the Client text box, use the default value. If you do not have some of the other information, leave the text box blank.

Press Tab to advance to the next text box, or click on the text box you want to activate. Press Shift+Tab to return to the previous text box.

Last Name—Type the patient's last name. Begin the name with a capital letter.

First Name—Type the patient's first name. Begin the name with a capital letter.

MI—Type the patient's middle name or initial. Begin the name with a capital letter.

Street Address—Type the patient's street address.

City, State—The city and state are filled-in automatically after you enter the zip code.

Zip Code—Type the patient's 5-digit zip code. Use the format 12345.

Note: If you type too many or too few digits, or letters rather than numbers, and then click Check Eligibility, the system displays an error message to that effect. You will also get an error message if you type a zip code that the system doesn't recognize. In either case, click OK in the message box to return to the New Patient Data Entry window to make a correction.

Phone—Type the patient's telephone number, beginning with the area code. Use the format: (401) 555-8571.

Date of Birth—Type the patient's date of birth in the format: 15-mar-94 (the month in all lower case letters).

Gender—Click the list button, then click the appropriate choice in the list.

Ethnic Origin—Click the list button, then click the appropriate choice in the list.

Marital Status—Click the list button, then click the appropriate choice in the list.

Patient's SSN—The patient's social security number must be entered If the social security number is not known, type "0" (zero). Use the format 555-14-2857.

Sponsor's Employer—Type the name of the policyholder's employer.

Client—The name of the client must be entered. If the correct client for your installation is already displayed, you may just press the Tab key to advance to the next text box. Otherwise, click the list button, then click the appropriate client in the list.

Plan Name—Click the list button and select a plan from the predefined list, or type the name of the plan if it does not appear on the list.

Plan Type—Click the list button and select a plan type from the predefined list, or type the name of the plan type if it does not appear on the list.

Health Plan ID—Type the patient's identification number for the health insurance plan. This number will be the number on the patient's health insurance ID card.

Primary Physician—Type the name of the patient's primary physician. The primary physician you define here for the patient's chart will automatically be changed if an appointment is made with a different provider during a Provider Selection session begun for Administrative Reasons. This entry is also used in the Provider Selection function if the physician is defined as a provider in the database.

OK—Click the OK button to record the new patient chart and leave the New Patient Data Entry window. The New Patient Data Entry window disappears and the Patient Chart window displays with the newly created patient information.

Note: If a message stating the social security number you entered in the Patient's SSN text box already exists in a patient chart:

Click the OK button in the message window.

Click the Cancel button in the New Patient Data Entry window.

Type the correct social security number in the Social Security Number text box in the Eligibility Verification window.

Click the Check Eligibility button in the Eligibility Verification window.

Click the OK button in the Eligibility Verification window to bring up the patient's chart.

You may now proceed with the rest of the call session (Illness Care or Information). See the section Viewing Patient Charts for information on the Patient Chart window.

Cancel—Click the Cancel button to stop creating a new patient chart and return to the Eligibility Verification window. Any information you entered into the New Patient Data Entry window is lost when you click the Cancel button.

Viewing Patient Charts

The Patient Chart window (see FIG. 13) is for viewing information on file for the patient. You can use the buttons in this window to toggle between the various types of chart information available.

Note: You cannot update the patient's chart from the Patient Chart window. Only the Nurse Administrator can update a patient's chart. If you need to update information in the patient's chart, make a note in the Problem Notebook containing the new information. See the pertinent section below for information on using the Problem Notebook.

The Patient Chart Window (FIG. 13)

Click on a patient's name in the Results box of the Eligibility Verification window and then click OK; or, Double-click on a patient's name in the Results box of the Eligibility Verification window.

Click the OK button after completing a new patient chart.

Once a patient's name is selected from the Eligibility Verification window, or a new patient chart is created, the Patient Chart window displays the identifying information available for the patient in the scrolling text box of the Patient Chart window.

Identifying Information—The identifying information for the patient displays in the Patient Chart window when the Patient Chart window first opens (as shown in FIG. 13). After another type of information has been displayed by clicking one of the other buttons in the Patient Chart window, you can return to the identifying information display by clicking the Identifying Information button in the Patient Chart window.

Health Information—Clicking the Health Information button in the Patient Chart window displays the information shown in FIG. 14.

Figure 15:
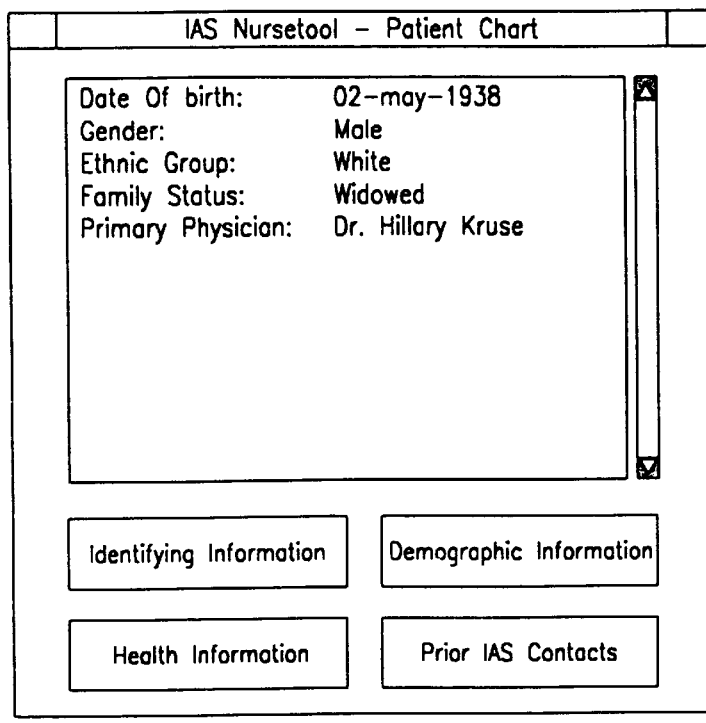

Demographic Information—Clicking the Demographic Information button in the Patient Chart window displays the information shown in FIG. 15.

Figure 16:
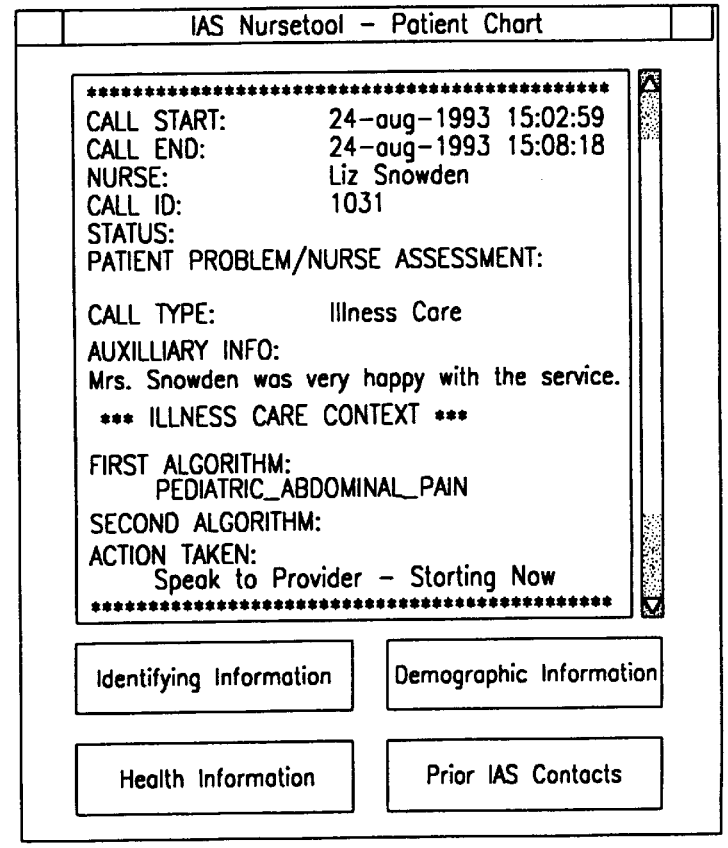

Prior NMS Contacts—Clicking the Prior NMS Contacts button in the Patient Chart window displays the information shown in FIG. 16. The most recent call record is displayed first. To review older call records, use the scroll bar to page down in the display.

Minimizing the Patient Chart Window

You may minimize the Patient Chart window to an icon if desired.

Click the close box in the top-right corner of the window.

The Patient Chart window will be minimized to an icon at the bottom of the computer screen (FIG. 17).

Opening the Patient Chart Window Icon

You may open the Patient Chart window from its icon if desired.

Double-click the Patient Chart icon at the bottom of the computer screen.

The Patient Chart window displays.

4. Illness Care

At the heart of the NMS Network Management System is a set of decision trees, or algorithms, enabling you to sort patients into different risk categories without requiring a medical diagnosis. With these algorithms, you can query the caller for answers to specific questions related to the patient's presenting symptoms. The algorithms branch to predefined actions based on the answers received, so that patients can be guided to an appropriate level and type of care for their problems based on their level of risk and potential needs.

The NMS clinical algorithms are not intended to develop medical diagnoses; they do establish temporal urgency requirements and recommend level of intervention required for evaluating a caller's problem. While the Illness Care call process is relatively structured, it is designed for use by registered nurses who can override the recommendations of the system based on their professional nursing judgment.

After you receive a call, select Illness Care from the Call Type Selection button bar (FIG. 8), and find or create the patient's chart, the system will bring you to the Algorithm Selection window (FIG. 18).

The Algorithm Selection Window

Click the OK button in the Eligibility Verification or in the New Patient Data Entry window.

The Algorithm Selection window displays (see FIG. 18).

The Algorithm Selection window offers alternative methods for finding the best algorithm to use when you are interviewing the patient. The alternatives are described below.

Topical Listing—Eleven buttons are available for choosing a category of algorithms. Click the Topical Listing button for the medical category that best describes the patient's symptoms. When you have selected a medical category, a list of the algorithms within that category displays in the Alphabetical Listing box.

Alphabetical Listing—Initially, this box displays an alphabetical list of all algorithms in the system. When you click on a medical category (one of the Topical Listing buttons), or enter keywords into the Keywords box, the list in the Alphabetical Listing box is narrowed to the algorithm (s) corresponding to the medical category you clicked and the keywords you entered.

Figure 19:
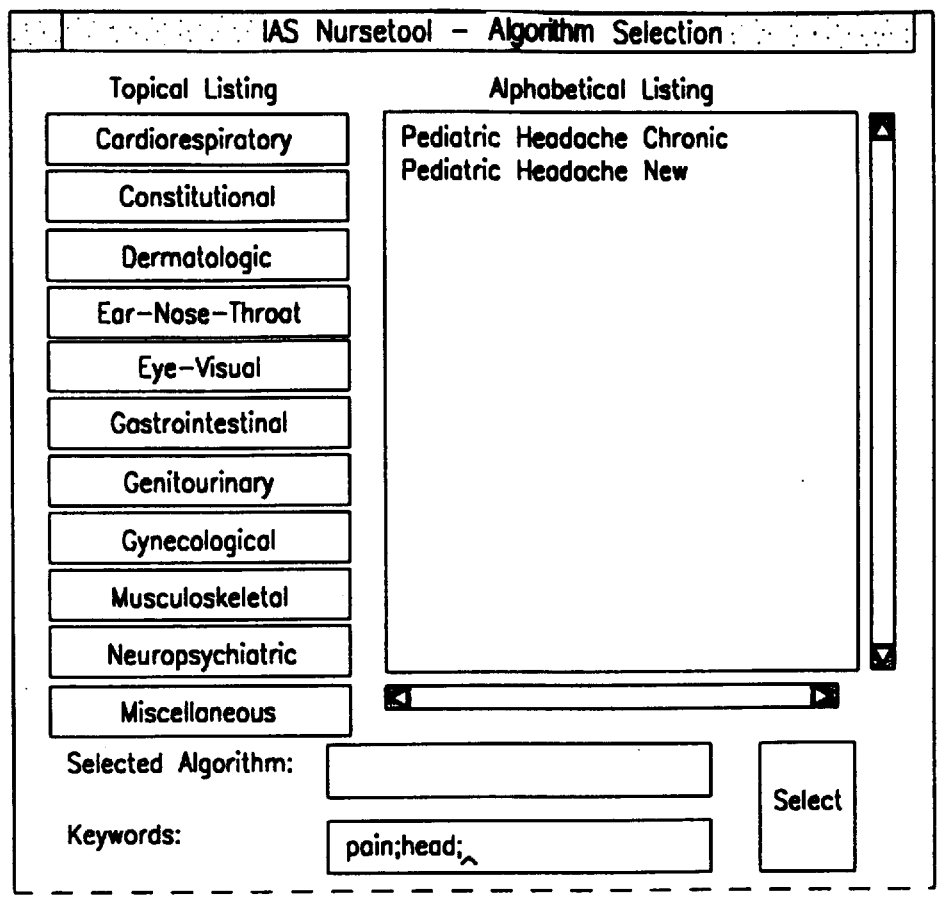

Keywords—The Keywords text box allows you to find an algorithm by typing in keywords that describe the patient's symptom(s). Each keyword—including the last—must be followed by a semicolon (;). As soon as you type the semicolon, the related algorithms will be listed in the Alphabetical Listing list box. An example of the list associated with the keyword "pain;" is shown in FIG. 19. Multi-word keywords must be connected by a hyphen (-). Abbreviations may be use &

Note: If you clear the Keywords text box with the Backspace key, the full list of algorithm displays in the Alphabetical Listing box.

Associated Algorithm—After clicking on an algorithm in the Alphabetical Listing box, this scrolling list box displays the names of the algorithm, together with their purposes, that are similar to the algorithm you chose, as a way to double-check that you are selecting the most appropriate algorithm.

If an associated algorithm describes the patient's symptoms better than the algorithm in the Selected Algorithm box, click on the more appropriate algorithm name in the Associated Algorithm box. The name you select displays in the Selected Algorithm box. The purpose of the algorithm you selected displays in the Purpose of Selected Algorithm box.

Figure 20:
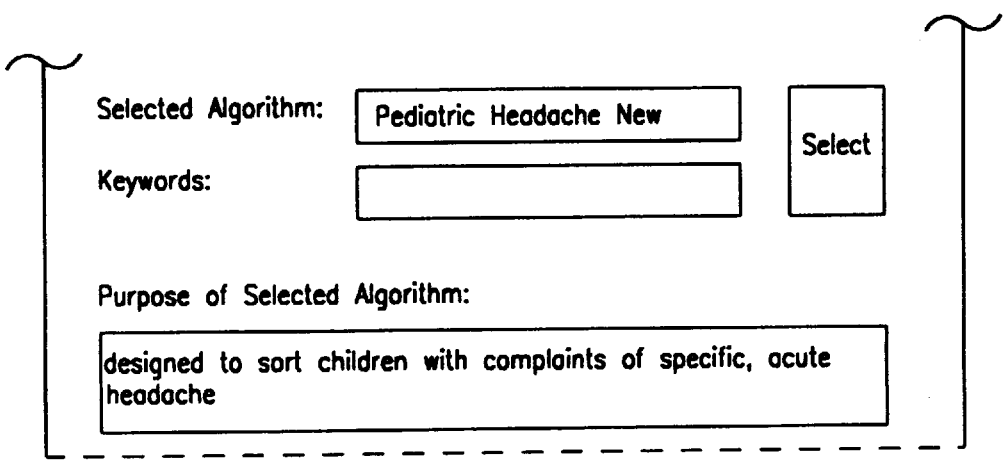

Selected Algorithm—When you click on an algorithm in the Associated Algorithm box, the name of the algorithm displays here. See FIG. 20.

Purpose of Selected Algorithm—When the name of an algorithm displays in the Selected Algorithm box, the purpose of that algorithm displays in this box.

Figure 21:
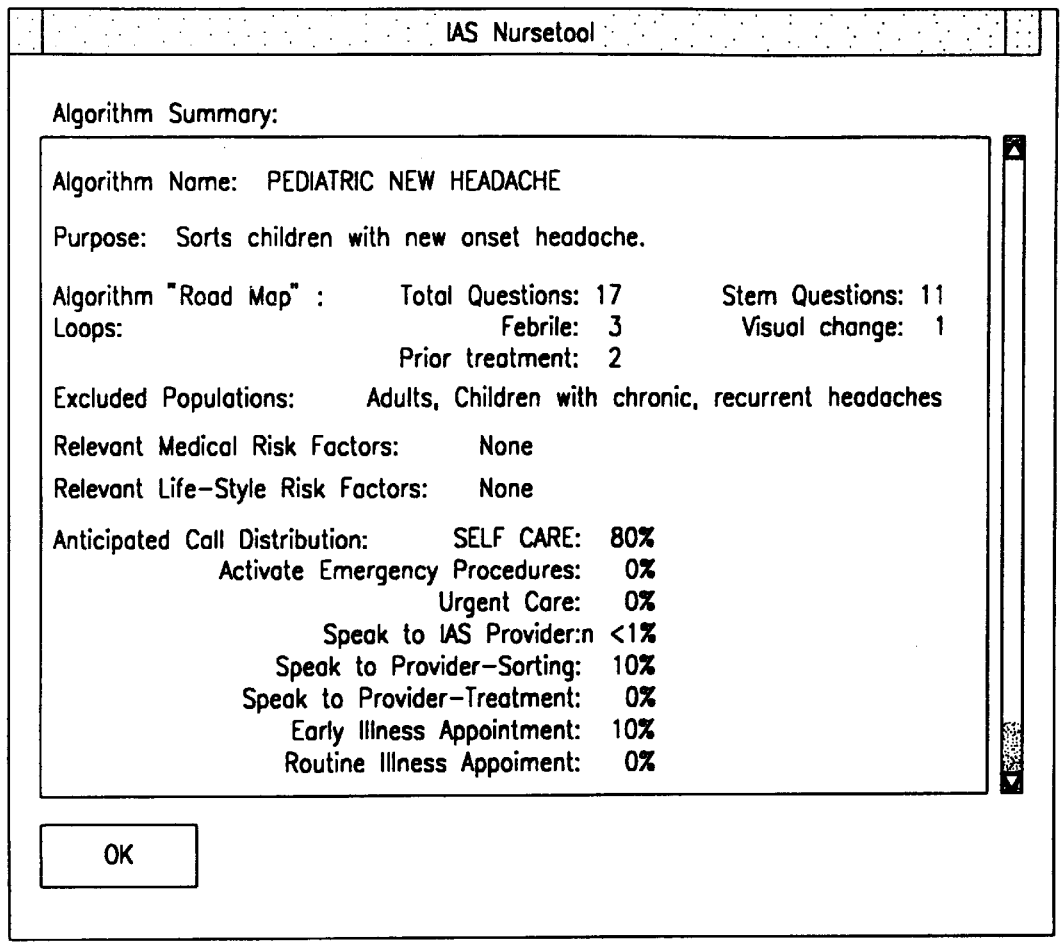

Select—When you are satisfied that the item displayed in the Selected Algorithm box most closely corresponds to the patient's problem, click the Select button to advance to the Algorithm Summary window (FIG. 21) as follows.

Click the Select button to advance to the Algorithm Summary window; or

Double—click on an item in the Alphabetical Listing box to advance to the Algorithm Summary window.

The Algorithm Summary Window

The Algorithm Summary window contains a detailed overview of the selected algorithm inside a display—only scrolling text box.

Click the Select button in the Algorithm Selection window; or

Double-click on an item in the Alphabetical Listing box of the Algorithm Selection window (FIG. 18).

OK—Once you have reviewed the summary, click the OK button to close the Algorithm Summary window and to proceed with the first question of the algorithm. If no algorithm summary exists, a message window displays in place of the Algorithm Summary window. Click the OK button in the message window to proceed with the first question of the algorithm.

Algorithm Navigation

Algorithm navigation takes place in the Algorithm Navigation window (FIG. 22).

The Algorithm Navigation window presents clinical questions together with supporting lay questions. The answers to the clinical questions move you through the algorithm until you reach a list of actions.

The algorithm navigation process requires you to record the caller's answers to the questions presented in the Algorithm Navigation window. As soon as you select the button that represents the caller's answer to the question, the system will present another series of questions or advance to the Nurse Action List window.

The Algorithm Navigation Window

Algorithm Name—This box displays the name of the algorithm from which questions are currently being asked. If a transfer to another algorithm takes place (e.g., a patient complaining of back pain also has chest pain and the system transfers to the Chest Pain algorithm), the name of the new algorithm displays.

Clinical Question—Describes the current question in clinical terminology. Clinical questions are always yes/no questions.

Lay Question—Provides suggestions for how the clinical question can be asked in language more appropriate for most callers. The lay questions may not necessarily be yes/no questions, but are intended to solicit the information the nurse needs to answer the clinical question.

Rationale—Describes the reasoning for asking the current question, and may present an explanation if the patient answers yes to the current question.

Yes—Click the Yes button or press Control+Y when the caller answers "yes" to the question.

No—Click the No button or press Control+N when the caller answers "no" to the question.

Unsure—When the caller cannot give a definite answer to the question, click the Unsure button or press Control+U to see a further discussion about the question.

Figure 23:
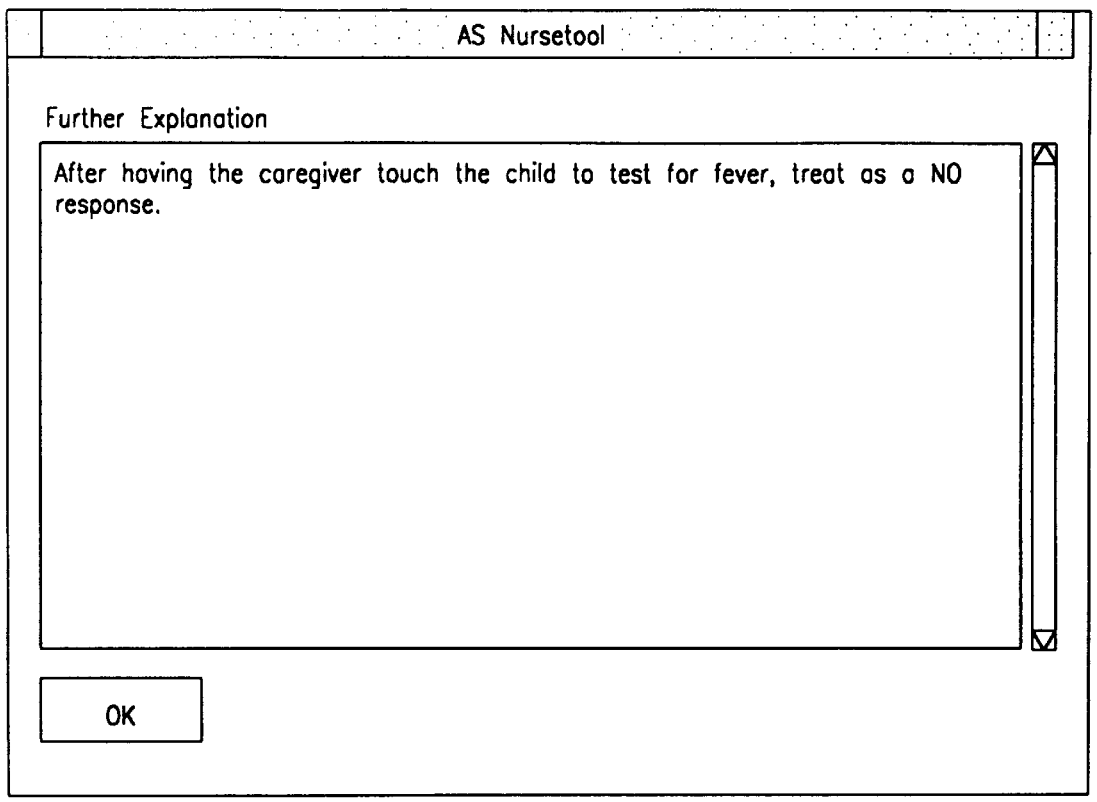

The Further Explanation window displays (see FIG. 23).

Navigation window

Click the OK button in the Further Explanation window to close it and proceed with the algorithm navigation process.

Back—Click the Back button or press Control+B to back up and erase the previous answer and continue from the previous question.

Comments—This space is provided to record any comments you may wish to make about the patient or the response to the question. Text entered into the Comments box is only saved with this question in the call record when you click the Insert button.

Insert—Click the Insert button to save a comment you entered into the Comments text box. Once you insert a comment, it becomes a permanent part of the record of the current call and the comment cannot be deleted.

Erase—Click the Ease button to remove a comment from the Comments box before clicking the Insert button. Once inserted, comments cannot be deleted Nurse Action List Algorithm navigation for the call is completed when the Nurse Action List window (FIG. 24) displays. The Nurse Action List window presents a list of recommended actions to address the patient's condition. Depending on the action that you select, a different window will display.

Possible Recommended Actions

The possible actions are listed below in order of their medical priority:

Activate Emergency Procedures—For potentially life-threatening emergencies requiring on-site or en-route care.

Speak to IAS Provider—For possible need for EMS dispatch. A physician interview may identify a more appropriate action.

Urgent Care—For care needed now, but EMS care on-site or en-route is not needed. Care could be delivered in the emergency room, clinic, or doctors' offices.

Transfer to Algorithm—For transferring to the Algorithm Navigation window to navigate through a different algorithm.

Speak To Provider—Sorting—For possible need for a provider visit A physician interview may identify whether action is needed now (ASAP) or later (can be delayed for up to four hours).

Speak To Provider—Treatment—For a physician interview to identify whether appropriate care can be initiated by phone.

Early Illness Appointment—For an appointment with an appropriate provider "the next time the office is open."

Routine Illness Appointment—For scheduling an appointment within two weeks.

Self-Care—For problems which can safely be treated at home.

The Nurse Action List Window

The Nurse Action List window displays automatically after completion of the Algorithm Navigation.

The top scrolling text box in the Nurse Action List window displays a list of recommended actions, prioritized by the system according to the order above. Usually, you will select the top-most action in the list You may override the most highly recommended action and select another action that, in your judgement, is appropriate to address the patient's condition. Reasons for such overrides should be noted in the comments section of the Call Termination window.

Highlight an action by clicking on it. Information displays in the boxes described below. The contents of these boxes change depending on which action is selected.

Click the Select button.

Select—When the action you want is highlighted (click on the action to highlight it), click the Select button to display the action's endpoint window.

Clinical Rationale—An explanation of why the highlighted action is recommended.

Message to Patient—Suggested language to use to explain the recommendation to the patient.

Symptom Pattern—What the patient said to cause the system to generate this recommendation.

Need to Consider—A clinical description of what conditions cannot safely be ruled out. When appropriate, this information will be passed on to the doctor.

Provider Codes—This box contains the criteria for selecting an appropriate provider when you perform Provider Selection.

Done—After you are done with Illness Care, click Done to exit algorithm navigation. A message will display asking if you are sure you want to end the medical assessment procedure. If you click Yes in the message window, both the Algorithm Navigation window and the Nurse Action List window close. If you click No in the message window, the Nurse Action List will remain displayed.

Cancel—Click Cancel to return to the Algorithm Navigation window (FIG. 22). The effects of selecting one of the possible endpoints presented in the Nurse Action List window are shown in FIG. 25.

Patient Self Care

When you select ACCESS SELF CARE INSTRUCTIONS from the Nurse Action List, the system presents instructions for self care in the Self Care End Point window (FIG. 26).

The Self Care End Point Window

Instructions—The Instructions scrolling text box contains information organized into four categories:

General Information and Education

Instructions for Pain/Symptom Relief

Watch Out For/Call Us Back For

Callback Instructions

Use this information to instruct the caller in understanding, accepting and carrying out self care.

Does the Patient Accept—Click the appropriate radio button. If the patient does not accept the recommended action, clicking the No radio button and then clicking the OK button will close the Self Care End Point window and reopen the Nurse Action List window, where you may select a different action.

Callback Date—If you determine a callback to the patient is appropriate, type the scheduled callback date using the format: 01-apr-94. This information will be presented in the Worklist window.

Note: The month must be the first three letters of the month in all lowercase letters.

Callback Time—Type the scheduled callback time using the format: 14:00 (the system uses a 24-hour clock).

End Point Disposition—Click in the text box and type comments or concerns from the patient regarding self care, if any, or any comments pertinent to the callback because this information will be displayed in the Worklist window at the time of the callback.

OK—Click the OK button to close the Self Care End Point window. Note: If you haven't filled in the Caller Name and Phone boxes in the Caller Info window, an error message will be presented telling you to do so.

Cancel—Click the Cancel button at the bottom right corner of the window to close the Self Care End Point window, return to the Nurse Action List window, and select a different action.

Other End Points

This section describes more end points available as actions in the Nurse Action List window.

Early Illness Appointment

Assist the caller in establishing an appointment with an appropriate provider. Most often this will be an appointment within 48 hours. However, a call late Friday evening, for example, might result in an appointment Monday morning. If you select the Early Illness Appointment end point and the Provider Selection function is available on your system, the Do you want to perform Provider Selection? message window displays.

Routine Illness Appointment

Assist the caller in establishing a routine appointment with an appropriate provider.

The appointment should be no later than two weeks from the date of the call. If you select the Routine Illness Appointment end point and the Provider Selection function is available on your system, the Do you want to perform Provider Selection? message window displays.

Urgent Care

Use when the patient needs care now, but does not need EMS care on-site or en-route. If you select the Urgent Care end point and the Provider Selection function is available on your system, the Do you want to perform Provider Selection? message window displays.

Activate Emergency Procedures

When you select ACTIVATE EMERGENCY PROCEDURES from the Nurse Action List, the Emergency Handling window displays. (See Section 2: Emergency Call Handling above). Follow the emergency procedures established at your installation.

Use this action when there is a reason to suppose the need for on-site and en-route care beyond the capabilities of the typical caregiver.

Transfer to Algorithm

When you select TRANSFER TO ALGORITHM from the Nurse Action List, the Algorithm Navigation window (FIG. 22) for the new algorithm opens. (See Algorithm Navigation above.)

Speak To NMS Provider

Connect the caller to a supervising physician who will complete the triage encounter.

Use this action when a possible need for emergency medical services exists, but a physician interview may identify more appropriate actions.

When SPEAK TO NMS PROVIDER is the recommended action and you click the Select button in the Nurse Action List window, the Speak With NMS Provider window (FIG. 27) displays:

Provider Name—Type the name of the doctor the caller will speak to, or select a name using the list button to display a list of provider names.

Provider Comments—Type any comments the made by the doctor.

Recommendation—Use the list button to enter the doctor's recommendation.

Depending on the recommendation, the call may continue with Provider Selection if the Provider Selection function is available on your system.

Does the Patient Accept?—Click the appropriate radio button indicating whether the patient accepts the doctors recommendation.

OK—Click the OK button to conclude the illness care process. If the No radio button is selected, clicking the OK button will return you to the Nurse Action List where you may select a different action.

Cancel—Click the Cancel button to return to the Nurse Action List and select another action.

Speak To Provider—Treatment

Assist the caller in speaking with a doctor who will decide whether appropriate care can be initiated by telephone with follow-up care by appointment. This doctor can be the patient's primary care physician, the physician covering for the patient's primary care physician, or a doctor in the employ of the patient's insurance carrier. Clicking the OK button opens the Speak With Provider window.

When SPEAK TO PROVIDER is the recommended action and you click the OK button in the Nurse Action List window (FIG. 24), the Speak With Provider window (FIG. 28) displays:

Provider Name—Type the name of the provider the patient will consult.

Does the Patient Accept?—Click the appropriate radio button indicating whether the patient accepts the doctor's recommendation.

OK—Click the OK button to conclude the illness care process. If the No radio button is selected, clicking the OK button will return you to the Nurse Action List where you may select a different action.

Cancel—Click the Cancel button to return to the Nurse Action List and select another action.

Speak To Provider—Sorting-Now/Later

Assist the caller in speaking with a doctor who will determine the appropriate next step in the patient's care. This doctor can be the patient's primary care physician, the physician covering for the patient's primary care physician, or a doctor in the employ of the patient's insurance carrier.

The algorithm designates that this contact occur either "now" or "later". The "now" designation means that the caller should speak to the doctor as soon as possible. The "later" designation means that the contact can be delayed for up to four hours. Clicking the OK button opens the Speak With Provider window (see FIG. 28) described above.

5 Handling Requests for Information

Callers may request information on self care and/or rules for a particular health plan. This will be an Information call type. Information calls require eligibility verification prior to access to medical or health plan information.

Information Calls

Use the Information button in the Call Type Selection button bar (FIG. 8) to handle Information calls, but do not use the Information button in the Call Type Selection button bar to access medical information if you are already processing a call, such as an Illness Care call. Doing so will log the call as an Information call instead of an Illness Care call. If you want to access information without changing the call type and without checking eligibility, use the Medical Information button in the NMS Main button bar (FIG. 6).

Click the Information button in the Call Type Selection button bar or press F9.

The Eligibility Verification window (FIG. 11) displays.

The steps for using the Eligibility Verification window to locate a patient's chart are described in Section 3, Finding, Creating and Viewing Patient Charts.

After the patient chart is found or created, the Information Type Selection window (FIG. 29) displays.

The Information Type Selection Window

The system groups requests for information into two categories:

Medical Information

Health Plan Rules

You must select one of these categories from the Information Type Selection window.

After clicking the Information button in the Call Type Selection button bar and selecting a patient in the Results box of the Eligibility Verification window, click the OK button in the Eligibility Verification window.

The Information Type Selection window displays.

The Information Type Selection window includes two radio buttons:

Medical Information—Click the Medical Information radio button and then click the OK button to advance to the Self Care Selection window.

Health Plan Rules—Click the Health Plan Rules radio button and then click the OK button to advance to the Health Plan Rules Selection window.

OK—After selecting the radio button that corresponds to the requested information type, click the OK button to advance to the next window.

Cancel—Click the Cancel button to stop the Information type of call. Clicking the Cancel button closes the Information Type Selection window.

Medical Information

When you choose Medical Information from the Information Type Selection window, the Self Care Selection window (FIG. 30) displays. The Self Care Selection window allows you to choose the particular self care information to retrieve. The Self Care Selection window, which is very similar to the Algorithm Selection window (FIG. 18), allows selection of a self-care instruction based on a medical category and provides a way to search for self care instruction using keywords.

The Self Care Selection Window

The Self Care Selection window displays when you click the Medical Information radio button and then click the OK button in the Information Type Selection window.

Topical Listing—Click on the medical category that best describes the caller's request for information. A list of the corresponding self-care instructions displays in the Alphabetical Listing box.

Alphabetical Listing—Initially, the Alphabetical Listing scrolling list box displays a list of all self-care instructions in the system. When you click on a medical category using one of the Topical Listing buttons, or enter keywords into the Keywords box, the list is narrowed to display the self care instructions that correspond to the medical category or keywords.

Figure 31:
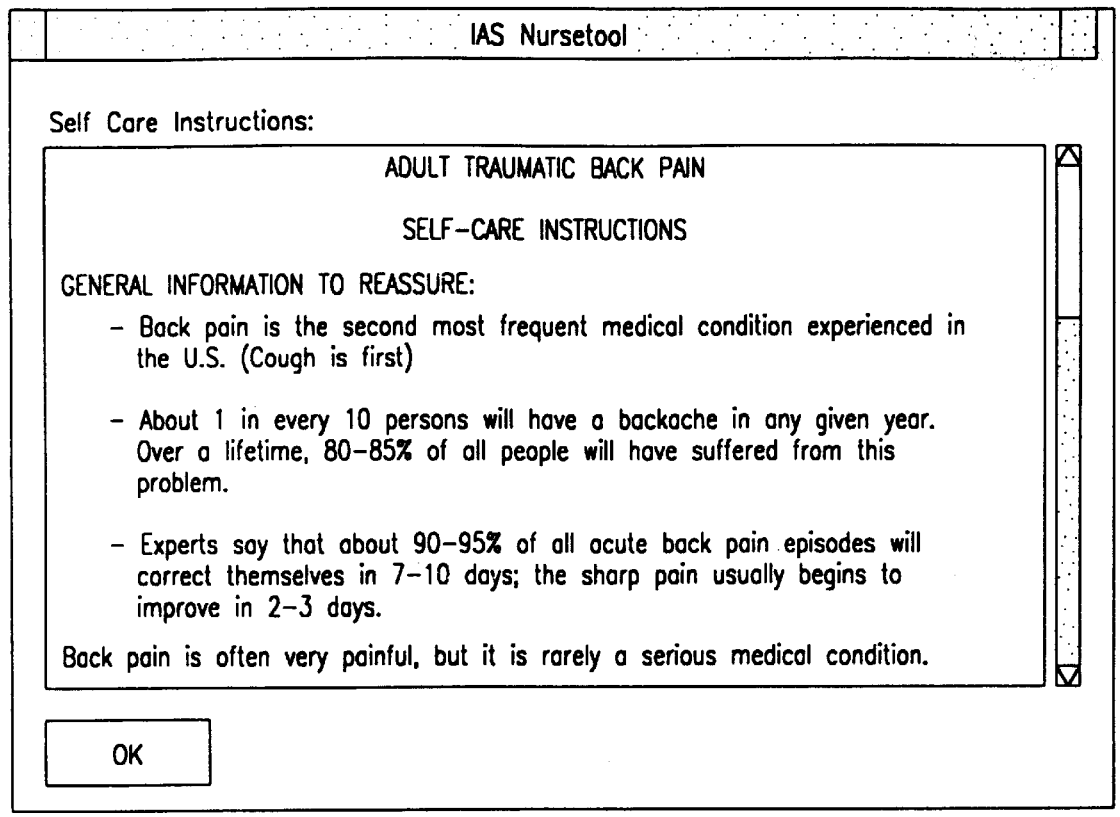

You can double-click on an item in the Alphabetical Listing box to advance to the Self Care Instructions window (FIG. 31).

Selected—This box displays the currently selected self care instruction item.

Keywords—Find a self care instruction by typing keywords that describe patient's request for information. Each keyword—including the last—must be followed by a semicolon (;).

Select—When you are satisfied that the item displayed in the Selected box corresponds to the patient's request for information, click the Select button to advance to the Self-Care Instructions window.

Note: Double-clicking on an item in the Alphabetical Listing box has the same effect as clicking the Select button.

The Self Care Instructions Window

The Self Care Instructions window displays when you click the Select button or double-click on an item in the Alphabetical Listing box in the Self Care Selection window.

Self Care Instructions—This is a display-only scrolling text box with the instructions corresponding to the self care item selected from the Self Care Selection window.

OK—Click the OK button to exit the Self Care Instructions window when you are finished offering self care instruction to the caller. You may then either select another call type from the Call Type Selection Bar (see FIG. 8), or select Stop Call from the NMS Main button bar (see FIG. 6).

Health Plan Rules

Figure 32:
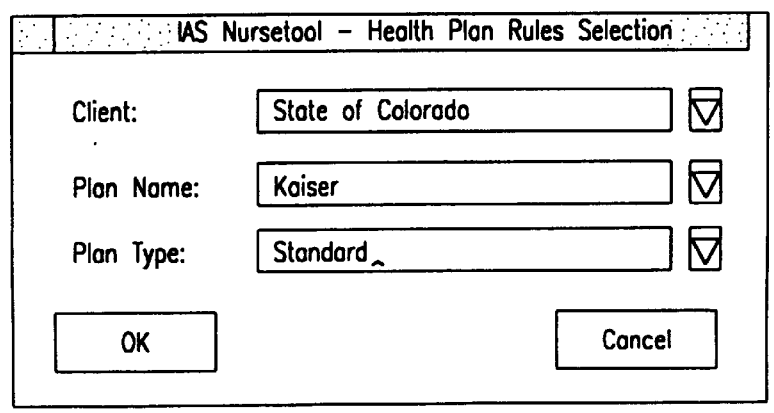

When you choose Health Plan Rules from the Information Type Selection window, a Health Plan Rules Selection window (FIG. 32) displays. The Health Plan Rules Selection window contains three pull-down list boxes to select the information you wish to search for in order to answer the caller's request for information.

The Health Plan Rules Selection Window

The Health Plan Rules Selection window displays when you click the Health Plan Rules radio button and then click the OK button in the Information Type Selection window If the patient's chart does not contain information for the Client, Plan Name, and Plan Type boxes, these three boxes will be blank when the Health Plan Rules Selection window displays. To proceed, enter the information in the boxes, as described below.

Client—The client currently associated with the patient is defined here. To add or change clients, click the list button to display a predefined list of clients. Scroll until the appropriate client name is highlighted and release the mouse button; or type the requested client into this box.

Plan Name—The patient's current plan name is defined here. To add or change plan names, click the list button, then select the plan name from the predefined list, or type the requested plan name into this box.

Plan Type—The patient's current plan type is defined here. To add or change the plan type, click the list button, then select the plan type from the predefined list, or type the requested plan type into this box.

Figure 33:
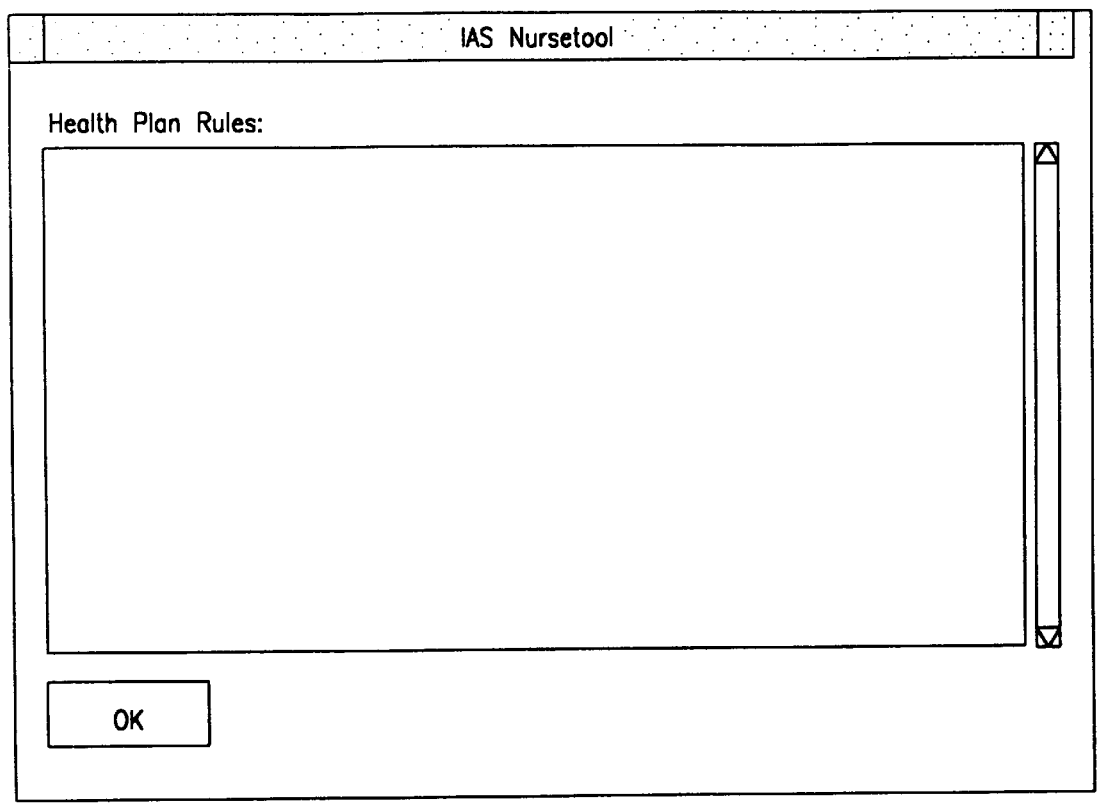

OK—Click the OK button to display the requested information in the Health Plan Rules window (FIG. 33).

Cancel—Click the Cancel button to cancel a request for insurance rules information and close the Health Plan Rules Selection window.

The Health Plan Rules Window

The Health Plan Rules window displays when you click the OK button in the Health Plan Rules Selection window.

Health Plan Rules—This is a display-only scrolling text box containing the requested health plan rules information.

Note: If no health plan rules are available for the plan you selected in the Health Plan Rules Selection window, a message window may display. Click the OK button in the message window to continue.

Click the OK button to close the Health Plan Rules window.

6 Other Calls

In addition to the Emergency, Illness Care, Provider Selection and Information call types discussed in other sections, the NMS Network Management System provides for handling calls that are inappropriate for the NMS software. These calls are processed as Other calls.

Click the Start Call button in the NMS Main button bar (FIG. 6) or press F1 to display the Call Type Selection button bar (FIG. 8).

Handling Inappropriate Calls

Figure 34:
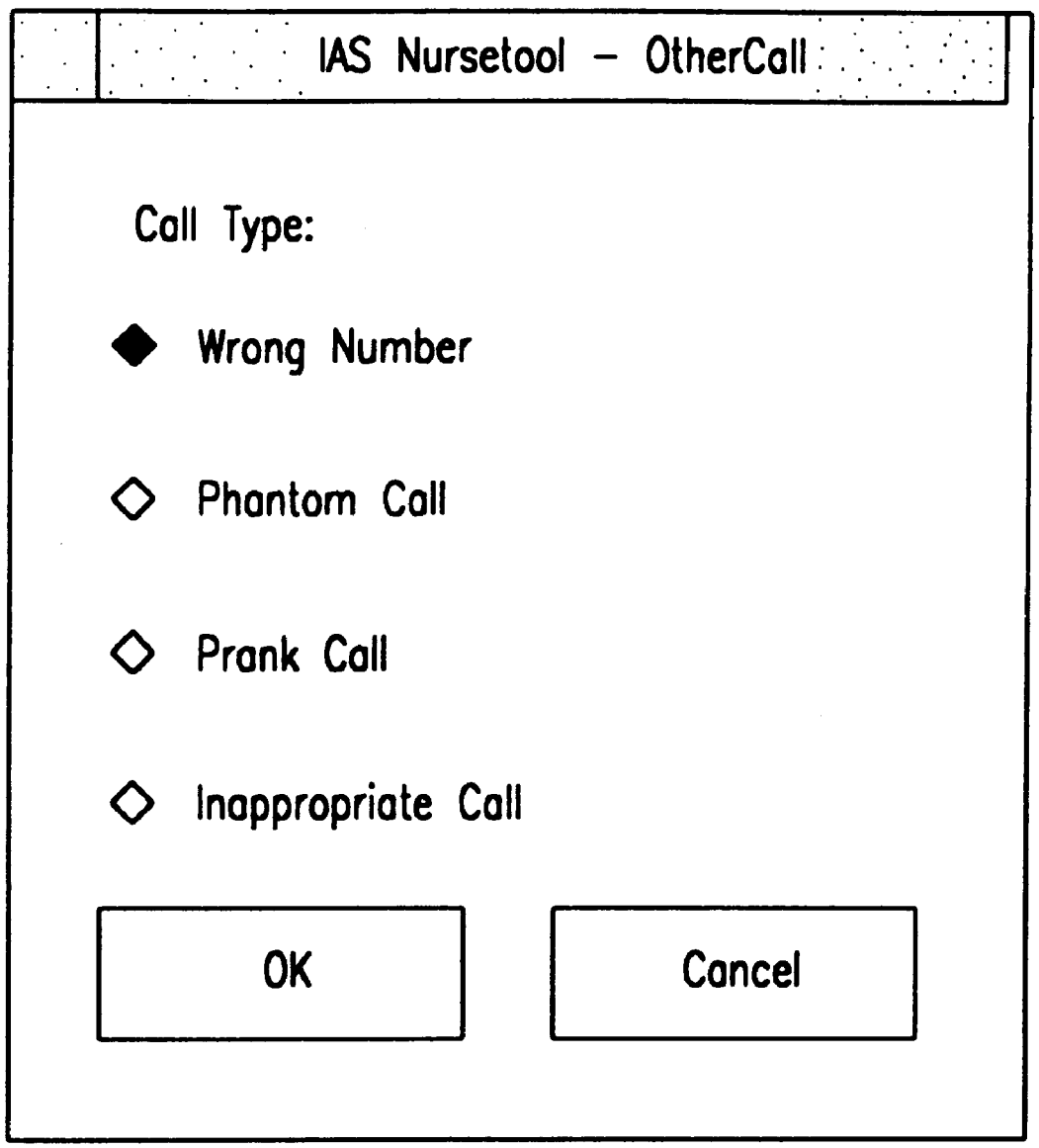

When you receive an invalid call (e.g., wrong number, prank call etc.), select the Other (F10) button in the Call Type Selection button bar to display the OtherCall window (FIG. 34).

The OtherCall Window

Click the Other button in the Call Type Selection button bar or press F10.

The OtherCall window displays.

The OtherCall window contains a series of radio buttons to indicate types of inappropriate calls.

Click the radio button that best describes the call:

Wrong Number—Click this radio button if the caller simply dialed the wrong number.

Phantom Call—Click this radio button if nobody is on the other end of the line.

Prank Call—Click this radio button if the caller did not call for serious business, including obscene calls.

Inappropriate Call—Click this radio button if the caller's request was inappropriate to the NMS Network Management System, but not described by the previous three options.

OK—Click the OK button to record the information and leave the OtherCall window.

Cancel—Click the Cancel button if you determine that the call is appropriate after all and you want to return to the Call Type Selection button bar to select a different call type.

7 Terminating a Call

After the caller has been served, the NMS Network Management System provides a means to collect information about the utility and effectiveness of the system.

The Call Termination Window

Click Stop Call in the NMS Main button bar or press F2 to open the Call Termination window (FIG. 35).

The Call Termination window displays.

Termination—Click the Normal radio button if the call session was successful.

Click the Abnormal radio button if the call session was terminated before the normal processing was accomplished.

What would patient have done if this service were not available?—Click the appropriate radio button.

Sought emergency care—Click this radio button if you believe the patient would have sought Emergency Handling.

Made appointment with physician—Click this radio button if you believe the patient would have set up an appointment to see a physician.

Attempted self care—Click this radio button if you believe the patient would have tried Self Care.

Other—Click this radio button when none of the other radio buttons in this set seems appropriate, and enter comments in the text box. The comments entered in this text box will be saved with the data for the call when you click the Done button.

Tag for rapid retrieval?—Click the Yes or the No radio button, depending on whether the call session warrants further attention.

Indicate Reason—Click the appropriate check boxes if you clicked the Yes radio button for Tag for rapid retrieval?.

The call involved a potential lifesaving intervention

The call involved a potential savings of medical costs

The call was a noteworthy example of service value

This was a problematic call—may require follow-up

Comments—Enter any comments you have about the call session.

Note: These comments will be displayed in the Patient Chart IAS Call Summary Report Done—Click the Done button when you have finished with the Call Termination window.

The Call Termination window will close and the call session will end.

8 Problem Notebook

The Problem Notebook is a repository for problems you may encounter using the NMS Network Management System, or problems with the medical assessment process.

In addition, you should use the Problem Notebook to record instances when the patient has used the system before, but a patient chart cannot be found during eligibility verification, or when a patient chart is inaccurate.

The Problem Notebook can be used at any time before, during or after the call process.

The Problem Notebook Window

Click the Problem Notebook button in the NMS Main button bar (FIG. 6) or press F4.

The Problem Notebook window (FIG. 36) displays.

Entering Problems into the Problem Notebook

Any user may enter a problem in the Problem Notebook.

Clear—Click the Clear button to clear any information displaying in the Problem Description box.

Problem Type—Choose from Medical Problem or System Problem using the list button. A Medical Problem relates to the medical information available for the call; a System Problem relates to a problem with the NMS software.

Priority—Choose from Enhancement, Minor, Medium, Major, or Fatal using the list button. A description of each Priority type is as follows:

| Values in Priority text box | Items in Priority list box |
| --- | --- |
| Enhancement | An increase or modification in the system functionality. |
| Minor | The system can still be used because the functioning of the system is not significantly impaired by the problem. |
| Medium | A workaround is available for this functional problem, but increased effort is required by some or all users. |
| Medium | Basic functionality is seriously affected by this problem and manual intervention is required. |
| Fatal | The entire system is affected, so a fix is required immediately. |

Problem Description—Click in the Problem Description box and type your description of the problem or enhancement. Be as specific as possible in your description of a problem, i.e., how it occurred.

Insert—Click the Insert button at the bottom center of the window to insert the problem into the Problem Notebook.

OK—Click the OK button to record the information you entered and return to the window that was displayed before you opened the Problem Notebook window.

Cancel—Click the Cancel button to exit the Problem Notebook without recording any information.

Reviewing a Problem in the Problem Notebook

Any user may review a problem in the Problem Notebook.

Select the appropriate search criteria to locate the problem you are interested in reviewing.

Select By—When you wish to review a problem, use the Select By list button to find problems by:

Today's Date
User
Status
Problem Type
Priority

Select Key—After choosing a search category using the Select By list button, use the Select Key list button to choose the criteria for the search.

The contents of the Select Key list box change depending on what is currently selected in the Select By box (see the following table).

| Values in Select By text box | Items in Select Key list box |
| --- | --- |
| User | Only the Nurse Administrator can view all user's problem descriptions. |
| Today's date | The current date |
| Status | Open |
|  | Resolved |
| Problem Type | System Problem |
|  | Medical Problem |
| Priority | Enhancement, Minor, Medium |
|  | Major, Fatal |

The problems that match the Select By and Select Key values will be listed in the top display-only scrolling list box.

Problem List—This box contains a list of problems already entered into the system. Click on an item in the list to view its description in the Problem Description text box; its status in the Status box; information concerning its resolution, if resolved, in the Problem Resolution text box; and who resolved the problem in the Resolved By box.

OK—Click the OK button to return to the window that was displayed before you entered the Problem Notebook.

Cancel—Click the Cancel button to exit the Problem Notebook.

Resolving a Problem in the Problem Notebook

The Nurse Administrator can update the Problem Notebook when:

A problem has been resolved.

The Problem Type changes.

The Priority of a problem changes.

Select the appropriate search criteria

Select By—When you wish to review a problem, use the Select By list button to find problems by:

Today's Date
User
Status
Problem Type
Priority

Select Key—After choosing a search category using the Select By list button, use the Select Key list button to choose the criteria for the search.

The contents of the Select Key list box change depending on what is currently selected in the Select By box (see the following table).

The problems that match the Select By and Select Key values will be listed in the top display-only scrolling list box.

Problem List—This box contains a list of problems already entered into the system. Click on an item in the list to view its description in the Problem Description text box and its status in the Status box.

Click in the Problem Resolution box.

Problem Resolution—Type the description of the resolution of the problem.

Status—Choose Resolved from the Status list box.

Resolved By—Select your user D from the Resolved By list box.

Update—Click the Update button to update the Problem Notebook.

OK—Click the OK button to record the information you entered and return to the window that was displayed before you opened the Problem Notebook window.

Cancel—Click the Cancel button to exit the Problem Notebook without recording any information.

9 The Worklist

The Worklist manages scheduled callbacks. You will use the Worklist button in the NMS Main button bar FIG. 6) in two ways:

To open the Callback Scheduling window (FIG. 38) and schedule a callback for the Worklist. The Callback Scheduling window automatically opens when you click the Worklist button while you are processing an Emergency, Illness Care, Provider Selection, or Information call.

To open the Worklist window (FIG. 37) and view scheduled callbacks or perform a callback by accessing the Perform Callback window (FIG. 39). Clicking the Worklist button when you are not in the middle of a call session opens the Worklist window. This function of the Worklist button is described below.

Scheduling a Callback

In addition to scheduling a callback from the Self Care window (FIG. 26), a callback can be scheduled from the Callback Scheduling window while you are processing any kind of call. The following information is required for scheduling a callback:

- name of the caller
- telephone number of the caller
- time and date for the callback
- eligibility verified or a new patient chart created When you complete the entries in the Callback Scheduling window, the callback information will be placed in the Worklist for the nurse who is responsible for the callback.

Note: Only one callback can be scheduled for the call you are handling.

The Callback Scheduling Window

If you need to schedule a callback for the call you are handling, open the Callback Scheduling window.

Click the Worklist button in the IAS Main button bar or press F3 while you are in a call session.

The Callback Scheduling window displays.

Fill in the text boxes of the Callback Scheduling window, as described below.

Callback Date—Type the scheduled callback date using the format: 01-apr-94.

Callback Time—Type the time for making the callback using the format: 14:30.

Note: The system uses a 24-hour clock.

Caller Name—Type the first and last names of the caller.

Caller Phone—Type the phone number to call, beginning with the area code. Use the format: (401) 555-8751.

Responsible for Callback—Determines who will be assigned to make the callback.

Click the list button, then select the appropriate choice from the list. The choices are the users in the system. The default is the current user.

Callback Comments—Type your comments about the purpose of the callback

OK—Click the OK button to close the Callback Scheduling window and save the scheduled callback to the Worklist.

Cancel—Click the Cancel button if you decide not to schedule a callback.

Viewing the Worklist

If you are not in the middle of a call session, the Worklist window can be opened to view the scheduled callbacks and perform callbacks by accessing the Perform Callback window.

The Worklist Window

The Worklist window displays a list of all callbacks currently scheduled. Reading from left to right, each callback entry in the Worklist window shows:

- The date of the callback.
- The time of day to make the call.

Note: The hours and minutes are displayed in the 24-hour clock format. For example, 13:30:00, which means 1:30 p.m.

- Your user ID.
- The name of the caller.
- The number to call.

Click Worklist in the NMS Main button bar (FIG. 6) or press F3.

The Worklist window displays.

Finding a Callback in the Worklist

To find a scheduled callback in the Worklist window, first select the appropriate search criteria in the Select By and Select Key fields.

Select By—Use the Select By list button in the Worklist window to find callbacks selected by:

- Today's Date
- User
- Status

Select Key—The contents of the Select Key list box change depending on what is currently selected in the Select By box (see the following table).

Worklist Scrolling Text Box—The scrolling text box near the top of the Worklist window displays the list of callbacks that meet the criteria indicated in the Select By and Select Key boxes.

Click on the item in the box to display more information about the item in the following text boxes.

Assigned To—Only callbacks assigned to you display in the Worklist window.

The Assigned To box displays your user ID.

Status—The Status text box displays the status—Incomplete, Complete, or On Hold—of the currently selected callback item Note: If you choose Status in the Select By box, only callbacks corresponding to the Select Key will display. If you choose Today's Date in the Select By box, all items scheduled for today display.

Last Attempt—The Last Attempt box displays the date recorded for the last attempted callback.

Number of Attempts—The Number of Attempts box displays the number of attempted callbacks recorded.

OK—Click the OK button to close the Worklist window.

Cancel—Click the Cancel button to close the Worklist window.

Perform—Select an item in the Worklist Scrolling Text Box and click the Perform button to open the Perform Callback window.

Summary of Performing a Callback

Select the appropriate callback item from the Worklist window.

Click the Perform button to open the Perform Callback window.

Read the information presented in the Call Summary window.

Display and read the Patient Chart and Self Care Instructions windows.

Dial the Caller Phone number shown in the Perform Callback window.

If you reach the caller, make the appropriate inquiries regarding their condition, then type a description of the callback in the Resolution text box and mark the Call Result successful by clicking the Success radio button.

If the callback is not successful, choose a new time and date for the callback.

Update the Worklist by clicking the OK button.

Performing a Callback

When you are ready to perform a callback, you must select an item and click the Perform button in the Worklist window to open the Perform Callback window.

The Perform Callback Window

Click the Perform button in the Worklist window.

The Perform Callback window (FIG. 39) displays.

Caller Name—The Caller Name box displays the name of the caller—not necessarily the patient—who made the original call.

Caller Phone—The Caller Phone box displays the phone number to call.

Dial the telephone number shown in the Caller Phone box.

Inquire about the patient's status.

Last Attempt—The Last Attempt box displays the date recorded for the last attempted callback.

Attempts—The Number of Attempts box displays the number of attempted callbacks already recorded.

Call Summary—The Call Summary box displays information from the initial call when the callback was scheduled.

Display Patient Chart—The Display Patient Chart button opens the Patient Chart window.

Click the Display Patient Chart button to view the patient's chart. See Viewing Patient Charts for more information on patient's charts.

Display Self Care Instructions—The Display Self Care Instructions button opens the Self Care Instructions window.

Note: Pressing the Display Self Care Instructions button in the Worklist has no effect if a callback has been scheduled with the Callback Scheduling window.

The Self Care Instructions Window

The instructions given to the caller during the initial contact are displayed in the Self Care Instructions window.

Figure 40:
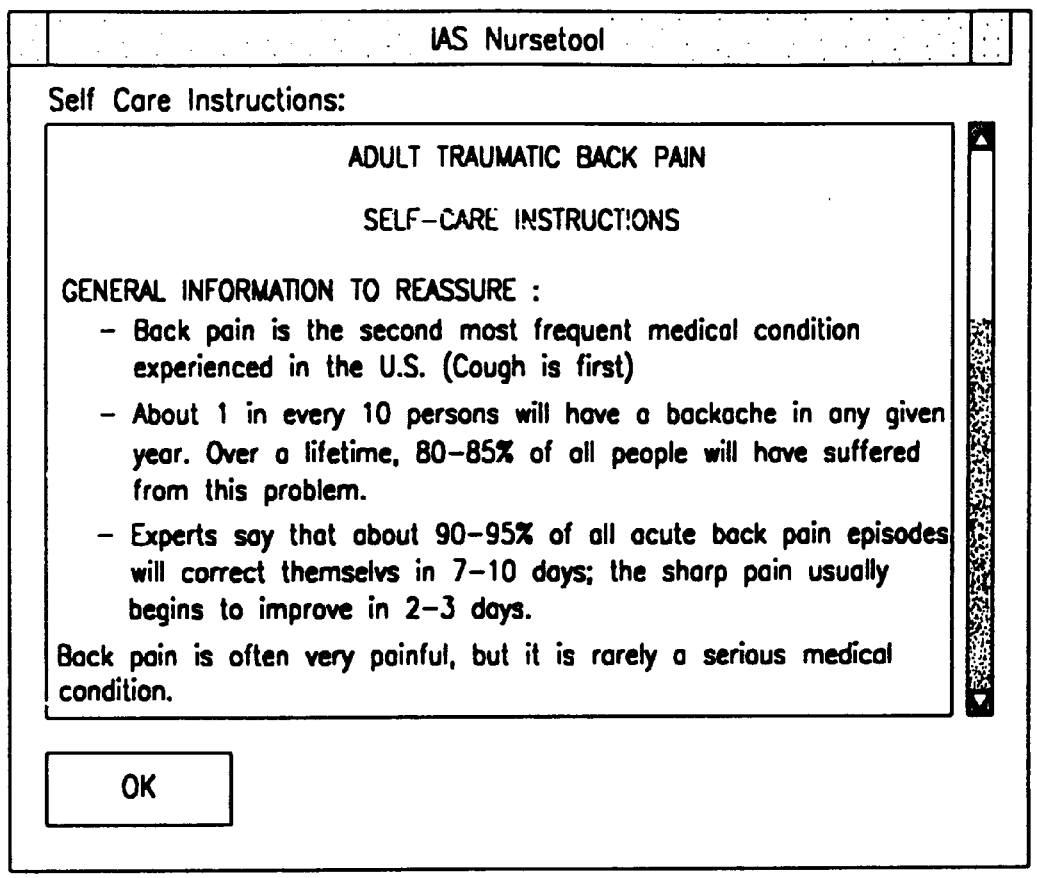

Click the Display Self Care Instructions button in the Worklist window to open the Self Care Instructions window (FIG. 40).

After you have reviewed the instructions, click the OK button in the Self Care Instructions window to close it and return to the Perform Callback window.

Logging the Callback

The results of the callback you made are logged in the Perform Callback window (see FIG. 39).

Call Result—Register the success or failure of the callback by clicking the appropriate radio button:

Click the Success radio button in the Perform Callback window if the callback was concluded successfully.

If the callback is not successful—e.g., no answer, or the individual was unable to take the call, or you need to schedule a subsequent call—click the Failure radio button.

Next Attempt Date—If the callback is not successful, or you want to schedule another callback, type the scheduled callback date using the format: 01-apr-94.

Note: The month must be the first three letters of the month in all lowercase letters.

Next Attempt Time—If the callback is not successful, type the scheduled callback time using the format 14:00

Note: The system uses a 24-hour clock.

Resolution—Click in the Resolution box and type information about how the current callback ended.

OK—Click the OK button to save data entered into the Perform Callback window, close the Perform Callback window, and return to the Worklist window.

Cancel—Click the Cancel button to close the Perform Callback window without saving any new data, and return to the Worklist window.

Updating the Worklist

Only the nurse administrator can update the Worklist.

The Callback Update window

Open the Worklist window and select a callback as described above.

Click the Update button in the Worklist window.

The Callback Update window (FIG. 41) displays.

Review the information.

As needed, change the information in the appropriate text boxes.

Note: The information shown in the Last Attempt, Attempts, and Call Summary boxes is for display only, and cannot be changed.

Click the OK button to update the Worklist.

10 Reviewing Information on Self Care and Health Plans

The Medical Information button in the NMS Main button bar (FIG. 6) allows you access to medical information on self care and/or rules for a particular health plan while you are already processing a call, unlike the Information call type described in Section 5, which should be used only when the caller has explicitly stated that the only reason for their call is to get information. Accessing medical information using the Medical Information button does not log a call—rather it provides a reference during processing of Illness Care or Provider Selection calls.

The Medical Information Button

The Information Type Selection window is available at any time and does not require verifying eligibility.

Click the Medical Information button in the NMS Main button bar or press F5.

The Information Type Selection window (FIG. 42) displays.

The Information Type Selection Window

The system groups information requests into two categories:

Medical Information

Health Plan Rules

You must select one of these categories from the Information Type Selection window.

The Information Type Selection window includes two radio buttons:

Medical Information—The Medical Information radio button in the Information Type Selection window allows you to select and display self-care instructions in the Self Care Selection window.

Health Plan Rules—The Health Plan Rules radio button in the Information Type Selection window allows you to select and display the rules for the patient's health plan in the Health Plan Rules Selection window.

OK—After selecting the radio button that corresponds to the requested information type, click the OK button to advance to the next window.

Cancel—Click the Cancel button to stop the Medical Information function.

Clicking the Cancel button closes the Information Type Selection window.

Medical Information

Figure 43:
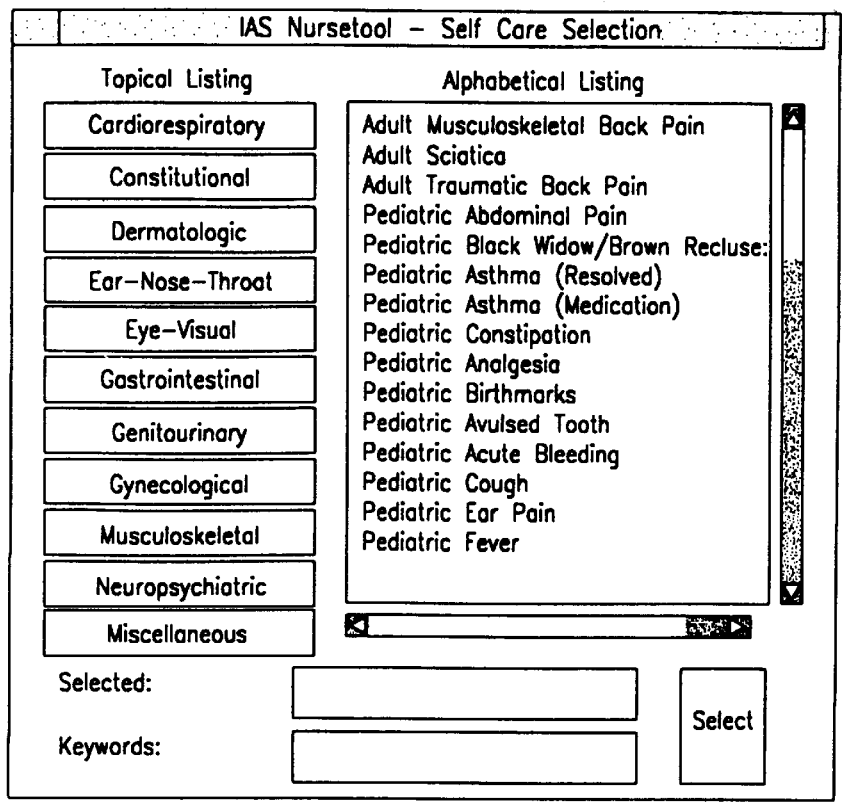

When you choose Medical Information from the Information Type Selection window, the Self Care Selection window displays. The Self Care Selection window allows you to choose the particular self care information to retrieve. The Self Care Selection window (FIG. 43), which is very similar to the Algorithm Selection window (see FIG. 18), allows selection of a self-care instruction based on a medical category and provides a way to search for self care instruction using keywords.

The Self Care Selection Window

The Self Care Selection window displays when you click the Medical Information radio button and then click the OK button in the Information Type Selection window.

Topical Listing—Click on the medical category that best describes the caller's request for information. A list of the corresponding self-care instructions displays in the Alphabetical Listing box.

Alphabetical Listing—Initially, the Alphabetical Listing scrolling list box displays a list of all self-care instructions in the system. When you click on a medical category using one of the Topical Listing buttons, or enter keywords into the Keywords box, the list is narrowed to display the self care instructions that correspond to the medical category or keywords.

You can double-click on an item in the Alphabetical Listing box to advance to the Self Care Instructions window.

Selected—This box displays the currently selected self care instruction item.

Keywords—Find a self care instruction by typing keywords that describe patient's request for information. Each keyword—including the last—must be followed by a semicolon (;).

Select—When you are satisfied that the item displayed in the Selected box corresponds to the patient's request for information, click the Select button to advance to the Self-Care Instructions window.

Note: Double-clicking on an item in the Alphabetical Listing box has the same effect as clicking the Select button.

The Self Care Instructions Window

Figure 44:
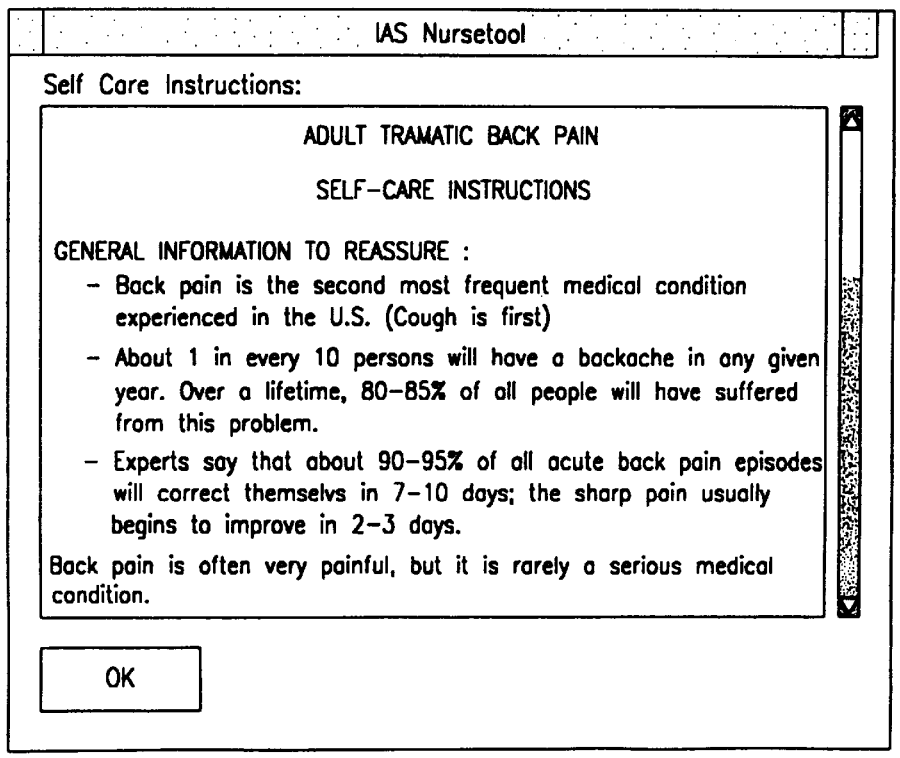

The Self Care Instructions window (FIG. 44) displays when you click the Select button or double-click on an item in the Alphabetical Listing box in the Self Care Selection window.

Self Care Instructions—This is a display-only scrolling text box with the instructions corresponding to the self care item selected from the Self Care Selection window.

OK—Click the OK button to exit the Self Care Instructions window when you are finished offering self care instruction to the caller. You may then either select another call type from the Call Type Selection Bar (see FIG. 8), or select Stop Call from the NMS Main button bar (see FIG. 6).

Health Plan Rules

Figure 45:
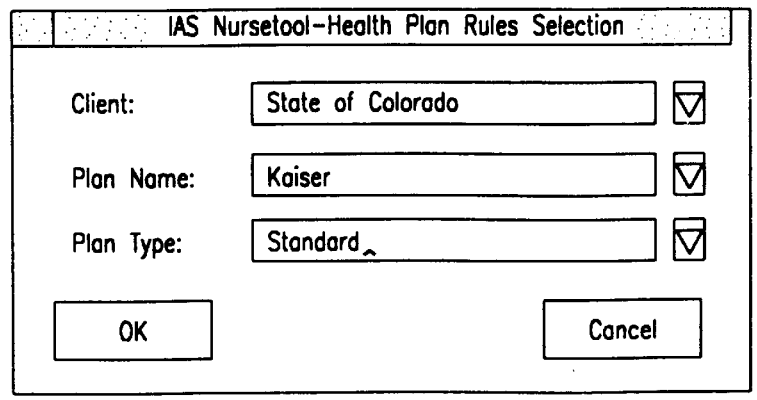

When you choose Health Plan Rules from the Information Type Selection window, a Health Plan Rules Selection window (FIG. 45) displays. The Health Plan Rules Selection window contains three pull-down list boxes to select the information you wish to search for in order to answer the caller's request for information.

The Health Plan Rules Selection Window

The Health Plan Rules Selection window displays when you click the Health Plan Rules radio button and then click the OK button in the Information Type Selection window.

Client—If the patient's chart is open, the client currently associated with the patient displays in the Client text box.

If the patient's chart is not open, or you want to change clients, click the list button to display a predefined list of clients.

Select a client name from the list box, OR

Type the requested client into the Client text box.

Plan Name—If the patient's chart is open, the patient's current plan name displays in the Plan Name text box.

If the patient's chart is not open, or you want to change plan names, click the list button to display a predefined list of plans.

Select a plan name from the list box, OR

Type the name of the plan into the Plan Name text box.

Plan Type—If the patient's chart is open, the patient's current plan type displays in the Plan Type text box.

If the patient's chart is not open, or you want to change the plan type, click the list button to display a predefined list of plan types.

Select a plan type from the list box,

Type the plan type into the Plan Type text box.

OK—Click the OK button to display the requested information in the Health Plan Rules window.

Click the OK button.

Cancel—Click the Cancel button to cancel a request for insurance rules information and close the Health Plan Rules Selection window.

The Health Plan Rules Window

Figure 46:
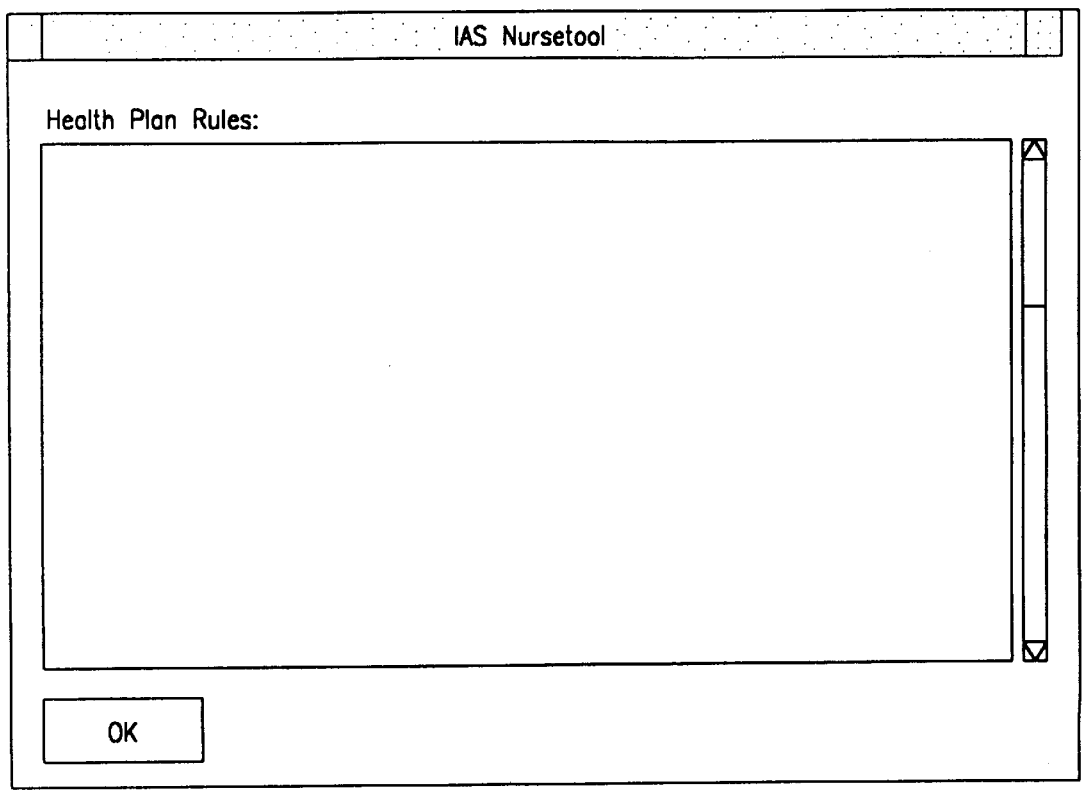

The Health Plan Rules window (FIG. 46) displays when you click the OK button in the Health Plan Rules Selection window.

Health Plan Rules—This is a display-only scrolling text box containing the requested health plan rules information.

Note: If no health plan rules are available for the plan you selected in the Health Plan Rules Selection window, a message window may display. Click the OK button in the message window to continue.

Click the OK button to close the Health Plan Rules window.

11 Provider Selection

The Provider Selection function of the NMS Network Management System is designed to assist you in helping the caller select an appropriate medical provider. The process is designed to help callers select the provider who best matches their needs.

To perform the search for a provider, the NMS Network Management System uses search codes grouped into categories to build a list of criteria the provider must have to satisfy the needs of the patient. Criteria can be added to, changed, or deleted from the list to narrow or widen the search for providers who match the criteria.

When the NMS Network Management System displays a list of matching providers in the Provider Search Results window, you may either make an appointment for the patient with one of the providers listed, or make referrals to one or more of the providers listed.

Summary of Provider Selection

The Provider Selection function can be started two ways:

As a call type by selecting the Provider Selection (F8) call type from the Call Type Selection button bar (FIG. 8). This path to Provider Selection is used when the caller is not symptomatic and is looking to select a provider for reasons other than for illness care.

In conjunction with an Illness Care call that results in recommending provider selection.

To use the Provider Selection portion of the NMS Network Management System under either condition, you must have started a call and completed the Caller Info window and the Eligibility Verification window. For more information about the Caller Info window, see Section 1, Starting a Call. For more information about the Eligibility Verification window, see the Section 3, Eligibility Verification. As in other call sequences, the Patient Chart will display. More information about the patient chart is provided in Section 3.

Note: If a call session is in progress (i.e., for medical assessment), the patient chart will already be present, and eligibility verification will already be satisfied. Steps Involved in a Provider Search The steps for performing Provider Selection after you have opened the Provider Criteria window (FIG. 47) are summarized below.

When the Provider Criteria window opens, an initial match is performed by the NMS Network Management System on the "automatic" criteria These criteria can be changed or deleted by the Nurse when necessary. (See Automatic Criteria Entered into the Criteria List, below.)

Additional criteria can be added to the Criteria List in the Provider Criteria window to further narrow the search. (See Listing Criteria Desired in a Provider, below.)

After adding, changing, or deleting criteria, select the Providers Matched (ESC+s) button to see how may providers match the listed criteria (See Determining the Number of Providers Matched, below.)

If an adequate number of matches is found, open the Provider Search Results window (FIG. 48) to display the list of providers who match the Criteria List. (See Viewing the Providers Matched, below.)

Select one of the providers from the list of matching providers in the Provider Search Results window. (See The Provider Search Results Window, FIG. 48.)

View the biographical information about the selected provider and relate the information to the caller. (See The Provider Biography Window, FIG. 49.)

When the patient selects one of the providers, you may make a referral or an appointment.

Making an appointment involves scheduling a visit with one provider (multiple appointments cannot be made). Before you can make an appointment with a provider, however, you must view the provider's biographical information in the Provider Biography window. (See Making an Appointment, below.)

A referral means giving the provider's name and telephone number to the patient.

Multiple referrals can be given, and referrals can be given to the patient without reviewing providers' biographical information in the Provider Biography window.

(See Logging a Referral, below.)

Provider Selection as a Call Type

The Provider Selection process can be initiated from the Call Type Selection button bar FIG. 8) using the Provider Selection (F8) button.

Click the Provider Selection button in the Call Type Selection button bar or press F8.

The Eligibility Verification window (FIG. 11) displays.

The steps for using the Eligibility Verification window to locate a patient's chart are described in Chapter 3, Finding, Creating and Viewing Patient Charts.

Figure 50:
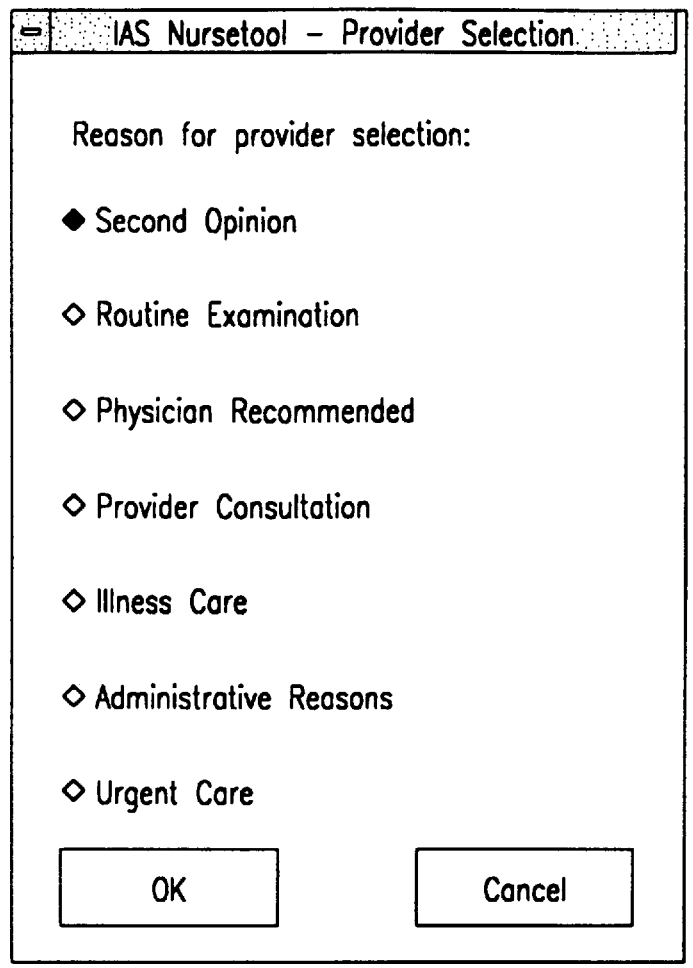

After the patient chart is found or created, the Provider Selection window displays (see FIG. 50).

The Provider Selection Window

The Provider Selection window displays a list of reasons for selecting a provider.

The reason you select will be recorded with the call and in the patient's chart

The Provider Selection window displays when you click the Provider Selection button in the Call Type Selection button bar or press F8.

Indicate the reason for performing the Provider Selection process by clicking the radio button to the left of your selection.

Second Opinion—Patient is seeking another opinion on a previous diagnosis or a treatment received from another provider.

Routine Examination—Patient is not symptomatic but is seeking a provider for a routine medical examination.

Physician Recommended—Patient's doctor has recommended that the patient find a doctor for a specific need.

Provider Consultation—The patient is not ill, but wants to speak to a provider for advice, e.g., birth-control consultation.

Illness Care—Used for illness care calls where the patient refuses all the choices on the Nurse Action List and decides to pursue provider selection.

Administrative Reasons—Patient is required by their health plan to select a provider.

If you select Administrative Reasons and subsequently make an appointment with one of the providers viewed, that provider will be recorded in the patient's chart as the patient's primary care physician.

Urgent Care—The patient requires immediate, non-emergency medical evaluation and/or treatment that precludes the need for sorting through the algorithms, e.g., obvious fracture.

Urgent Care automatically adds the current date and time to the Criteria List in the Provider Criteria window.

OK—Click the OK button to record your selection and to open the Provider Criteria window.

Ending the Search for a Provider

Cancel—If you choose not to proceed, click the Cancel button to end the Provider Selection session.

Click the Cancel button in the Provider Selection window to end the Provider Selection session without saving any of the information entered.

Provider Selection from the Nurse Action List

In the course of an Illness Care call session, the Provider Selection function may be initiated when Urgent Care, Early Illness Appointment, or Routine Illness Appointment is selected as an option in the Nurse Action List window (FIG. 24) and you click the Select button or if the NMS provider recommends urgent care, early illness appointment, or a routine illness appointment.

Figure 51:
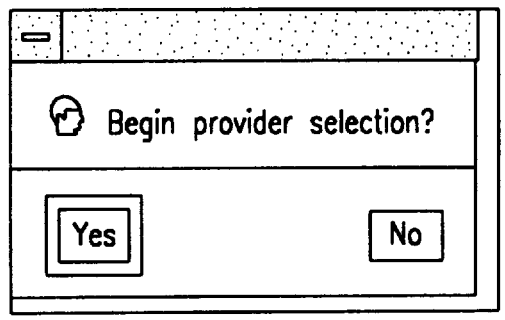

Select a Provider Selection action such as Urgent Care, Early Illness Appointment, or Routine Illness Appointment from the Nurse Action List window. The Begin Provider Selection? message window (FIG. 51) displays.

Click the YES button in the message window.

The Provider Criteria window displays (see FIG. 47).

Listing Criteria Desired in a Provider

The Provider Criteria window is designed to help you match patient needs with the skills and attributes of providers in the system's database. To ensure selection of an appropriate provider for the caller, you will create/modify a list of search criteria, the Criteria List, that best describes the patient's needs for a provider. The system compares this Criteria List to the provider database to determine the number of "matches". You may add criteria, change criteria, or delete criteria in the Criteria List to arrive at a reasonable number of provider matches from which the patient may choose.

The Provider Criteria Window

The search categories and criteria are accessed from the Provider Criteria window.

The Provider Criteria window can be opened two ways, as described in Provider Selection from the Nurse Action List and Provider Selection as a Call Type.

Automatic Criteria Entered into the Criteria List

When you begin Provider Selection from the Call Type Selection button bar, or by selecting Urgent Care, Early Illness Appointment, or Routine Illness Appointment from the Nurse Action List window., four criteria are pulled automatically from the patient chart and entered into the Criteria List in the Provider Criteria window. These criteria are:

Patient's age—AAGE

Patient's gender—AGEN

Patient's health plan—PLAN

Patient's zip code—ZIMA

If the action being taken is Urgent Care, the following criteria are also added:

The current day—DAY

The current time (to the next quarter hour)—TIME

The day and time are added in order to search for an office that is open at the current time.

All these automatic criteria can be changed in the Criteria List by the nurse, as necessary. For example, the time can be changed to reflect the given situation (e.g., the patient needs to drive half an hour to reach care).

In addition, if the action you selected contains clinical or procedural codes, those codes are added by the system to the Criteria List in the Provider Criteria window.

The system performs a preliminary search based on the criteria automatically added to the Criteria List from the patient's chart.

Adding Criteria to the Criteria List

Criteria Type—The select buttons in the Criteria Type section of the Provider Criteria window represent the 13 categories of criteria available for a provider search. Definitions of the criteria in each of the first 11 categories in the Criteria Type section are provided in tables at the end of this chapter. The Clinical Codes and Procedural Codes categories are briefly described below, but are not described in detail in this manual since these categories are well documented in readily available medical reference books.

Click the appropriate Criteria Type button, based on the needs of the caller.

The codes in the Criteria Type category you selected display in the Codes scrolling list box. A description of each code displays directly opposite the code in the Descriptions scrolling list box.

Codes—This scrolling list box displays all the codes available for the category you selected from the Criteria Type buttons.

Descriptions—This scrolling list box displays a description for each code in the Codes scrolling list box. The codes that require a value indicate what type of value needs to be entered in the Value box.

Selected Criterion—This text box displays the description of the code selected from the Codes scrolling list box. You can also type a code followed by a colon (:) into this box (see the steps below).

You can select a search code two ways:

Click on a code's description to display it in the Selected Criterion text entry box. OR Click in the Selected Criterion text entry box.

Type the code followed by a colon (:) in the Selected Criterion text entry box. The description of the code will automatically display in the Selected Criterion text entry box as soon as you type the colon. For example, type gend: to place GEND: Provider's gender is in the Selected Criterion text entry box.

Value—Some of the codes require that a value be entered in the Value box. When a value for the code does not automatically display in the Value box, you may need to type a number in the Value box or select one of the values from the list box associated with the Value box. When a value is required for a code, the type of value expected is displayed next to the description of the code in the Descriptions scrolling list box. The types of values are:

<integer>—a number

<string>—words

<time>—the time using the 24-hour clock

<state>—the two-character, capital letters, abbreviation for the state

<zip code>—the five digit zip code

<list>—one of the values listed in the list box associated with the Value box.

Click in the Value box.

Type the number (integer) or word.

Click the list button to display the list of values. For example, if you wish to specify the provider's gender, Male and Female will appear in the list box for Value box.

Click on one of the choices in the list box to display it in the Value box.

Insert—The Insert button is next to the Selected Criterion box. Use it to add the Selected Criterion and its Value to the Criteria List.

When you are satisfied with the code, description and value displayed in the Selected Criterion and Value boxes, click the Insert button.

The criterion will be added to the Criteria List.

Continue to add criteria in the manner described above until you have added all the criteria to the Criteria List that the caller wishes to use in the selection process.

Criteria List—The combination of selected criteria displayed in the Criteria List determines the number of matches you will have to providers on the list. Criteria can also be selected from the CPT/ICD code selection windows. See Selecting CPT/ICD Codes for more details on this process.

Note: The process of adding, changing and deleting codes does not automatically perform a search. Results of the Criteria List matching are compiled when you click the Providers Matched button.

To continue the Provider Selection process, determine the number of providers who match the criteria in the Criteria List as described in Determining the Number of Providers Matched.

Ending the Search for a Provider

Cancel—Click the Cancel button if you want to exit the Provider Criteria window and quit the Provider Selection session.

Click the Cancel button in the Provider Criteria window to end the Provider Selection session without saving any of the information entered.

Selecting CPT/ICD Codes

Figure 52:
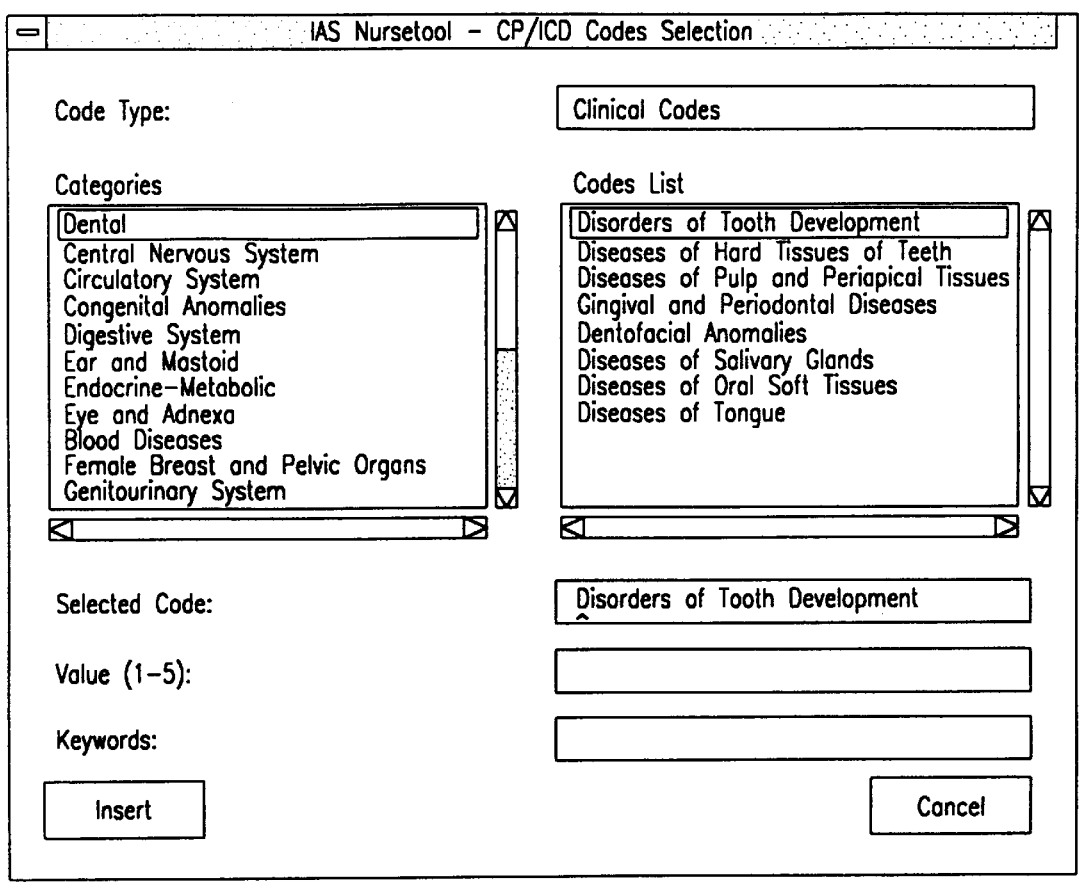

The Clinical Codes and Procedural Codes buttons in the Provider Criteria window allow you to specify search criteria for detailed information about the provider's self-described level of expertise with specific medical conditions and diseases or specific medical procedures in the CPT/ICD Codes Selection window (FIG. 52).

The CPT/ICD Codes Selection Window

If the caller wishes to specify expertise in a particular area, you can click either the Clinical Codes button or the Procedural Codes button in the Provider Criteria window to display the related CPT/ICD Codes Selection window.

Clinical Codes—Clicking the Clinical Codes button opens the Provider Criteria window with clinical codes displayed in the Codes List.

Click the Clinical Codes button in the Provider Criteria window.

The CPT/ICD Codes Selection window displays with Clinical Codes displayed in the Code Type box (see FIG. 52).

Procedural Codes—Clicking the Procedural Codes button opens the Provider Criteria window with procedural codes displayed in the Codes List.

Click the Procedural Codes button in the Provider Criteria window.

Figure 53:
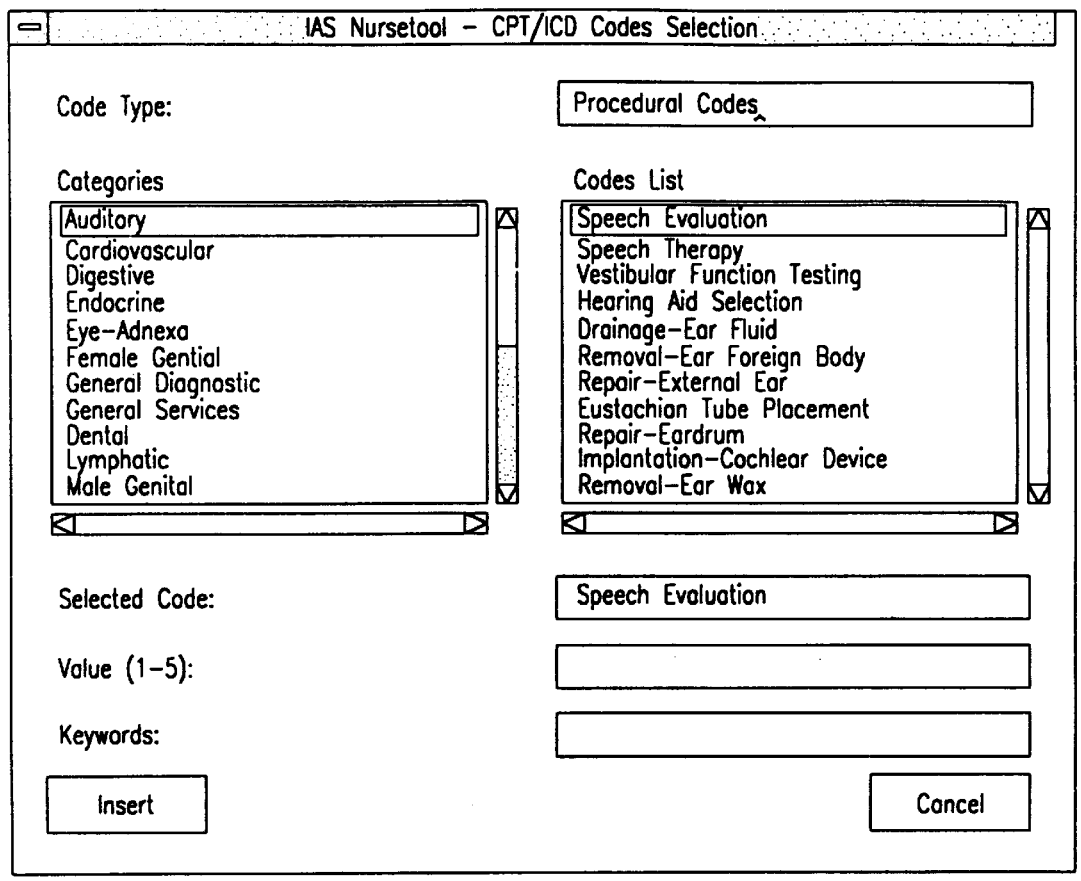

The CPT/ICD Codes Selection window displays with Procedural Codes displayed in the Code Type box (see FIG. 53).

Code Type—The type of code you selected with the Criteria Type button (Procedural or Clinical) in the Provider Criteria window is displayed here.

Categories—This scrolling list box displays the categories of codes that are available for the Code Type.

Select a general category from the Categories text box by clicking on it. A list of codes related to the category will display in the Codes List scrolling list box.

Codes List—The codes available for the category selected in the Categories box display in this scrolling list box.

Selected Code—The Procedural or Clinical code highlighted in the Codes List scrolling text box displays here.

Highlight the code in the Codes List scrolling text box that closely matches the area you wish to search for. The highlighted code displays in the Selected Code text box.

Value—Once a selected code is displayed in the Selected Code box of the CPT/ICD Codes Selection window, you must type a number between 1 and 4 in the Value box to indicate the level of expertise the caller requires the provider to have with this code. The meanings of the values 1, 2, 3, and 4 are as follows:

1—I do not generally accept patients with this disorder.

2—I generally refer out the evaluation and diagnostic testing for patients suspected with this disorder but then prefer to continue with the patient for necessary treatment and/or management.

3—I accept patients suspected with this disorder for evaluation, diagnostic testing and most forms of necessary treatment and/or management.

4—I have exceptional clinical expertise and/or professional interest in patients with this disorder.

Values greater than 4 may be defined for an individual site.

Note: Levels of expertise for these codes are defined by each provider when they are added to the database.

Click in the Value text box

Type a number between 1 and 4.

Keywords—As an alternative to scrolling through a category's entire set of codes in the Codes List scrolling text box of the CPT/ICD Codes Selection window in order to find a code, you can shorten the list of codes displayed in the Codes List scrolling text box by typing keywords into the Keywords text box.

Click in the Keywords text box.

Type keywords that describe the patient's symptom(s). Each keyword, including the last, must be followed by a semicolon (;). As soon as you type the semicolon, the related codes are listed in the Codes List scrolling list box. Multi-word keywords must be connected by a hyphen (-). Abbreviations may be used.

Note: This list can contain codes from multiple categories.

Insert—When you are satisfied with the code displayed in the Selected Code box and you have entered a value in the Value box, you must click the Insert button to enter the code and value into the Criteria List in the Provider Criteria window.

Click the Insert button.

The criterion is added to the Criteria List in the Provider Criteria window.

Cancel—When you are finished selecting criteria from the CPT/ICD Codes Selection window, click the Cancel button to close the window.

Determining the Number of Providers Matched

The system performs a preliminary search based on the criteria automatically added to the Criteria List from the patient's chart (See Provider Selection as a Call Type and Provider Selection from the Nurse Action List.) If any providers matched those criteria, the number of matches displays in the box immediately to the right of the Providers Matched button when the window opens.

After the patient's criteria for selecting a provider have been added to the Criteria List in the Provider Criteria window, you must click the Providers Matched button to see how many providers match the revised criteria.

Providers Matched—This button instructs the system to count all the providers who match the criteria listed in the Criteria List.

Click the Providers Matched button in the Provider Criteria window or press ESC+s.

The number of providers who match all of the selected criteria displays in the box immediately to the right of the Providers Matched button. A good range of matches is somewhere between 2 and 4 so that the caller will have some selection but will not be overwhelmed. You may have to change criteria or delete some criteria to arrive at a good number. See Refining the Criteria List.

The Fast Search

The system performs a preliminary search based on the criteria automatically added to the Criteria List from the patient's chart See Automatic Criteria Entered into the Criteria List.

Refining the Criteria List

Deleting Criteria from the Criteria List

If no matches are found, it is possible that the search criteria are too specific and some of them need to be deleted to widen the search.

In the Criteria List, highlight a criterion you wish to remove from the

Criteria List list box. The highlighted criterion will display in the Selected Criterion box.

Click the Delete button to the right of the Value text entry box to remove the criterion from the Criteria List.

The selected criterion is removed from the list

Changing a Criterion Value

The value of a criterion in the Criteria List can be modified directly to further constrain or loosen the search.

In the Criteria List, highlight a criterion you wish to change. The highlighted criterion will display in the Selected Criterion box.

Click the Value box and edit the value, OR

Click the Value list button and select a different item from the list box.

Click the Insert button. The criterion in the Criteria—List will display the new value.

Adding Comments About the Search

If there are no matches to a given Criteria List, you may enter a description of the search attempt in the Comments window to provide detail for reporting purposes.

Figure 54:
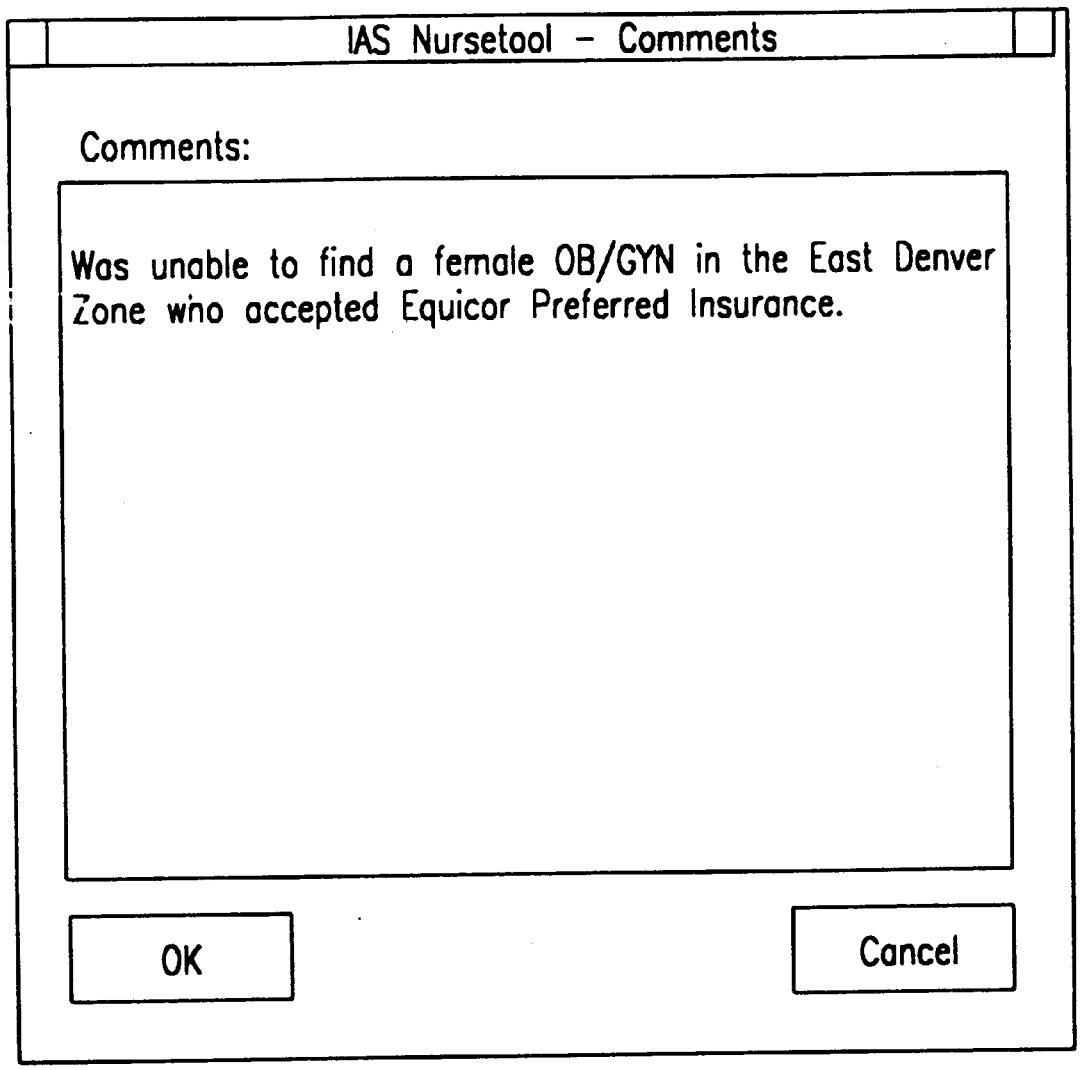

Comments—Clicking the Comments button in the Provider Criteria window opens the Comments window FIG. 54).

The Comments Window

The text box in the Comments window is used to indicate the reasons for zero matches. Entry of comments in this text box is not required, but it is helpful to note reasons for the lack of matches made (e.g., there are no female obstetricians in this area of the city).

Click the Comments button in the Provider Criteria window. The Comments window (FIG. 54) displays.

Type comments in the Comments text box.

OK—Clicking the OK button saves the comments to the database.

Cancel—Clicking the Cancel button allows you to exit the Comments window without saving the comments to a file.

Viewing the Providers Matched

When the search has resulted in a reasonable number of matching providers (described in Determining the Number of Providers Matched), you are ready to display the information about those providers.

Display—Clicking the Display button in the Provider Criteria window (FIG. 47) opens the Provider Search Results window (FIG. 48).

The Provider Search Results Window

The Provider Search Results window provides a topline about the provider whose name is highlighted in the scrolling list box.

Click the Display button in the Provider Criteria window.

The Provider Search Results window displays.

Scrolling List Box—The list of the providers generated by your search displays in the Provider Search Results window.

Click on one of the providers listed in the scrolling list box.

The topline information about this provider displays in the six text boxes of the Provider Search Results window.

Address—The street address of the provider.

City, State—The name of the city and state where the office of the provider is located displays here.

Specialty—The primary specialty of the provider.

Years in Practice—The number of years the provider has been practicing medicine displays here.

Age—The age of the provider.

Gender—The sex of the provider.

Click one of the following buttons to advance in the provider selection process.

Referral—If you plan to give the caller the name of the provider, click the Referral button. Clicking the Referral button logs a referral to the provider who is highlighted in the scrolling list box.

View Bio—Clicking the View Bio button displays the Provider Biography window for the provider highlighted in the scrolling list box. Using the Provider Biography window, you can provide the caller with detailed information about the provider in a number of categories. See The Provider Biography Window, page 11–20 for a description of those categories.

Own Provider—Clicking the Own Provider button displays the biography of the caller's current provider, if one is listed in the patient chart and that provider is in the database, whether or not that provider was in the search.

Returning to the Search Criteria Window

Cancel—Clicking the Cancel button closes the Provider Search Results window and returns you to the Search Criteria window.

Click the Cancel button in the Provider Search Results window to close it and return to the Search Criteria window.

Ending the Search for a Provider

OK—Clicking the OK button ends the Provider Selection session.

Click the OK button in the Provider Search Results window to end the Provider Selection session.

The Are you sure you want to end provider selection? message window (FIG. 55) displays.

If you want to close all the Provider Selection windows and end the Provider Selection session, click the YES button in the message window. OR If you want to continue the Provider Selection session and return to the Provider Search Results window (FIG. 48), click the NO button in the message window.

Viewing Biographical Information

The Provider Biography window (FIG. 56) displays biographical information about the selected provider and allows you to log a referral or to make an appointment for the patient.

The Provider Biography Window

There are six buttons in the Provider Biography window for displaying detailed information about the provider.

General Info./Credentials—Name, office address, telephone number and education.

Characteristics—Gender, age, marital status, years in practice, ethnic origin, religion and prescription policies.

Office Information—Physical characteristics of the office, office hours, and lead times for appointments.

Payment Policies—Fees, methods of payment, and health plans in which the provider participates.

Clinical Information—Expertise levels the provider has for treating conditions listed by clinical provider codes.

Procedural Information—Expertise levels the provider has for procedures listed by procedural provider codes.

Click on the View Bio button in the Provider Search Results window.

The Provider Biography window displays.

The categories and definitions are roughly equivalent to the listing in the Provider Criteria window.

Instructions for making a referral are provided in Logging a Referral.

Instructions for making an appointment with the provider are provided in Making an Appointment.

Click one of the following buttons in the Provider Biography window:

General Info./Credentials

Characteristics

Office Information

Payment Policies

Clinical Information

Procedural Information

General Info/Credentials—Clicking the General Info./Credentials button in the Provider Biography window displays a listing of the provider's name, address, years in practice, hospital affiliation, and so on.

Characteristics—Clicking the Characteristics button in the Provider Biography window displays biographical information about the provider (age, gender, and so on) and also information about prescription policies.

Office Information—Clicking the Office Information button in the Provider Biography window displays information about hours and other office policies which the provider uses.

Payment Policies—Clicking the Payment Policies button in the Provider Biography window displays information about what credit cards and health plans the provider's office accepts, as well as what payment plans might be available.

Clinical Information—Clicking the Clinical Information button in the Provider Biography window displays information about treatment style and areas of expertise for the chosen provider, complete with clinical codes and level of expertise.

Procedural Information—Clicking the Procedural Information button in the Provider Biography window displays information about procedures the provider is qualified to perform, with attendant level of expertise.

Once you have reviewed all the information you need on the information display windows, you may make a referral, make an appointment, or exit the Provider Selection process without taking an action. See Logging a Referral See Making an Appointment. See Ending the Provider Selection Session.

Logging a Referral

Multiple referrals to multiple providers can be made with the NMS Network Management System. However, the number of referrals to a given provider for a particular health plan may have a flow limit. If so, a referral will fail if the provider's limited flow for the patient's health plan has been exceeded between the time of the search (which does an internal check) and when the Referral button has been clicked.

Referral—Clicking the Referral button in either the Provider Search Results window or the Provider Biography window logs the caller's intention to consult the provider listed and displays the Referral message window.

> Click the Referral button in either the Provider Search Results window or the Provider Biography window.
> The Referral message window (FIG. 57) displays.

The Referral message window indicates that the referral to the provider has been logged.

> Click the OK button in the Referral message window to close it You can continue with the Provider Selection session using either the Provider Search Results window or the Provider Biography window. If you then click the Referral button to make a referral to another provider, the Referral message window will be displayed to indicate that the referral to that provider has also been logged.

Making an Appointment

At the instruction of the caller, you can call the provider and make an appointment for the patient.

Note: You may make only one appointment for a patient during a Provider Search session.

Figure 58:
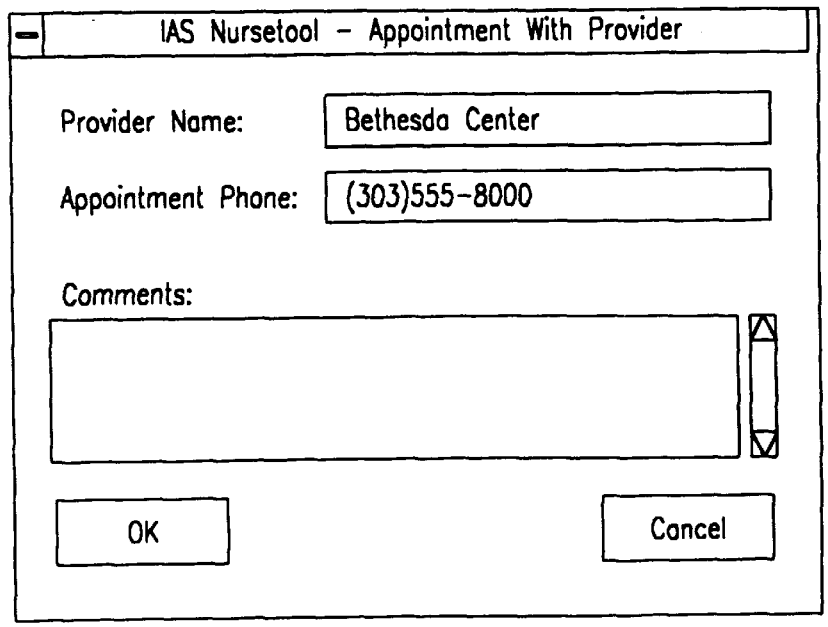

Appointment—Clicking the Appointment button in the Provider Biography window displays the Appointment with Provider window (FIG. 58).

The Appointment with Provider Window

The Appointment with Provider window displays the selected provider's name and appointment telephone number. You will need to call the provider to make the appointment and indicate whether you were able to make the appointment.

> Click the Appointment button in the Provider Biography window.
> The Appointment with Provider window displays.

Provider Name—This box displays the name of the selected provider.

Appointment Phone—This box displays the appointment telephone number of the selected provider.

Comments—You may enter comments in the Comments text box to record the results of this transaction.

> Call the telephone number displayed in the Appointment Phone box and make the appointment for the patient.

Appointment made?—The Yes radio button indicates the appointment was made; the No radio button indicates the appointment was not made.

> If you were successful in making the appointment, click the Yes radio button. If you were not successful in making the appointment, click the No radio button.

OK—Clicking the OK button in the Appointment with Provider window ends the Provider Selection session and saves the information you entered into the Provider Selection windows in the database.

> After you have made the appointment, click the OK button in the Appointment with Provider window to end the Provider Selection session and save the information from the Provider Selection session to the database.

Cancel—Clicking the Cancel button in the Appointment with Provider window ends a Provider Selection session without saving the information entered into any of the windows during the Provider Selection session.

> If you decide to end the Provider Selection session without making an appointment or saving your comments in the Comments window, click the Cancel button the Appointment with Provider window.

Ending the Provider Selection Session

After a successful Provider Selection session, where you have either made referrals to providers or made an appointment with a provider, you will want to end the session and save the information you entered into the Provider Selection windows in the database.

Ending the Session and Updating the Database

OK—Clicking the OK button in the Provider Search Results window or the Appointment with Provider window ends the Provider Selection session and saves the information you entered into the Provider Selection windows in the database.

> After you have made the appointment, click the OK button in the Appointment with Provider window to end the Provider Selection session and save the information you entered into the Provider Selection windows to the database.

> After you have made referrals, click the OK button in the Provider Search Results window to end the Provider Selection session and save the information you entered into the Provider Selection windows to the database.

Ending the Session without Updating the Database

Cancel—Clicking the Cancel button in either the Provider Selection window or the Provider Criteria window ends a Provider Selection session without saving the information entered into any of the windows during the Provider Selection session.

> If you decide to end the Provider Selection session without making a referral or an appointment or saving your comments in the Comments window, click the Cancel button in either the Provider Selection window or the Provider Criteria window.

Criteria Type Descriptions

Provider Type

The Provider Type category allows you to specify the type of provider or facility the patient requests, e.g., freestanding, hospital, clinic, and so on, as the Criteria Type in the Provider Criteria window.

| Code | Description | Value | Definition |
|---|---|---|---|
| PHYS | Provider is a physician | | Provider is an MD or DO (Doctor of Osteopathy). |
| DENT | Provider is a dentist | | Provider is a DDS. |
| FACL | Provider is a facility | | Provider is a hospital, clinic, or other care facility composed of health care professionals |
| ALLY | Provider is in Allied Health | | Any non-physician provider such as a physical therapist, chiropractor, or nurse practitioner. |
| MENT | Provider is in Mental Health | | Provider gives mental health services to patients, e.g. psychologist, social worker, psychiatrist, or psychiatric nurse. |

Personal

The Personal category allows you to indicate specific personal characteristics about the provider as the Criteria Type in the Provider Criteria window.

| Code | Description | Value | Definition |
|---|---|---|---|
| GEND | Provider's gender is | list | Use the list in the value field to select male or female. |
| OAGE | Provider is __ years or older | integer | Use the value field to indicate the minimum age. |
| UAGE | Provider is __ years or younger | integer | Use the value field to indicate the maximum age. |
| MARS | Provider's marital status is | list | Use the list in the value field to select marital status. |
| ETHOS | Provider's ethnic background | list | Use the list in the value field to indicate the ethnic background. |
| RELIG | Provider's religion | list | Use the list in the value field to indicate the religion. |
| FNAME | Provider's first name | string | Type the first name in the value field. No format is required, but do not abbreviate the name. |
| LNAME | Provider's last name | string | Type the last name in the value field. No format is required, but do not abbreviate the name |

Credentials

The Credentials category allows you to specify preferences about the provider's professional credentials as the Criteria Type in the Provider Criteria window.

| Code | Description | Value | Definition |
|---|---|---|---|
| NYEAR | In practice __ or more years | integer | Indicate a minimum number of years of experience. |
| TSTYL | Provider's treatment style | list | Specify medical expert, educator, or collaborator. |
| SPEC | Provider's specialty | list | Specify medical specialty by selecting a value from the list box. |
| LICEN | Licensure in state | state | Ensure provider is licensed to practice in a given state by typing a two-character abbreviation for the state in capital letters, e.g., CO for Colorado. |
| HOSP | Hospital affiliations | list | Hospital where the provider admits. Select a value from the list box. |
| SCERT | Provider's board-certified | list | A medical discipline in which the specialty provider is board-certified. Select a value from the list box. |
| UNIF | Active-duty, military | | Provider is a uniformed military provider. |

Office Information

The Office Information category allows you to specify certain characteristics of the office practice as the Criteria Type.

| Code | Description | Value | Definition |
|---|---|---|---|
| PYTYPE | Provider's practice type | list | Solo, group or multi-specialty practice. |
| DAY | Office open on 'day' | list | Specific day of week when office is open. This element must be used in conjunction with the time element. |
| TIME | Office open at 'time' | time | Time of day when the office opens. This element uses the 24-hour clock, e.g., 15:00 is 3 p.m. The formats 7:00 and 07:00 may also be used. This element must be used in conjunction with the day element. |
| 24HR | Office open 24 hours a day | | Office is open on all days, all times. |
| WEND | Office open on weekends | | Office is open at some time on Saturday or Sunday. |
| EVENG | Office open during evening | | Office is open after 5 p.m. on at least one weekday (M-F). |
| MORNG | Office open during early morning | | Office is open prior to 8 a.m. on at least one weekday (M-F). |
| ZIP | Office location zip code | zip code | Office is in designated zip code. Use the same zip code for this type and the following three types of zip code searches. |
| ZIMA | Office in immediate area of zip code | zipcode | The office is in the zip code entered, or in |

| Code | Description | Value | Definition |
|---|---|---|---|
| ZAREA | Office in general area of zipcode | zip code | nearby zip codes. Widens the zip code search slightly from the previous category. |
| ZONE | Office in zip zone | zip code | Widens the zip code search slightly from the previous category. |
| SAREA | Office in service area | list | Office location within a city/metropolitan area. |
| LANG | Foreign language spoken | list | Language other than English is spoken in the provider's office, selectable from a list. |
| WHEEL | Wheelchair accessible | | Office has wheelchair access. |
| PUBT | Nearest public transportation is less than x blocks | integer | Specify the proximity of public transportation in indicated number of blocks or less. |
| DRUGS | Pharmacy available at office | | Pharmacy co-located with office. |

Office Policy

The Office Policy category allows you to specify basic types of services that the provider's office offers as the Criteria Type in the Provider Criteria window.

| Code | Description | Value | Definition |
|---|---|---|---|
| NAPT | Same day/next day appointments for new patients | | Provider will accept new patients on a same day/next day basis. |
| WALK | Walk-ins accepted | | Provider sees patients without an appointment. |
| AHTEL | After-hours telephone consultation for new patients | | Office provides after-hours consultation for new patients. |
| DHPRE | During hours prescriptions | list | Prescriptions may be considered by the provider over the phone during office hours in some situations. Specify the type of patient and refill vs. new prescription in the list. |
| AHPRE | Mter hours prescriptions | list | Prescriptions may be considered by the provider over the phone after office hours in some situations. Specify the type of patient and refill vs. new prescription in the list. |

Patient Type

The Patient Type category allows you to specify the types of patient and patient circumstances which the provider will accept as the Criteria Type in the Provider Criteria window.

| Code | Description | Value | Definition |
|---|---|---|---|
| AAGE | Accepts patients of age | integer | Specify age of patient. This element must be used in conjunction with the gender element. |
| AGEN | Accepts patients of gender | list | Specify gender of patient. |
| ACONS | Accepts patients for second opinion/consultation | | Accepts patients who are seeking only a second opinion or consultation from the provider. |
| ARREL | Accepts patients who will not accept care for religious reasons | | Accepts patients who might refuse treatment for religious reasons. For example, some religious groups will not consent to blood transfusions. |
| APCAP | Accepts physically handicapped | | Accepts patients with physical handicaps, e.g. paraplegics, cerebral palsy, and so on. |
| AMCAP | Accepts mentally handicapped | | Accepts patients with mental handicaps, e.g. Down's syndrome, chronic mental illness. |
| ALIT | Accepts patients involved in litigation | | Provider will treat patients who currently involved with a medical litigation. |
| AHIV+ | Accepts patients with HIV and/or AIDS | | Provider will treat patients with known HIV/AIDS. |
| AGAY | Accepts gay or bisexual patients | | Provider will accept patients who have a gay or bisexual lifestyle. |
| ALEG | Accepts patients for legal purposes | | Provider will treat patients who may require legal testimony from the provider as as well as medical care. |

Payment

The Payment category allows you to specify payment options and ranges offered by the provider as the Criteria Type in the Provider Criteria window.

| Code | Description | Value | Definition |
|---|---|---|---|
| FREE | Free initial consultation | | Offers brief initial consultation free of charge. |
| CCARD | Accepts credit cards | | Payment for services can be on a credit card. |
| VISA | Accepts VISA | | Payment by VISA card accepted. |
| DISC | Accepts Discover | | Payment by Discover card accepted. |
| AMEX | Accepts American Express | | Payment by American Express |

| Code | Description | Value | Definition |
|---|---|---|---|
| MCARD | Accepts Mastercard | | card accepted. Payment by Mastercard accepted |
| CHOICE | Accepts Choice | | Payment by Choice accepted |
| PPLAN | Accepts payment plan) (>$500) | | If total cost of care is more than $500, provider will negotiate a payment plan. |
| UNINS | Accepts uninsured patients | | provider will see patients who do not currently have any medical insurance |
| ABLPAY | Accepts patients on ability to pay | | Provider will negotiate fees with the patient on an ability to pay basis. |
| NAV$ | New adult visit less than | integer | Allows you to specify the upper limit of the cost for a new office visit for an adult. Specify an amount using an integer only, e.g., 100. |
| NPV$ | New pediatric visit less than | integer | Allows you to specify the upper limit of the cost for a new office visit for a child. Specify an amount using an integer only. |
| EAV$ | Established adult office visit less than | integer | Allows you to specify the upper limit of the cost for a regular office visit by an adult. Specify an amount using an integer only. |
| EPV$ | Established pediatric office visit less than | integer | Allows you to specify the upper limit of the cost for a regular office visit by a child. Specify an amount using an integer only. |
| FAV$ | Follow-up adult visit less than | integer | Allows you to specify the upper limit of the cost for a follow-up visit for an adult Specify an amount using an integer only. |
| FPV$ | Follow-up pediatric visit less than | integer | Allows you to specify the upper limit of the cost for a follow-up visit for a child. Specify the amount using an integer only. |
| CONS$ | Second opinion/ consultation visit less than | integer | Allows you to specify the upper limit of the cost for a consultation visit to the provider. Specify an amount using an integer only. |

Health Plan

The Health Plan category allows you to specify the following codes as the Criteria Type in the Provider Criteria window:

health plan(s) in which the provider participates the role the provider plays with the health plan For example, the code PANEL indicates the provider serves on the panel with the health plan selected from the PLAN code list; the code GGATE indicates the provider is a designated gatekeeper for the health plan selected from the PLAN code list.

| Code | Description | Value | Definition |
|---|---|---|---|
| PLAN | Provider accepts health plan | list | Provider will accept patients with this specified health plan. |
| PANEL | Provider is "on panel" for plan | list | Provider is designated by the health plan as a panel provider. |
| GGATE | Provider is general Gatekeeper for plan | list | Provider is designated by the health plan as a "gatekeeper." |
| OBGATE | Provider is OB Gatekeeper for plan | list | Provider is designated by the health plan as an obstetrical "gatekeeper." |
| MCARE | Provider accepts Medicare | | Provider will accept patients covered through Medicare. |
| MCAID | Provider accepts Medicaid | | Provider will accept patients covered through Medicaid. |

Special Dental

The Special Dental category allows you to indicate characteristics that are specific to dental providers as the Criteria Type in the Provider Criteria window.

| Code | Description | Value | Definition |
|---|---|---|---|
| DCON$ | Initial consultation less than | integer | Allows you to specify the upper limit of the cost for a new office visit. Specify the amount using an integer only. |
| DEXAM$ | Complete exam less than | integer | Allws you to specify the upper limit of the cost of a complete exam. Specify the amount using an integer only. |
| DPRO$ | Routine prophylaxis (cleaning) less than | integer | Allows you to specify the upper limit for the cost of a routine cleaning. Specify the amount using an |

| Code | Description | Value | Definition |
| --- | --- | --- | --- |
| DDEL | Accepts Delta | | integer only. Provider accepts patients with dental coverage through Delta. |

Special Mental Health

The Special Mental Health category allows you to indicate specific details about the mental health providers as the Criteria Type in the Provider Criteria window.

| Code | Description | Value | Definition |
| --- | --- | --- | --- |
| NCHILD | Number of children the provider has | list | Allows you to specify the size of the provider's own family. |
| TDIR | Therapeutic Directness | list | Allows you to specify therapist's of participation in the therapy process. |
| TAPP | Therapeutic Approach | list | Allows you to specify the therapist's general approach to mental health issues. |
| DEG | Provider's professional degree | list | Allows you to indicate the degree the patient wishes the provider to have, e.g. Ph.D., Master's, CSW. |
| MCHRO | Accepts patients with chronic mental illness | | Allows you to find providers who will accept patients with diagnosed chronic mental illness. |
| MCDIS | Accepts children/teens with developmental problems | | Provider will accept childrem or teenagers with diagnosed developmental disorders. |
| ACOT | Accepts court ordered therapy | | Provider will accept patients for diagnosis/treatment that has been ordered by a court. |
| AM-COMP | Accepts medically compromised patients | | Provider will accept patients who have current medical conditions which may compromise their mental health treatment. |

Special Facility

The Special Facility category allows you to specify characteristics about a treatment facility as the Criteria Type in the Provider Criteria window.

| Code | Description | Value | Definition |
| --- | --- | --- | --- |
| ASSOC | Clinic Association | list | Allows you to specify a clinic affiliated with a facility. |
| CTYPE | Clinic Type | list | Allows you to indicate a particular type of clinic at a facility, e.g., a specialty clinic. |
| CFOCUS | Clinic Focus | list | Allows you to indicate what areas of treatment specialties the clinic treats, e.g., a burn clinic. |

ALGORITHM EDITOR

As shown in FIG. 1A, the NMS 11 includes an algorithm editor 100. The following description of the algorithm editor 100 provides an understanding of the capabilities of the editor and instructions for its use. Step-by-step suggestions for the development of a new algorithm and for the editing of an existing algorithm have been included The description is written for users who are not familiar with the Editor software. It is assumed however, that the user has a basic level of understanding and proficiency with basic word processing within a windows environment.

COMPONENTS OF THE EDITOR

This section of the description describes the purposes and uses of the major component parts of the Editor. It includes a discussion of:

The Menu Bar

Node Types and Purpose

The Directory Structure

It should be noted that the Editor uses a windowing system that allows for the manipulation of window placement and size which is the same as that for most "window" applications. It is assumed that the user is familiar with the standard procedures for the manipulation of windows, and no further explanation is provided in this manual. The creation and revision of algorithms requires an understanding of each of these component parts.

The Menu Bar

Figure 60:
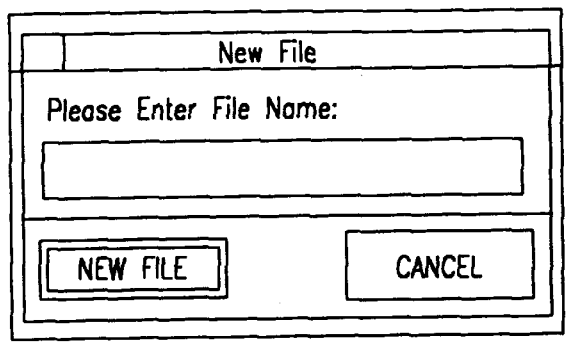
Figure 59:
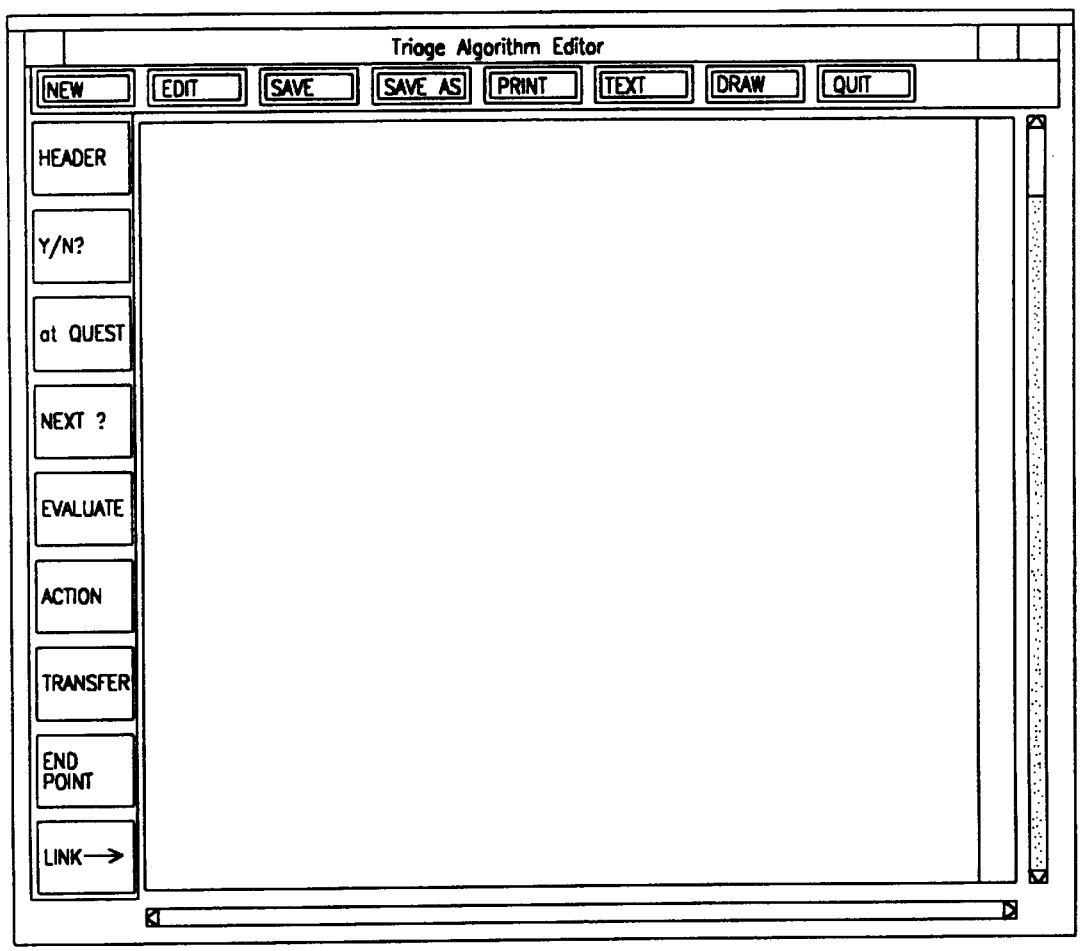

The Menu Bar is the array of Editor options (buttons) located horizontally at the top of the Editor window (see FIG. 59.). These options have various purposes, as follows:

The "NEW" button: This button is used initially for the creation of a new algorithm. When it is "clicked", a blank screen appears in the Editor window. In the upper left comer of the screen, a pop-up window (see FIG. 60.) appears on which you will need to enter the file name (or file number). (This will be described below in the "Creating a New Algorithm" section).

Figure 61:
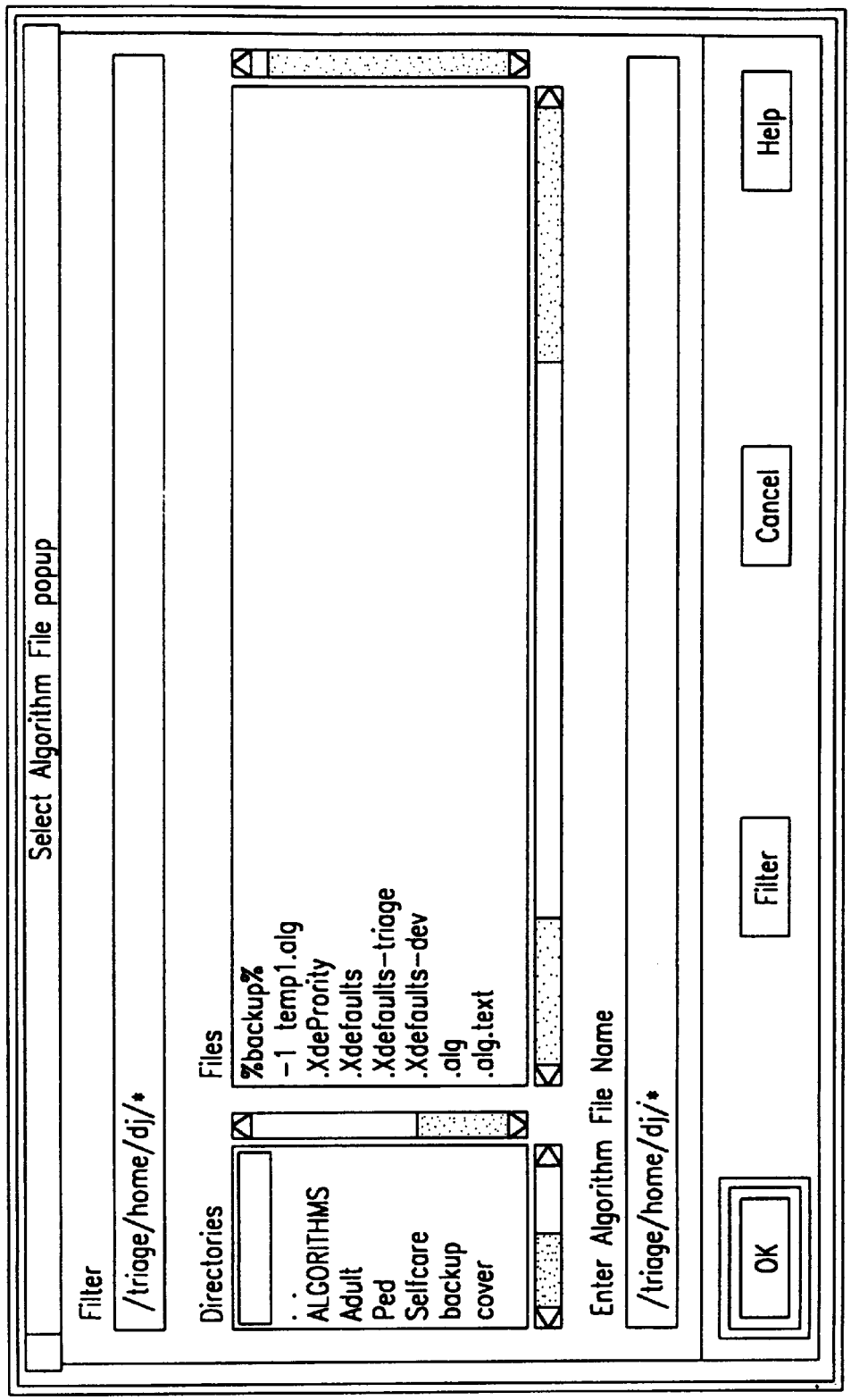

The "EDIT" button: This button is used to retrieve an existing algorithm that has been stored in one of the Editor directories. When it is "clicked", a pop-up window (see FIG. 61.) appears that allows you to select the directory and specific algorithm desired. This window "defaults" to the Home directory. Double-clicking on the desired directory (these are listed in the "directories" column) will retrieve the list of specific algorithm files stored in that directory. By clicking on the specific algorithm file desired and then "clicking" on the "OK" button in this pop-up window, the desired algorithm will appear in the Editor window. Clicking on the "Cancel" button in this pop-up window "cancels" your request, and the pop-up window disappears.

An explanation of the directory structure of the Editor is provided below.

Figure 62:
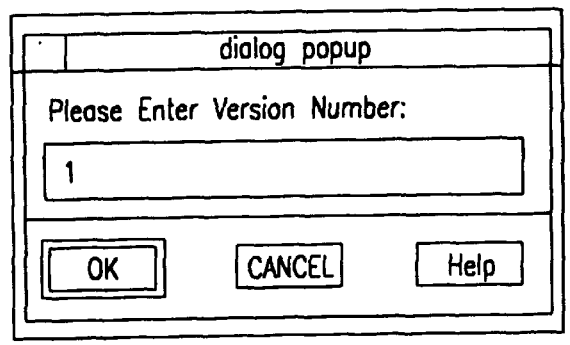

The "SAVE" button: This is the button used to "save" an algorithm file. It should be noted that THE EDITOR DOES NOT AUTOMATICALLY SAVE FILES as you are working on them. As a result, you will need to FREQUENTLY save any algorithm you are working on, to avoid losing your work When you "click" on this button, a pop-up window (see FIG. 62) appears with a request for you to enter the version number. For now, please type in 1 in this space, so that each algorithm has version 1 as its start-point. We will have to decide on how this will be used in the future, and its relation to other UNIX versioning systems. After entering 1 here, click on the "OK" button and the algorithm file is saved as version 1. The window automatically disappears and you are ready to continue working on the algorithm file.

The "SAVE AS" button: This button allows you to save a file that is currently in the Editor window under another name (or file name). It works almost identically to the "NEW" button (described above).

The "PRINT" button: This button was initially included to be able to "print-out" an algorithm file. However, given problems with the printing function, this button is currently inactive. Nothing happens when it is "clicked" and (for now) it should be disregarded.

Figure 63:
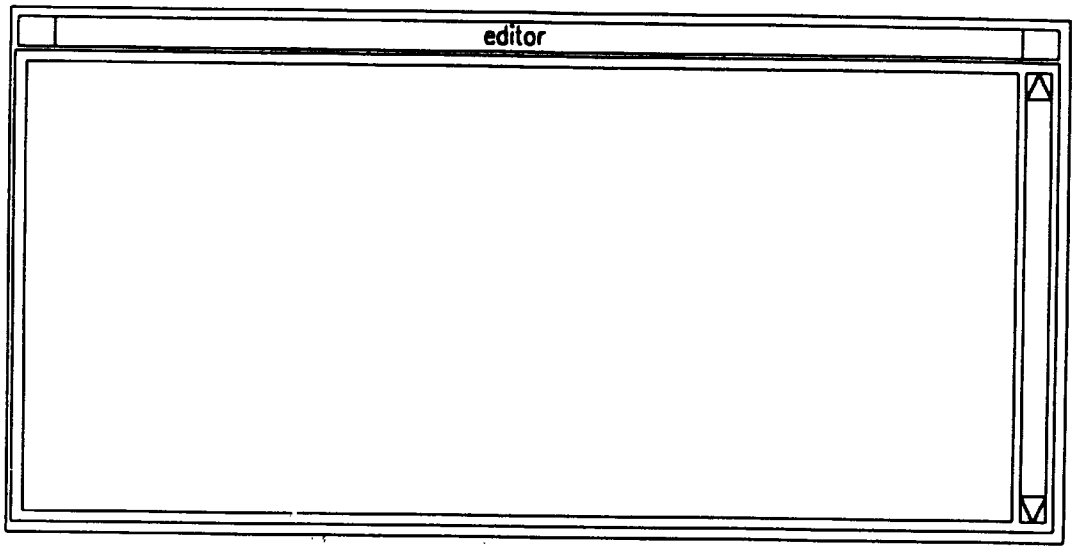

The "TEXT" button: This button allows you to write in any text comments about the algorithm that are stored within the algorithm itself. It should be used to enter the ALGORITHM SUMMARY text, which is the summary of the algorithm (we used to call this the "cover sheet") that the nurse sees prior to beginning an algorithm in the Nursetool. When you "click" on this button, a pop-up window (see FIG. 63) appears, into which text can be entered & Simply type in the desired summary of the algorithm here (the correct format and structure for this summary text will be determined later). The specific process for doing this is described in a later section (The Algorithm Summary).

Figure 64:
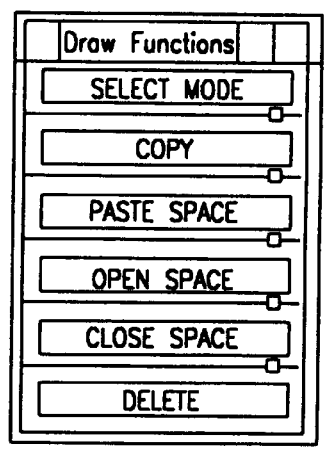

The "DRAW" button: This button provides access to virtually all of the editing functions that are included in the Editor software. When you "click" on this button, a pop-up menu (see FIG. 64) appears. This menu lists the various editing functions. The specific use of these functions is provided in a later section (Retrieving and Editing an Existing Algorithm).

The "QUIT" button: This button, when "clicked" exits you from the Editor. It should be used ONLY if you wish to leave the Editor. If you use this button at the end of your Editor session, YOU WILL LOSE ALL UNSAVED WORK THAT YOU HAVE COMPLETED. As a result, you should always save your work prior to using this button.

Node Types and Purposes

The development of an algorithm requires the use of a variety of "types" of nodes. These nodes appear as the "boxes" in the algorithm logic. This section will describe the various types of nodes available in the Editor and their different purposes and uses. These node types are arrayed vertically as "buttons" on the left side of the algorithm Editor window (see FIG. 59).

Each separate node type has an associated pop-up window, into which pertinent information is entered and stored. Each type of node has somewhat different fields of information to be entered, reflecting the node's purpose and use. It is this entered information that the nursetool "reads" in order to correctly place information in the relevant nursetool window. Thus, the information entered into each node is the "guts" of the system. More specific and detailed information for each type of node is provided below.

The HEADER Node: This node is the "title" node of the algorithm. It provides the name of the algorithm and a good share of the technical information required by the system to use it in the nursetool (see FIG. 65). The fields on information required in the header node are:

Algorithm Name

Algorithm Purpose

Algorithm Category

Related Algorithms

Keywords

The correct completion of these fields of information in the development of an algorithm will be described later (in "The Node Text").

The Y/N ? Node: This node is the major "Yes-No" node which displays the clinical questions to be asked of the patient. These questions are constructed in such a way as to force a Yes or No response from the patient. The majority of nodes in an algorithm are of this type. The fields of information that are stored with this node type (see FIG. 66) are as follows:

Clinical Question

Clinical Rationale

Lay Question(s)

Instruct Not Sure

Aux 1

The correct completion of these fields of information in the development of an algorithm will be described later (in "The Node Text").

The 1ST QUESTION Node:

The NEXT ? Node:

The EVALUATE Node:

These node types are described together because they are used as a "set". They are designed for situations where an algorithm asks a series of related questions that are linked together as a set and "scored". All questions in this series are asked of the patient (regardless of the patient's response). The Yes or No answer (for each question) is recorded and the "score" value is recorded. After the final question of the "set", the final "score" is tabulated and the call is routed on the basis of the patient's score. The 1st Question is used to indicate the FIRST question of this set. All remaining questions of the "set" are entered using the "Next ?" node type. Finally, the Evaluate nodes are used to indicate the desired recommendation, based on the caller's score. At present, these are very infrequently used in algorithms.

Figures 67, 68:
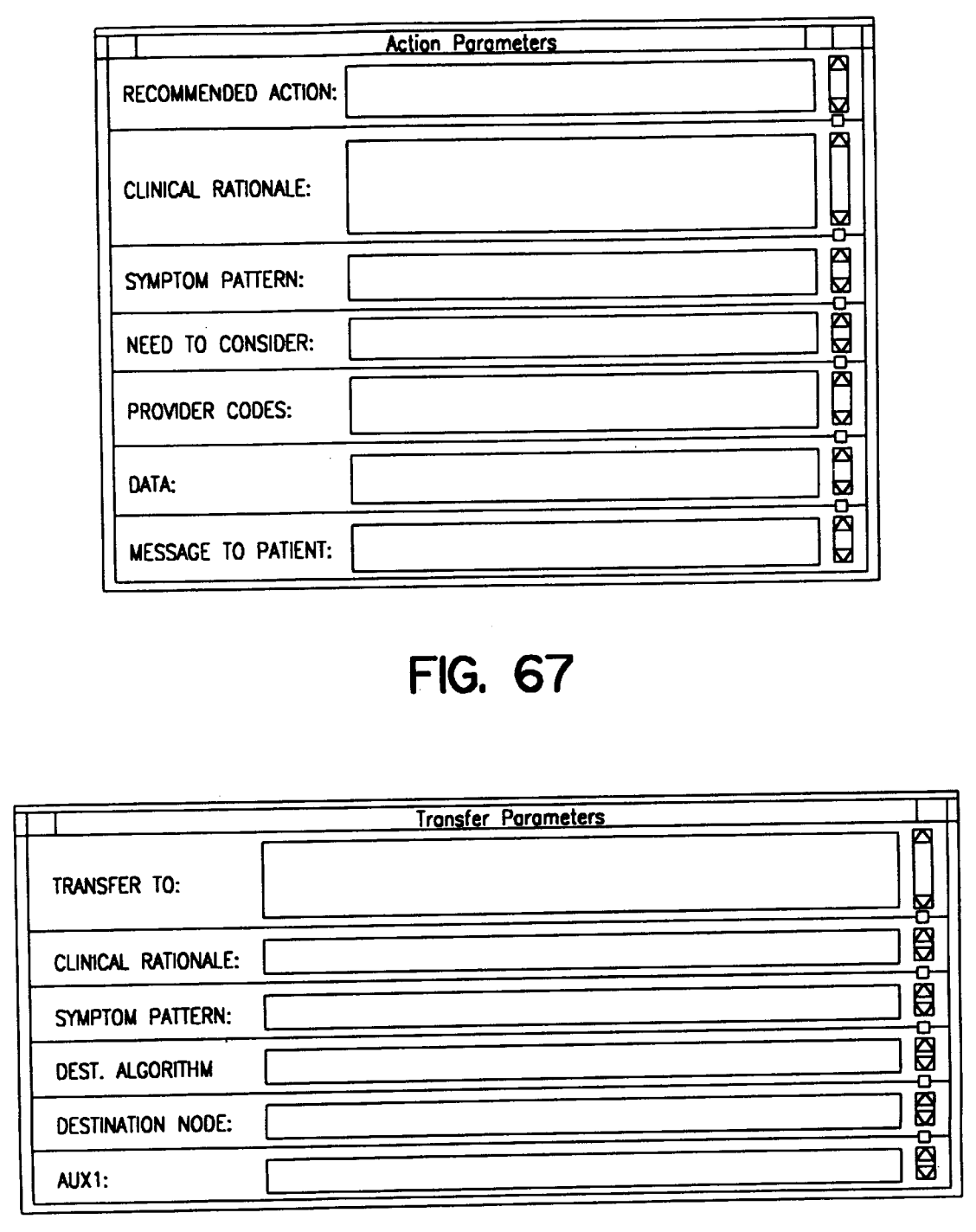

The ACTION Node: The Action node is a type of recommendation node. It provides a recommended action to take (e.g. Appointment, Self-care) based on the patient's response to Yes-No questions. This type of recommendation node is used when a recommended action is provided, but the algorithm developer wants the remaining questions of the algorithm to be asked before this recommendation is provided to the patient Thus, when an Action node is reached by a patient in the call process, the recommendation is recorded (for use at the end of the algorithm traversal) and the call is routed to the next Yes-No question of the algorithm The fields of information connected to this node type (see FIG. 67) are as follows:

Recommended Action

Clinical rationale

Symptom Pattern

Need to Consider

Provider Codes

Data

Message to patient

The correct completion of these fields of information in the development of an algorithm will be described later (in "The Node Text").

The Transfer Node: This node type is used to transfer the call immediately to a different algorithm. When a call routes to this type of node, it immediately "transfers" to the first question of the desired algorithm If desired, this node can also be used to transfer to a specific node in another algorithm (rather than the first question of that algorithm).

The fields of information connected to this node type (see FIG. 68) are as follows:
Transfer to:
Clinical rationale
Symptom Pattern
Dest. Algorithm
Destination Node
Aux1

The correct completion of these fields of information in the development of an algorithm will be described later (in "The Node Text").

The Endpoint Node: This is the second type of recommendation node. Like the ACTION node, it provides a recommended action to take (e.g. Appointment, Self-care) based on the patient's response to Yes-No questions. However, this type of node is used when the algorithm developer wants to provide the recommendation immediately, thus stopping any further questioning in the algorithm. The Endpoint node (when reached in the process of a call) will "end" the algorithm questioning and the recommendation will be provided to the patient.

The fields of information connected to this node type (see FIG. 69) are as follows:

Recommended Action
Clinical rationale
Message to patient
Symptom Pattern
Need to Consider
Provider Codes
Data The correct completion of these fields of information in the development of an algorithm will be described later (in "The Node Text ").

The Link Command: This final "button" in the left-hand vertical column of the Editor window is used to link the nodes together. When engaged, this command will allow the developer to draw narrowed lines between nodes to create the desired algorithm pathways. These linkage patterns are "read" by the system to prvide the correct "routing" of a call, based on the responses provided by the patient The correct use of this command function in the development of an algorithm will be described later (in "The Algorithm Logic", pps. 18–25).

The Directory Structure

The Editor has been designed to accommodate the many functions associated with the creation of an algorithm. In order to efficiently "store" the various files required for an algorithm, a directory structure has been created to organize files. This structure is as follows:

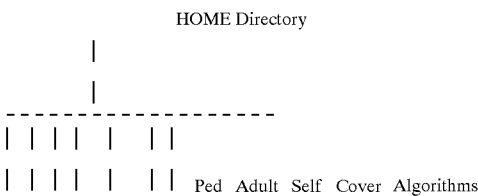

Self-Care bin

The HOME directory is your "parent" directory. All of the algorithms that are initially created are stored as their text name (e.g. PEDIATRIC__ASTHMA) in this directory. Once the algorithms are completed, edited and reviewed, the "official" versions are stored as their official UNIX file name in the Ped directory (for pediatric algorithms) or in the Adult directory (for adult and womens' health algorithms), as described below.

This file takes the form of either /home/<user> or /app/nursetool

The Ped directory houses all of the "official" Pediatric algorithms. The files have the Unix filenames P__V__.alg. This directory also houses the Algorithm Summaries associated with each algorithm. These files are stored as P__V__.alg.text files.

The Adult directory houses all of the "official" Adult algorithms (including the Womens' Health algorithms). The files have the Unix filenames
A__V__.alg (for Adult algorithms) and W__V__.alg for the Womens' Health algorithms. This directory also houses the Algorithm Summaries associated with each algorithm. These files are stored as P__V__.alg.text files.

The self directory houses all of the self-care files associated with the algorithm set. These are stored as their UNIX file name (e.g. P__S__A.001), indicating the algorithm to which each file is associated.

The cover directory houses all of the Cover Sheet files associated with the algorithm set. These are stored as their UNIX file name (e.g. P__V__.cvr), indicating the algorithm to which each Cover Sheet file is associated.

There are three (3) additional directories created for the system. These include:

Algorithms directory (this directory houses all of the algorithms that are currently loaded into the Nursetool);

Self Care directory (this directory houses all of the self-care files that are currently loaded into the Nursetool);

bin directory (this directory houses all of the "executable" files that allow for proper functioning of the software).
These Three Files Should not be Used by the Algorithm Developer The use of these various directories, especially for editing existing algorithms, will be discussed in a later section (Retrieving and Editing an Existing Algorithm).

USING THE EDITOR PROGRAM

This section of the description provides detailed instructions about the various common uses of the Editor software. It includes:
Accessing the Editor software:
Creating a New Algorithm
Retrieving an Existing Algorithm
Editing an Existing algorithm
Creating the Cover Sheet and Self-Care File(s)

Editing the Cover Sheet and Self-Care Files

Following these instructions will allow for the proper development and editing of algorithms for use with the Nursetool application.

Accessing the Editor Software

To make the Editor available for use, simply follow these instructions:

1. Once your UNIX station is "on" and has completed its booting process, you will see on the screen the log in prompt Simply type in the log in instructions provided separately to you.
2. Once the log in has been completed, depress and hold down the mouse "click" at any point on the blank screen. This will "show" your Root Menu. Without releasing the mouse "click" yet, scroll down the Root Menu to the Algo.Editor option and release the mouse.
3. Wait for a few seconds and the Editor window will appear on the screen. You are now ready to begin using the Editor.

NOTE: If, for some reason, your Root Menu does not seem to work, an alternate method of invoking the Editor can be used as follows:

1. After properly completing log in (as described above), you will see a "xterm" icon in the lower left corner of the screen.
2. Double-click on this icon, and a large, empty window will appear with a % prompt.
3. at this prompt, type in editor and return.
4. Wait for a few seconds and the Editor window should appear on the screen.

Creating a New Algorithm:

For development purposes, an algorithm is considered to have five (5) basic components. These include the following:

The Algorithm Logic

The Node Text

The Algorithm Summary

The Cover Sheet

The Self-Care File(s)

Three (3) of these components should be completed within the Editor itself (the Algorithm Summary, the Algorithm logic, the Node Text). The remaining components (The Cover Sheet, the Self-Care File(s) should be completed (if possible) in the system (workstation), but outside of the specific Editor program. Specific instructions for the creation of these non-Editor components of an algorithm will be provided later (Creating the Cover Sheet and Self-Care files).

TASK 1: Creating the Algorithm Logic

The first task to complete in the creation of an algorithm in the Editor is to develop the algorithm logic structure. Before beginning to create the logic, the following "set-up" should be helpful.

Enlarge the Editor window (horizontally) so that the heavy, black vertical line appears on the far-right section of the Editor window. This line marks the right-hand "boundary" of the editor window. DO NOT ENTER ANYTHING TO THE RIGHT OF THIS LINE.

Enlarge the Editor window vertically so that it covers the entire length of the screen. This will give you a larger working area.

Move the Editor window to the right-hand half of the screen.

You are now ready to begin creating the algorithm logic.

Step 1: Create the File.

Click on the "New" button in the Menu bar. This will cause the "NEW" pop-up window to appear. In the pop-up window, enter the "official" text name of the algorithm, EXACILY AS IT APPEARS on the algorithm control sheet This file name should be in ALL CAPITAL LETTERS, with underscores (separating each word in the file name. DO NOT TYPE IN ANY SPACES OR HIT THE "RETURN" KEY ON THE KEYBOARD after entering the file name.

When completed correctly, click on the "New File" button. A new file with this algorithm name has now been created, and the pop-up window disappears. FIG. 70 provides an example of this process.

Step 2: Enter The Header Node

Click on the Header node option. The Header parameter window will appear.

In the "algorithm name" field, enter the Official algorithm name (this will be the same name that you just entered in Step 1 above). Simply "click" anywhere in this field, and begin typing the name. IT MUST BE TYPED IN CORRECTLY as described above, without any typos.

Now move the mouse pointer to the top-center of the Editor window (You may have to move the Header Parameter window). Click at the spot where you would like the Header node to appear. Note that the "box" appears in the Editor window. Click again on the box, and the Algorithm name will appear in the box.

The Header node is now entered in the Editor window.

Step 3: Enter the Y/N ? Nodes

After completion of the Header node, all algorithms begin with the first Yes/No question.

Click on the Y/N ? button. The "Yes/No Question Parameters" window will appear on the screen.

Now move the mouse pointer to the spot on the algorithm window where you would like to position the first question. (You may have to first "move" this pop-up window). It is recommended that you position this first question at the left-hand side of the Editor window, slightly below the level of the Header Node. Position the mouse pointer to the approximate spot where you would like the upper left corner of this box to appear in the Editor window.

Click on the mouse, and the Yes/No node box will appear in the window. The "Yes/No Parameters" window will move into the background. Now click anywhere on the "Parameters" window to move it into the forefront. Click anywhere on the "Clinical Question" field. Type in the clinical question desire& Move the pointer back to the "box" and click on it. The clinical question should now appear in the box. Follow this same procedure for each Yes/No question of the algorithm Step 4: Enter the Recommendation Nodes When the desired algorithm traversal leads to an "algorithm recommendation", use the following procedure to create these "boxes" in the Editor window. Remember that there are two (2) basic types of algorithm recommendation nodes: Action nodes and Endpoint nodes. Action nodes should be used when the algorithm developer wishes further questioning in the algorithm to continue after this node is reached Endpoint nodes should be used when the algorithm developer wishes the algorithm traversal to stop after this node is reached. It is very important to use the correct node type here, as it affects the use of the algorithm by nurses and patients.

For the sake of convention, it is recommended that all algorithm recommendations be "placed" in the far right-hand portion of the Editor window. Here's the recommended process:

Click on the desired recommendation node window (ACTION or ENDPOINT). The appropriate "Parameters" window will appear on the screen.

Also note that another pop-up window "Recommendation Codes" appears in the upper left-hand corner of the screen.

Move the mouse pointer to the spot on the algorithm window where you would like to position the recommendation "box". (You may have to first "move" the "Parameters" window). Position the mouse pointer to the approximate spot where you would like the upper left corner of this box to appear in the Editor window. Click on the mouse, and the Recommendation node box will appear in the Editor window. The "Parameters" window will move into the background.

Now click anywhere on the "Parameters" window to move it into the forefront. Move the mouse pointer to the "Recommendation Codes" window (upper left corner of the screen). Select the desired recommendation by "clicking" on the appropriate menu item. Move the pointer back to the Editor window (anywhere) and desired recommendation should now appear in the box.

Follow this same procedure for each Recommendation Node associated with the algorithm.

Step 5: Enter the Transfer Node(s)

Transfer nodes are used when the algorithm developer desires that the call process be "transferred" to a different algorithm. When the desired algorithm traversal leads to a "Transfer" node, use the procedure described below to create these "boxes" in the Editor window.

There are two (2) basic types of Transfer options: Transfer nodes and Action nodes that recommend a transfer to another algorithm Action nodes (selecting the "transfer to algorithm" option in the Recommended Codes menu) should be used when the algorithm developer wishes further questioning in the current algorithm to continue after this node is reached. In this case, the transfer to another algorithm occurs after completion of the current algorithm. Transfer nodes should be used when the algorithm developer wishes the algorithm transfer to occur i m mediately after this node is reached. It is very important to use the correct node type here, as it affects the use of the algorithm by nurses and patients.

For the sake of convention, it is recommended that all transfer recommendations be "placed" in the far right-hand portion of the Editor window. Here's the recommended process:

Click on the desired recommendation node window (ACTION or TRANSFER). The appropriate "Parameters" window will appear on the screen.

For Action nodes requesting a transfer, note that another pop-up window "Recommendation Codes" appears in the upper left-hand corner of the screen.

Move the mouse pointer to the spot on the algorithm window where you would like to position the Transfer "box". (You may have to first "move" the "Parameters" window). Position the mouse pointer to the approximate spot where you would like the upper left corner of this box to appear in the Editor window. Click on the mouse, and the node box will appear in the Editor window. The "Parameters" window will move into the background. Now click anywhere on the "Parameters" window to move it into the forefront. For Action nodes requesting transfer, move the mouse pointer to the "Recommendation Codes" window (upper left corner of the screen).

Select the "Transfer to algorithm " recommendation by "clicking" on the appropriate menu item. Move the pointer back to the Editor window (anywhere) and desired recommendation should now appear in the box.

For Transfer nodes, click on the TRANSFER button of the Editor window.

The "Parameters" window will appear. Move the mouse pointer to the spot on the algorithm window where you would like to position the Transfer "box". (You may have to first "move" the "Parameters" window). Position the mouse pointer to the approximate spot where you would like the upper left corner of this box to appear in the Editor window. Click on the mouse, and the node box will appear in the Editor window. The "Parameters" window will move into the background.

Now click anywhere on the "Parameters" window to move it into the forefront. Click on the "Transfer to:" field. Type in this field Transfer to <algorithm name> algorithm. Since this field is NOT used by the Nursetool, the entry here does not have to follow a precise convention. Now move the mouse pointer back to the Transfer box in the Editor window and click on it.

The text Transfer to <algorithm name> algorithm should appear in the box.

Follow this same procedure for each Transfer Node associated with the algorithm.

Figure 71:
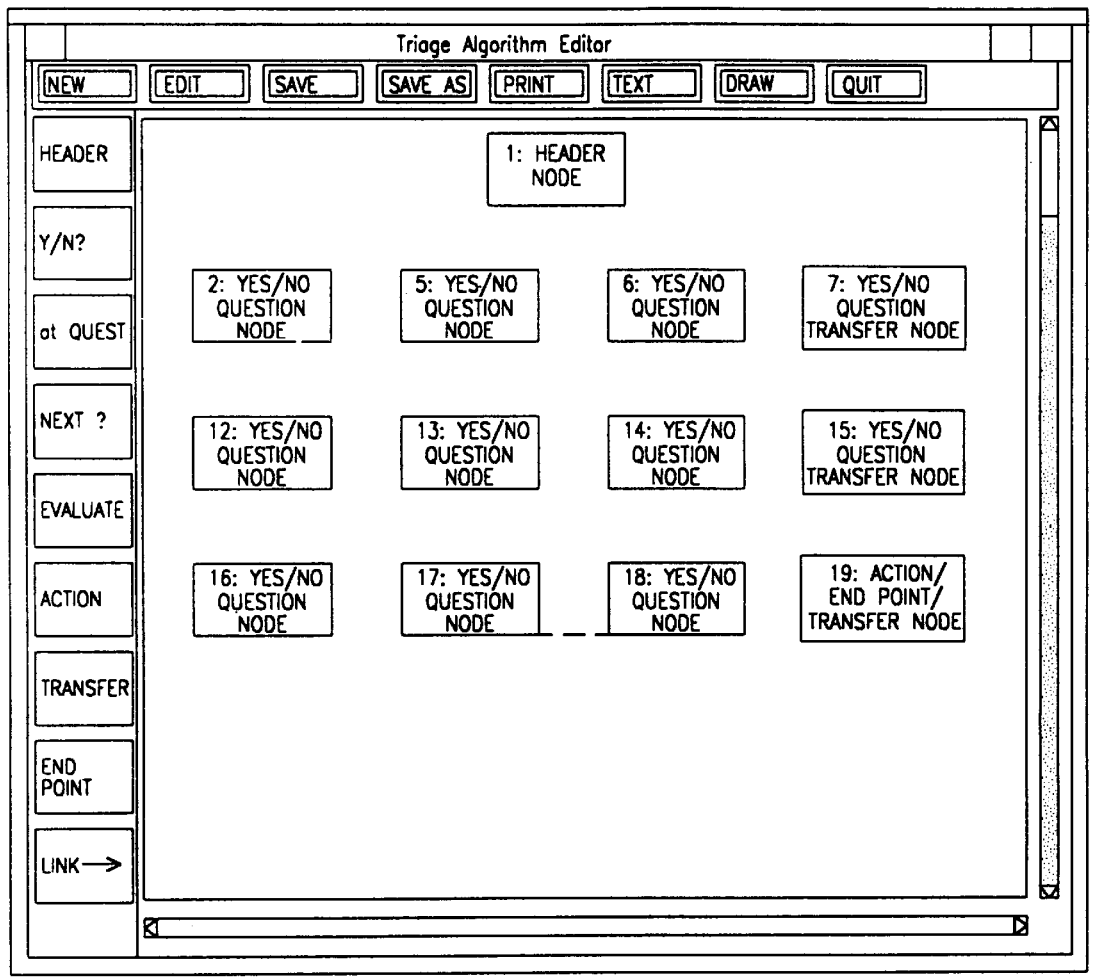

FIG. 71 provides the recommended arrangement of nodes.

Step 6: Linking the Algorithm Nodes (Boxes)

After the initial Editor window has been filled with nodes (see FIG. 13), the nodes must be properly "linked" to define the desired traversal of the algorithm, based on the responses to the algorithm questions. THESE LINKAGES MUST BE MADE CORRECTLY, as the system "reads" them in order to retrieve questions and recommendations in the desired order.

The "RULES" for correct linkages are as follows:

For Y/N ? nodes, each node must have two (2) links leaving the node (a "yes" link and a "No" link). The FIRST linkage made out of a Y/N ? node will be the "YES" path, the second link out of a Y/N ? node will be the "NO" path. These linkages are automatically identified as such.

For the HEADER node, all ACTION nodes, and the 1ST Question and NEXT Question nodes, the system only allows for one (1) link out of the node.

For all TRANSFER and ENDPOINT nodes, no linkage out of the node is possible.

To make the linkages, click on the "LINK" button of the Editor window. Move the mouse pointer to the node (box) FROM which the linkage is to be made. Depress and hold down the "clicker" of the mouse and move the mouse horizontally or vertically to the node that you wish to link This does not have to be a precise process. Simply begin the link somewhere within the originating node (box) and complete the link (by releasing the mouse) somewhere inside the destination node (box).

Note that the LINK function allows for Tight-angle turns (these are often necessary). This is done by moving the mouse as far as desired (but not within another node or across a separate linkage), then releasing the "click", then depressing and holding it again, now moving it in one of the two directions that is a right-angle to the initial linkage. While this sounds difficult, it is really very easy to learn and master quickly.

The LINK function will also allow for a linkage from a node (box) to a separate link. Simply follow the instructions provided above and "link" to a different, already existing linkage line by passing through it and the releasing the mouse. It will then "link" to the line, following the route taken by this initial linkage.

Figure 72:
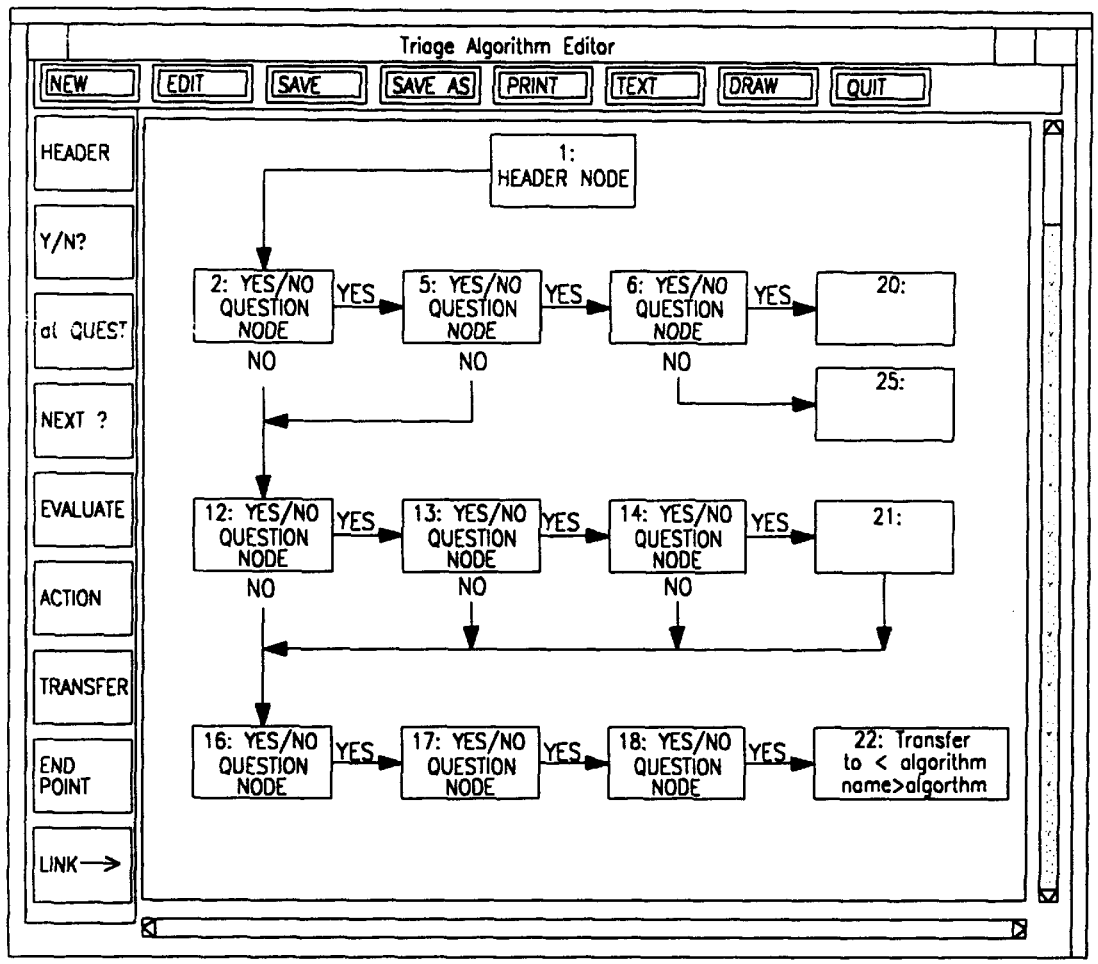

See FIG. 72 for an example of the completed linkage process.

Step 7: General Considerations

In terms of the general layout of the algorithm, it is recommended that the algorithm logic be constructed in a manner similar to that depicted in FIG. 72. This will allow for some degree of uniformity and makes it easier to edit and review the algorithms.

Some general thoughts are provided as follows:

1. The width of the Editor window allows for the placement of no more than 5 "boxes" horizontally placed in the same row. So far, there have been only a few circumstances where the progression from a stem question to a transfer or recommendation node in a single row has exceeded this number.

2. When more space is required (length-wise) for the completion of the algorithm, simply place the mouse pointer on the scroll bar (the right-hand margin of the Editor window), depress and hold the mouse in the down position, and gradually drag the mouse downward. This will provide any additional space required.

3. Remember that the Editor software DOES NOT SAVE YOUR WORK AUTOMATICALLY. YOU MUST SAVE YOUR WORK OF TEN TO AVOID LOSING IT.

4. As you create individual nodes, you will see them identified in the Editor window with numbers that precede the text for that node. These numbers are generated automatically by the Editor and represent the official node IDs for each node in each algorithm You do not have any control over this process. The nodes are automatically numbered in the order of their creation. Thus, it is probably smart to have a good idea of the basic layout of the algorithm prior to creating it on the Editor.

Task 2: Entering the Node Text

The second major task associated with the creation of a new algorithm is the proper entry of algorithm node data This involves the completion of all relevant fields of information in the "Parameter" window that is "attached" to the individual node. The following section describes the purpose and proper completion of each of the fields of information.

Once the "logic" of the algorithm has been correctly entered into the system, the algorithm developer needs to complete the information requested for each node.
ALL NODE TYPES REQUIRE THE COMPLETION OF SOME AMOUNT OF ASSOCIATED INFORMATION.
Step 1: Enter The Header Node Data To properly complete the data associated with the header Node, complete the following process:

Click on the Header node to make the "Parameter" window appear on the screen. The "Algorithm Name" field has already been completed. (Step 2 in Task 1 above).

Click anywhere on the "Purpose" field. Enter the purpose of the algorithm here. This should be a short, concise description of the focus of the algorithm. Try to make this entry 1 line long if possible, so that it is easy to read by the nurses in the nursetool.

Click anywhere in the "Category" field. Enter the correct category of this algorithm (this is also provided on the algorithm control sheet). The category MUST BE TYPED EXACTLY AS IS APPEARS ON THE CONTROL SHEET. The system will not "read" misspellings, wrong capitalization, etc. DO NOT ENTER A SPACE, OR USE THE RETURN BAR OF THE KEYBOARD AFTER ENTERING THE CATEGORY, Doing so will also make the category name unusable to the Nursetool.

Click anywhere in the "Related Algorithms" field. This field will include all algorithms that are "related" in some way to the current algorithm. The intent here is to enter any and all algorithms that might be a better selection for the nurse than the one being developed. This is one way to assist the nurse in selecting the most appropriate algorithm to be used. Enter the EXACT, OFFICIAL ALGORITHM FILE NAME(S) HERE. AFTER EACH ALGORITHM NAME ENTERED, PRESS THE RETURN KEY ON THE KEYBOARD so that each algorithm name is on a separate line. MAKE SURE THAT YOU ALSO PRESS THE RETURN KEY ON THE KEYBOARD AFTER ENTERING THE LAST ALGORITHM.

Click anywhere on the "keywords" field. Type in any keywords that you would like to associate with this algorithm. The purpose here is to provide the content for a keyword search which can be used by the nurse in the selection of the appropriate algorithm. KEYWORDS SHOULD BE ENTERED IN lower case. SEPARATED BY A SEMI-COLON. If the keyword is more than 1 word, separate these words by a hyphen (-) DO NOT SKIP ANY SPACES WITHIN OR BETWEEN KEYWORDS.

Figure 73:
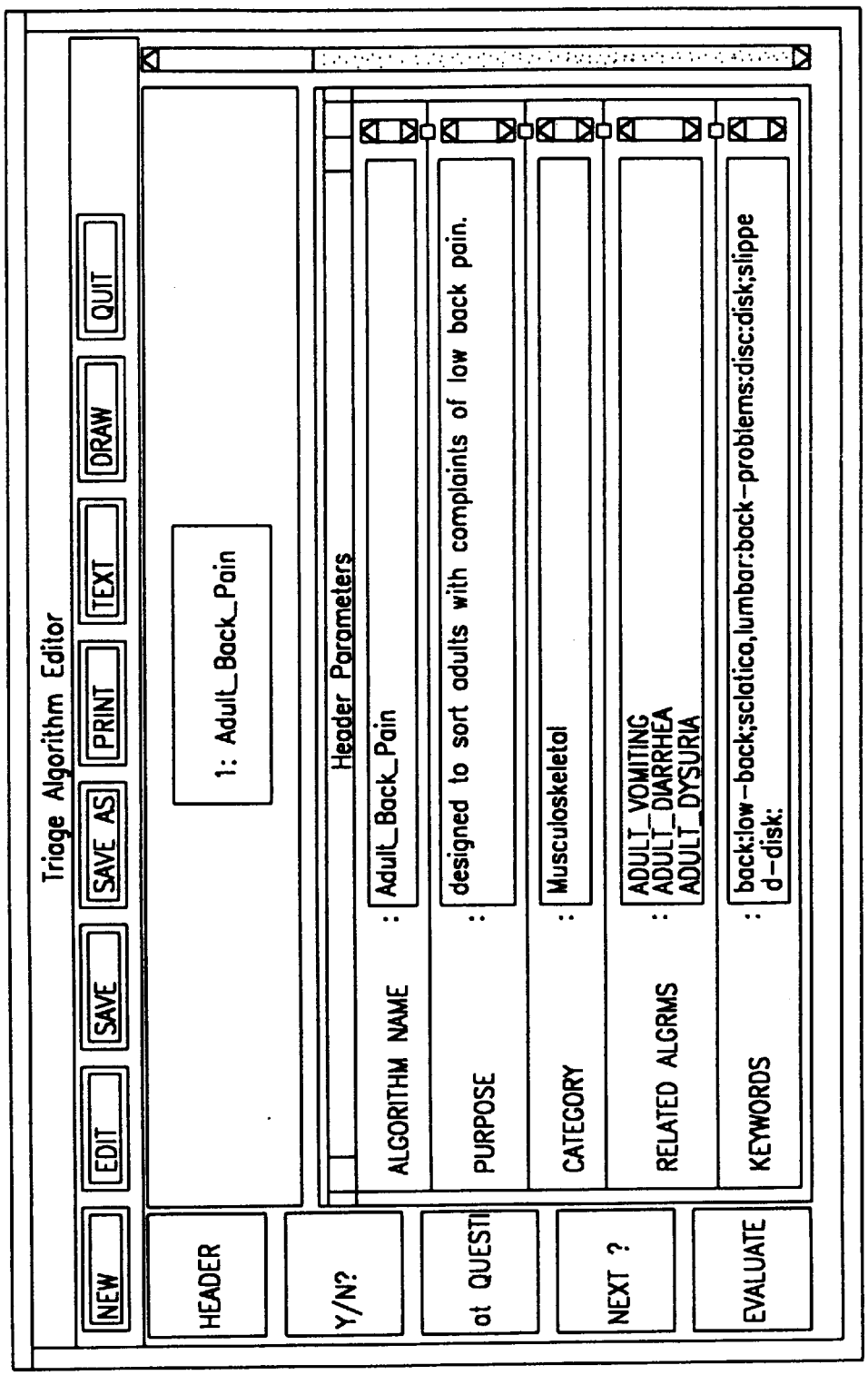

An example of a correctly completed Header node is provided in FIG. 73.

Step 2: Enter the data for all Y/N ? nodes.

To properly complete the data associated with each Y/N? node, complete the following process.

Click on the desired Y/N / node to make the "Parameter" window appear on the screen. The "Clinical Question" field has already been completed (Step 3 in Task 1 above).

Click anywhere on the "Clinical Rationale" field. Enter here the rationale for asking the question at this point in the algorithm. It is provided to assist the nurse, if necessary, in the understanding of the reason for the question and the likelihood (or estimated probability) of a "YES" response to the clinical question. This should be a reasonably short, concise description of the purpose of the question. This should also tie back to the "Specific Conditions Considered" section of the Cover Sheet. An example of a correct format here would be: "Benign stomach aches usually do not get "worse and worse". If present, this could be an indication of peritonitis or obstruction."

Peritonitis: Rare

Obstruction: Extremely Rare

Click anywhere in the "Lay Question(s)" field. Enter the suggested "lay" version(s) of the associated clinical question. These are provided to assist the nurse in formulating the question to the patient. The lay question(s) should also be brief, concise, and written in lay language.

Click anywhere in the "Instruct Not Sure" field. This field will include any additional instructions or suggestions to the nurse if the nurse is uncertain of the patient's response, or if the patient is unable to answer the question with a "YES" or a "NO". The intent here is to provide additional support to the nurse. This field can also be used to provide additional information to the nurse about the question or the issue.

Note that the "Auxilliary2" field is not currently being used The field is included to in the event that an additional field of information is deemed important to collect If relevant, this is a good place to insert any key references or other documentation about the specific question or issue being addressed. If there are no references to insert, it can be left blank.

An example of a correctly completed Y/N ? node is provided in FIG. 74.

Step 3: Enter the Data for all ENDPOINT Nodes

To properly complete the data associated with each ENDPOINT node, complete the following process:

Click on the desired ENDPOINT node to make the "Parameter" window appear on the screen. The "Recommendation" field has already been completed. (Step 4 in Task 1 above).

Click anywhere on the "Clinical Rationale" field. Enter here the rationale for this particular recommendation at this point in the algorithm. This rationale is provided to assist the nurse, if necessary, in the understanding of the reason for the recommended action. This should be a reasonably short, concise description clinical issue(s) of concern at this point in algorithm traversal. Click anywhere in the "Message to Patient" field. Enter the suggested "lay" version(s) of the key point(s) for the nurse to communicate to the patient in the offering of this recommendation. If possible, try to limit this field to 4 lines, so that scrolling won't be necessary in the Nursetool. Recommendations for the specific language to use here for each of the individual types of Endpoints/Action Nodes is provided in Appendix B of this document.

Click anywhere in the "Symptom Patter" field. Enter into this field a brief description of the path that the patient has taken in the traversal to this Endpoint.

Click anywhere on the "Need to Consider" field. Enter into this field a listing of the clinical concern(s) associated with this endpoint that may require further evaluation (in the event of a recommendation for medical intervention for the patient). This list should include all major clinical concerns that need to be ruled out with a higher level of medical intervention.

For an endpoint recommending SELF-CARE INSTRUCTIONS, this field should include information consistent with the algorithm cover sheet as well as with the "clinical rationale" of the preceding Y/N question.

If possible, try to make this section no more than 3 lines long, to avoid the need to "scroll" when using the Nursetool.

Click anywhere in the "Provider Codes" field. Enter into this field any recommended clinical or procedural codes that should be used in the selection of a provider for this symptom pattern/situation. As much as possible, try to use codes that are listed on the "Official" Clinical and Procedural Codes Listing that you should have previously received. The correct convention for entering provider codes is as follows:

On the FIRST line of this field, type in the EXACT code number for the desired provider code followed by a comma (,) followed by the "expertise level" (1–4) desired, ended by a semicolon (;). If more than 1 code is desired, type in each additional code ON THE SAME LINE following the same format. DO NOT ENTER ANY SPACES WITHIN OR BETWEEN CODES ON THIS LINE. MAKE SURE THAT THE LAST CODE NUMBER ENTERED ON THIS LINE IS FOLLOWED BY A SEMICOLON. Otherwise, the system will not properly read the desired code.

After entering all desired code numbers, hit the "Return" key of the keyboard. This takes you to the next line. On this line, enter the correct code name (matching the first code number entered on the line above). If there are more than 1 codes to be recommended here, hit the "Return" key after each code name (so that each one appears on a separate line). MAKE SURE THAT YOU HIT THE "RETURN" KEY AFTER ENTERING THE LAST CODE NAME. The system "reads" these carriage returns to properly display them in the Nursetool.

If the ENDPOINT Node recommends "SELF-CARE INSTRUCTIONS", click on the "Data" field. Enter in this field the OFFICIAL name of the desired self-care instructions file to use in this situation. This OFFICIAL version is located on the algorithm Control Sheet. DO NOT TYPE IN A SPACE, OR HIT THE RETURN KEY ON THE KEYBOARD AFTER ENTERING THE SELF-CARE FILE NAME. This will make the instruction inaccessible to the system.

For all other types of ENDPOINT recommendations, leave this field blank.

An example of a correctly completed ENDPOINT node is provided in FIG. 75.

Step 4: Enter the Data for all ACTION Nodes.

To properly complete the data associated with each ACTION node, complete the following process:

Click on the desired ACTION node to make the "Parameter" window appear on the screen. The "Recommended Action" field has already been completed (Step 4 in Task 1 above).

Click anywhere on the "Clinical Rationale" field. Enter here the rationale for this particular recommendation at this point in the algorithm This rationale is provided to assist the nurse, if necessary, in the understanding of the reason for the recommended action. This should be a reasonably short, concise description clinical issue(s) of concern at this point in algorithm traversal.

Click anywhere in the "Symptom Pattern" field. Enter into this field a brief description of the path that the patient has taken in the traversal to this Action node.

Click anywhere on the "Need to Consider" field. Enter into this field a listing of the clinical concern(s) associated with this recommended action that may require further evaluation (in the event of a recommendation for medical intervention for the patient). This list should include all major clinical concerns that need to be ruled out with a higher level of medical intervention.

For an action node recommending SELF-CARE INSTRUCTIONS, this field should include information consistent with the algorithm cover sheet as well as with the "clinical rationale" of the preceding Y/N question.

If possible, try to make this section no more than 3 lines long, to avoid the need to "scroll" when using the Nursetool.

Click anywhere in the "Provider Codes" field. Enter into this field any recommended clinical or procedural codes that should be used in the selection of a provider for this symptom pattern/situation. As much as possible, try to use codes that are listed on the "Official" Clinical and Procedural Codes Listing that you should have previously received. The correct convention for entering provider codes is as follows:

On the FIRST line of this field, type in the EXACT code number for the desired provider code followed by a comma (,) followed by the "expertise level" (1–4) desired, ended by a semi-colon (;). If more than 1 code is desired, type in each additional code ON THE SAME LINE following the same format. DO NOT ENTER ANY SPACES WITHIN OR BETWEEN CODES ON TIES LINE. MAKE SURE THAT THE LAST CODE NUMBER ENTERED ON THIS LINE IS FOLLOWED BY A SEMI-COLON. Otherwise, the system will not properly read the desired code.

After entering all desired code numbers, hit the "Return" key of the keyboard. This takes you to the next line. On this line, enter the correct code name (matching the first code number entered on the line above). If there are more than 1 codes to be recommended here, hit the "Return" key after each code name (so that each one appears on a separate line). MAKE SURE THAT YOU HIT THE "RETURN" KEY AFTER ENTERING THE LAST CODE NAME. The system "reads" these carriage returns to properly display them in the Nursetool.

If the ACTION Node recommends "SELF-CARE INSTRUCTIONS", click on the "Data" field. Enter in this field the OFFICIAL name of the desired self-care instructions file to use in this situation. This OFFICIAL version is located on the algorithm Control Sheet. DO NOT TYPE IN A SPACE, OR HIT THE RETURN KEY ON THE KEYBOARD AFTER ENTERING THE SELF-CARE FILE NAME. This will make the instruction inaccessible to the system.

For all other types of ACTION recommendations, leave this field blank.

Click anywhere in the "Message to Patient" field. Enter the suggested "lay" version(s) of the key point(s) for the nurse to communicate to the patient in the offering of this recommendation. If possible, try to limit this field to 4 lines, so that scrolling won't be necessary in the Nursetool. Recommendations for the specific language to use here for each of the individual types of Endpoints/Action Nodes is provided in Appendix B of this document.

An example of a correctly completed ACTION node is provided in FIG. 76.

Step 5: Enter the Data for all TRANSFER Nodes.

Only a minimal amount of information is required for entry into a Transfer node. The process is as follows:

Click on the desired TRANSFER node to make the "Parameter" window appear on the screen. The "Transfer to:" field has already been completed (Step 5 in Task 1 above).

Click on the "Clinical Rationale" field. Enter here a brief description of the reason for the transfer to a different algorithm.

Click anywhere on the "Dest. Algorithm" field. Enter here the OFFICIAL NAME of the algorithm to which the transfer is desired. This algorithm name MUST BE ENTERED EXACTLY AS IT APPEARS ON THE ALGORITHM CONTROL SHEET. It is this field that the system "reads" to successfully completed the desired transfer. If the name is entered incorrectly, the transfer cannot occur properly. DO NOT TYPE IN A SPACE. OR HIT THE RETURN KEY ON THE KEYBOARD AFTER ENTERING THE ALGORITHM NAME. This will make the instruction inaccessible to the system.

In some circumstances, the algorithm developer will desire the transfer to another algorithm to a specific node in the destination algorithm. Unless otherwise specified, all transfers will route to the first algorithm question of the destination algorithm. If the developer would like the transfer to a different node in the destination algorithm, the Destination Node field in the "Transfer Parameters" window must be completed. This is done by simply entering the specific destination algorithm node number to which the transfer is desired.

For now, there is no need to complete the other fields of data in the Transfer Parameters window, since these are never "seen" by the nurse.

An example of a correctly completed TRANSFER node is provided in FIG. 77.

Step 6: General Considerations

In terms of the general process for completing the node data of the algorithm, it is recommended that the steps provided above be followed in sequential order. By completing the node data for all Y/N ? nodes then for all Endpoint nodes, then for all Action nodes, and finally for all Transfer nodes, the developer will minimize the need to constantly move windows around to make them easily accessible.

Some general thoughts are provided as follows:

1. It is important to attempt to enter all data into the Editor as carefully as possible, avoiding grammatical errors and misspellings. These entries are "read" into the Nursetool exactly as they are entered. Reviewing the entered data periodically thus becomes essential.

2. Remember that the Editor software DOES NOT SAVE YOUR WORK AUTOMATICALLY. YOU MUST SAVE YOUR WORK OFTEN TO AVOID LOSING IT.

Task 3: Developing the Algorithm Summary

The Algorithm Summary is a very brief "summary" or overview of the algorithm. This summary automatically appears to the nurse in the Nursetool application after the selection of an algorithm has been made, but before the initial algorithm question. The Algorithm Summary is provided to the Nurse to quickly advise of the purpose, length, general structure and anticipated distribution of outcomes (or endpoints).

To properly complete the Algorithm Summary in the Editor, follow these instructions:

Click on the "TEXT" button of the Editor Window menu bar. a large, unstructured text window will appear.

Enter the Algorithm Summary by typing in, and formatting, the desired text. Try NOT to exceed 22 total lines for this Summary, so that the entire Summary will appear in the relevant Nursetool window, precluding the need for the nurse to "scroll" this Nursetool window.

Note that this process automatically gives this file its correct UNIX file name and extension, indicating its "linkage" to the algorithm being developed. The Summary will be "stored" in this text window, and can be edited at any time by opening the TEXT window.

An example of a correctly completed Algorithm Summary is provided in FIG. 78.

All of the necessary steps have now been completed in the creation of a new algorithm within the Editor. The algorithm file is now ready for review and editing (if necessary). However, two (2) additional steps are necessary for the algorithm to be completed entirely. These steps are:

Completing the Algorithm Cover Sheet, and;
Completing all relevant self-care files associated with the algorithm.

The completion of the algorithm Cover Sheet is to be done outside of UNIX, preferably in WordPerfect. This process is described below. The completion of Self-Care files should be done in UNIX (on your workstation) and will be described in the next section.

The process of completing these tasks is provided below.

Task 4: Completing the Algorithm Cover Sheet

The Algorithm Cover Sheet is the document that provides a detailed clinical analysis of the medical complaint for which the algorithm has been developed. It is recommended that the Cover Sheet be completed in WordPerfect. This document is prepared primarily for algorithm developers and reviewers (internal and external). As such, it simply needs to be printed-out for review and revision, but is not a document that is used in the Nursetool. As a result, it does not have to be completed in UNIX.

An example of a correctly-completed Algorithm Cover Sheet is provided in the appendix to this application.

Task 5: Complete the Self-Care File(s)

Self-Care files provide complete, clinically-valid instructions for home-care of the patient's complaint. When clinically indicated, these instructions are provided to the patient as the most appropriate level of intervention for the specified complaint Each Endpoint and/or Action node of the algorithm will suggest the appropriate self-care file to provide to the patient. A given algorithm may have a number of different self-care files (instructions), depending on the nature of the complaint. The specific structure and format to be used for self-care files is provided at the end of this description.

The following provides the recommended process for completing the self-care files on the work station:

1. Depress and hold down the mouse "click" at any point on the background of the screen. This will "show" your Root Menu. Without releasing the mouse "click" yet, scroll down the Root Menu to the New Window option and release the mouse.
2. Wait for a few seconds and a window will appear on the screen.
3. At the % prompt of this window, type in textedit& and hit the "return" key on the keyboard. Wait a few seconds, and the TEXTEDITOR window will appear.
4. Once the TEXTEDITOR appears, you are ready to begin entering the Self-Care file. Note that the TEXTEDITOR is a basic word-processing function included in the standard software options of the workstation. It operates much like "WORD" for MacIntosh. A complete description of the TextEdit tool for Sun Stations is provided at the end of this document.
5. At this point, simply type in the desired text The approved structure and format for the Self-Care files is provided in an example that can be found in Appendix D at the end of this description.
6. When completed, "click" on the "FILE" option in the upper left-hand corner of the textedit window. A pop-up window will appear (TEXT:STORE) in which you will provide the proper command to save and store the completed file.
7. In the "TEXT:STORE" window, move the mouse pointer to the upper line ("Directory"). Type in the correct directory to which you want this file to be stored. This will be:
/triage/home/<user>/self Enter this command, and note that the cursor moves to the next line "FILE:".

8. At the "FILE" line, type in the correct UNIX file name for the Self-Care file. The Official UNIX file names for these files can be found on the algorithm control sheet. For example, the file name for a self-care file "Adult Musculoskeletal back Pain" associated with the algorithm ADULT_BACK_PAIN would be as follows:
A097S01A.001

Entering this command will store the file in the "self" directory, identified with its associated algorithm.

Retrieving and Editing an Existing Algorithm

The Editor Program provides a number of functions to allow for the efficient editing of an algorithm. These editing functions include:

Retrieving an existing algorithm file
Editing algorithm text
a "COPY" function
a "PASTE" function
an "OPEN SPACE" function
a "CLOSE SPACE" function
a "DELETE" function Specific instructions for the use of each of these editing functions are provided in below.

Retrieving an existing algorithm

In order to retrieve an algorithm file for review or editing, a few simple steps are required, as follows:

Click on the "EDIT" option in the menu bar of the Editor window. A window will appear ("Select Algorithm File pop-up") from which you will select the desired algorithm (see FIG. 61).

In the "Directories" column of this window, locate the directory that stores the algorithm that you wish to review/edit.

Double-click on this directory name. This will change the "EDIT" window somewhat, to accommodate only the files stored in this directory.

In the "Files" column of this window, locate and "click" on the desired algorithm file name (or number). This will highlight the selection you desire.

Move the pointer down and "click" on the "OK" button in the lower left-hand corner of this window. This affirms the selection of the algorithm file that you have highlighted After a few seconds, the algorithm file will appear in the Editor window and is now retrieved and ready for review/editing.

Editing Algorithm Text

To review and/or edit any text that has been entered into the Editor, simply "click" on the desired algorithm node. The appropriate "Parameter" window will appear, with all the text that has been previously entered.

"Click" on the text field of this window that you wish to edit Move the mouse pointer to the location of the desired editing change and complete the editing process. In the Editor, editing is much like text editing in MacIntosh. You are able to "highlight" a letter, word, or group of words and then delete them by striking the "Backspace" key on the keyboard. Insert words or phrases by placing the mouse pointer at the desired location and entering the revision. Assuming the user has some familiarity with basic text editing, the functions here will be very familiar.

When completed with the editing of a node, simply move to the next node in the algorithm that you wish to edit The changes are automatically stored in the appropriate text field of each "Parameter" window. REMEMBER THAT THE EDITOR DOES NOT AUTOMATICALLY SAVE TEXT. YOU MUST FREQUENTLY SAVE YOUR REVISIONS (as previously described) SO THAT YOU DON'T LOSE YOUR WORK.

Using the "COPY" function

The Editor has a number of helpful editing functions for revising/altering the algorithm logic (placement of the nodes and linkages). Copying an individual node, or a group of nodes, is the first of these functions.

You can accomplish this function as follows:

In the Editor window, retrieve the algorithm file that you wish to edit (per instructions provided above).

When the algorithm "logic" appears in the window, "click" on the DRAW function of the window's menu bar. This will retrieve a small "DRAW" window that provides a number of editing options (see FIG. 64).

To copy a single node, "click" on the "Select Mode" option in this DRAW window. Then move the mouse pointer to the desired node to be copied.

"Click" on this node so that it is highlighted.

Move the mouse pointer back to the "DRAW" window. "Click" on the "COPY" option. The node, and all of its associated node data, is now stored in copy memory to be "Pasted" at another location in the algorithm (This process will be described in the next section).

To copy a group of nodes, "click" on the "Select Mode" option of the DRAW window. Move the mouse pointer to the upper left-hand corner of the "area" (group of nodes) that you wish to copy.

Depress and hold down the "click", moving the mouse downward and to the right slowly. Notice that you are "drawing a visible box" around the desired group of algorithm nodes.

Continue "drawing the box" until you have included inside the box the entire set of nodes you wish to copy.

When all nodes have been included within this "boxed" area, release the mouse. The area that you have chosen to copy will now be "highlighted".

Move the mouse pointer back to the "DRAW" window. "Click" on the "COPY" option. The group of nodes, and all of their associated node data, are now stored in copy memory to be "Pasted" at another location in the algorithm. (This process will be described in the next section).

Note that you can copy any number of nodes desired, as long as they "appear" in the Editor window. You cannot scroll downward (or upward) to capture an area to copy that is larger than the area of the Editor window. Please be aware that the software will automatically give the "copied" nodes new node numbers once they are "pasted" into the algorithm. This is a process that the user cannot control.

Using the "PASTE" Function

The Paste function of the Editor allows you to "paste" any node, or group of nodes, to another location within the same algorithm. This is often helpful to speed the creation of algorithm logic (boxes and linkages) and to eliminate the need to re-type the same (or similar) node data repeatedly in the process of algorithm creation. The process works as follows:

Once you have correctly "copied" a single node, or a group of nodes, they are "stored temporarily in copy memory.

Move to the desired location in the Editor window.

Move the mouse pointer back to the "DRAW" window and select the "PASTE" function.

Move the mouse pointer back to the Editor window to the location where you wish to paste the copied node(s).

Depress and hold down the mouse "click". Note that the outline of the node (or node area) that you have copied now appears on the screen.

Move the mouse in any desired direction (with the mouse "click" still depressed) to position the node/node area in the way that you wish.

When the desired location of the node/node area is determined, release the mouse "click" and the desired node/node area will appear on the screen. Note that the copying and pasting functions will only copy linkages that are entirely within the drawn area. As a result, remember to complete the process of linking these "new" nodes properly within the algorithm.

It is also important to note that only one "image" (node or group of nodes) can be stored in copy memory at one time. As a result, you must both copy and then paste the desired node(s) before attempting to copy another node or area.

Using the "OPEN SPACE" Function

In order to be able to revise an algorithm by adding new nodes (or by copying and pasting nodes into a new area of the algorithm), there must be an ability to "open up space" within the algorithm logic. This can be accomplished by using the "OPEN SPACE" editing function. This function is completed as follows:

Identify the location within an algorithm where you wish to "open an area" to include additional nodes. Make sure this area "appears" in the Editor window.

Move the mouse pointer to the "DRAW" window (if this window is no longer visible, "click" again on the DRAW option of the menu bar). It will re-appear.

"Click" on the "SELECT MODE" option. Then select the "OPEN SPACE" option on this same DRAW window.

Move the mouse pointer back to the Editor window. At the left-hand edge of the location where you wish to open space, depress and hold down the mouse "click". Note that a horizontal line appears across the Editor window at this spot.

With the mouse "click" still depressed, move the mouse downward until you have identified an area large enough for your purposes. The "box" that is formed on the Editor window from this process indicates the size of the area that you will open.

When you have opened enough space for the desired editing, release the mouse and the circumscribed area will "open up".

Note that any of the linkages that are affected by this opening of space will remain attached to their destination node, lengthening to accommodate the opened space. Any linkage that is "in the way" of your desired algorithm changes must be deleted before the changes are made. This process is described below in the section "Using the Delete Function".

Using the "CLOSE SPACE" Function

Occasionally, there is a need to "close space" in the algorithm logic. For sizeable "gaps" between nodes (vertically), this function can be used to narrow this distance. This function is completed as follows:

Identify the location within an algorithm where you wish to "close an area".

Make sure this location "appears" in the Editor window.

Move the mouse pointer to the "DRAW" window (if this window is no longer visible, "click" again on the DRAW option of the menu bar). It will re-appear.

"Click" on the "SELECT MODE" option. Then select the "CLOSE SPACE" option on this same DRAW window.

Move the mouse pointer back to the Editor window. At the left-hand edge of the location where you wish to close space, depress and hold down the mouse "click". Note that a horizontal line appears across the Editor window at this spot.

With the mouse "click" still depressed, move the mouse downward until you have identified an area large enough for your purposes. The "box" that is formed on the Editor window from this process indicates the size of the area that you will close. The area that you identify to "close" cannot touch any node. If it does (even partially), the closing function will not work.

When you have identified the space to be closed, release the mouse and the circumscribed area will "close".

Note that any of the linkages that are affected by this opening of space will remain attached to their destination node, shortening to accommodate the closed space.

Please note that the proper functioning of an algorithm in the Nursetool does NOT require any specified distance between nodes in the algorithm editor.

Closing space is thus more of a cosmetic change in the appearance of the algorithm and, as such, is not necessary for the proper functioning of the algorithm in the Nursetool.

Using the "DELETE" Function

The final "editing" function of the Editor is the "DELETE" function. As implied, this function is used to remove (or delete) a node, group of nodes, or a linkage between nodes. This is often required in the process of editing an algorithm.

You Can Accomplish this Function as Follows

To delete a single node, "click" on the desired node to be deleted. The node will be highlighted.

Move the mouse pointer back to the "DRAW" window. "Click" on the "DELETE" option. The node, and all of its associated node data is now deleted.

To delete a group of nodes, "click" on the "Select Mode" option of the DRAW window. Move the mouse pointer to the upper left-hand corner of the "area" (group of nodes) that you wish to delete.

Depress and hold down the "click", moving the mouse downward and to the right slowly. Notice that you are "drawing a visible box" around the desired group of algorithm nodes.

Continue "drawing the box" until you have included inside the box the entire set of nodes you wish to delete.

When all desired nodes have been included within this "boxed" area, release the mouse. The area that you have chosen to copy will now be "highlighted".

Move the mouse pointer back to the "DRAW" window. "Click" on the "DELETE" option. The group of nodes, and all of their associated node data, are now deleted.

Note that you can delete any number of nodes desired, as long as they "appear" in the Editor window. You cannot scroll downward (or upward) to capture an area to delete that is larger than the area of the Editor window.

To delete a single linkage, "click" on the desired linkage to be deleted The linkage will become highlighted.

Move the mouse pointer back to the "DRAW" window. "Click" on the "DELETE" option. The linkage is now deleted.

Retrieving and Editing Cover Sheets and Self-Care Files

The Cover Sheets and Self-Care files associated with algorithms have been created on the workstation (in UNDO but outside of the Editor program Thus, a different method of retrieval and editing will have to be used for these files. The Retrieval and Editing of the Cover Sheet and Self-Care files is accomplished in the TEXTEDIT tool of the Workstation (described above). The process is as follows:

1. Depress and hold down the mouse "click" at any point on the background of the screen. This will "show" your Root Menu. Without releasing the mouse "click" yet, scroll down the Root Menu to the New Window option and release the mouse.

2. Wait for a few seconds and a window will appear on the screen.

3. At the % prompt of this window, type in textedit& and hit the "return" key on the keyboard. Wait a few seconds, and the TEXTEDITOR window will appear.

4. Once the TEXTEDITOR appears, you are ready to begin the retrieval and editing of the desired file. Note that the TEXTEDITOR is a basic word-processing function included in the standard software options of the workstation. It operates much like "WORD" for MacIntosh. A complete description of the TextEdit tool for Sun Stations is provided at the end of this description.

5. To retrieve the desired file, click on the "file" option of the Text Editor window. A pop-up window "TEXT:LOAD" will appear. On the top line of this window ("Directory"), type in the correct name of the directory that houses the file that you wish to edit.

For Cover Sheets, this is the cover directory. Type on this line:
/triage/home/<user>/cover
and enter this command. Note that the cursor moves to the "File" line. For Self-Care files, this is the self directory. Type on this line:
/triage/home/<user>/self
and enter this command. Note that the cursor moves to the "File" line.

6. At the "FILE" line, type in the correct file name for the desired. The Official file names for these files can be found on the algorithm control sheet.

For example, the file name for a self-care file "Adult Musculoskeletal back Pain" associated with the algorithm ADULT_BACK_PAIN would be as follows:
A097S01A.001

Entering this command will retrieve the file from the "self" directory into the TEXTEDIT window. The file is now ready for editing.

7. Edit the desired file using the instructions for the TEXTEDIT tool, located at the end of this document.

8. When the editing has been completed, "click" on the "file" button of the TEXTEDIT window. This "saves" to newly-edited file. At this point, if you wish to edit another Cover Sheet or Self-Care file, simply "click" again on the "File" option of the TEXTEDIT window. The "TEXT:LOAD window will re-appear. Repeat steps 5–8 (above) to continue the editing process.

Recommended terminology:

"Message to Patient" fields

The following provides a listing of the "approved" terminology to use in entering the "message to patient" fields in the various specific types of ACTION AND ENDPOINT recommendation nodes. For all of the "message to patient" statements, the idea is to provide a concise, accurate suggestion to be used by the nurse upon providing the algorithm recommendation to the patient

ENDPOINT NODES

1. ACTIVATE EMERGENCY PROCEDURES

Message to Patient
 Because <symptom pattern>, we think that it would be best if the emergency ambulance comes to help get <you, your child> to the hospital quickly. Please stay on the phone and well make the necessary arrangements for you.

2. SPEAK TO IAS PROVIDER

Message to Patient:
 Because <symptom pattern>, we think it would be best if you spoke with our physician. If you'll stay on the phone, we'll connect you as quickly as possible.

3. URGENTCARE

Message to Patient:
 Because <symptom pattern>, we recommend that you <see, have the child see>a health care provider as soon as you can.

4. SPEAK TO PROVIDER—SORTING-NOW

Message to Patient
 Because <symptom pattern>, we'd like to have you talk to a provider NOW to help determine the appropriate next steps for you to take.

5. SPEAK TO PROVIDER—SORTING-LATER

Message to Patient
 Because <symptom pattern>, we'd like to have you talk to a provider in the next 2–4 hours. The provider can help determine the appropriate next steps for you to take.

6. SPEAK TO PROVIDER—TREATMENT

Message to Patient
 Because <symptom pattern>, we'd like to have you talk to a provider in the next 2–4 hours. The provider can help determine the appropriate next steps for you to take.

7. EARLY ILLNESS APPOINTMENT

Message to Patient:
 Because <symptom pattern>, we recommend that you make an appointment to see a provider as soon as possible.

8. ROUTINE ILLNESS APPOINTMENT

Message to Patient
 Because <symptom pattern>, we recommend that you make an appointment to see a provider in the near future (next 2 weeks).

9. ACCESS SELF-CARE INSTRUCTIONS

Message to Patient
 Your answers to our questions indicate that it is highly unlikely that <your, the child's >< specific complaint, symptoms> would benefit from an appointment with a from an appointment with a provider. We'd like to suggest home care instructions. Would that be alright with you?

ACTION NODES

1. SPEAK TO IAS PROVIDER

Message to Patient:
 Because <symptom pattern>, we think it would be best if you spoke with our physician. If you'll stay on the phone, we'll connect you as quickly as possible.

2. SPEAK TO PROVIDER—SORTING-NOW

Message to Patient:
 Because <symptom pattern>, we'd like to have you talk to a provider NOW to help determine the appropriate next steps for you to take.

3. SPEAK TO PROVIDER—SORTING-LATER

Message to Patient
 Because <symptom pattern>, we'd like to have you talk to a provider in the next 2–4 hours. The provider can help determine the appropriate next steps for you to take.

4. SPEAK TO PROVIDER—TREATMENT

Message to Patient:
 Because <symptom pattern>, we'd like to have you talk to a provider in the next 2–4 hours. The provider can help determine the appropriate next steps for you to take.

5. EARLY ILLNESS APPOINTMENT

Message to Patient:
 Because <symptom pattern>, we recommend that you make an appointment to see a provider as soon as possible.

6. ROUTINE ILLNESS APPOINTMENT

Message to Patient
 Because <symptom pattern>, we recommend that you make an appointment to see a provider in the near future (next 2 weeks).

7. ACCESS SELF-CARE INSTRUCTIONS

Message to Patient
 Your answers to our questions indicate that it is highly unlikely that <your, the child's >< specific complaint, symptoms > would benefit from an appointment with a provider. We'd like to suggest home care instructions. Would that be alright with you?

It should now be readily apparent to those skilled in the art that a novel medical network management system and process capable of achieving the stated objects of the invention has been provided. The medical network management system and process system is based on understanding and managing the process of care, in an integrated manner, from the onset of patient perception of possible needs. The medical network management system and process allows beneficiaries to obtain appropriate care, at the appropriate time, from an appropriate provider. The medical network management system and process effectively reduces utilization and costs, while increasing user satisfaction and overall quality of care. The medical network management system and process uses unique information systems to help guide patients through and manage the process of care, thereby assuring quality health care.

It should further be apparent to those skilled in the art that various changes in form and details of the invention as shown and described may be made. It is intended that such changes be included within the spirit and scope of the claims appended hereto.

What is claimed is:

1. An article of manufacture for use with a data processing system, comprising a storage medium having stored therein a medical provider information stored program, and a medical provider database describing clinical services or procedures available from each provider by clinical codes or procedure codes in said data processing system, said data processing system being configured by said medical provider information stored program when executed by said data processing system to use said clinical codes or said procedural codes to identify a medical provider from said medical provider database for providing a specific medical service to a patient.

2. The article of manufacture as recited in claim 1 in which a patient assessment stored program is additionally provided in said storage medium, said patient assessment stored program including a plurality of patient complaint based branched chain logic algorithms, each of said plurality of patient complaint based branched chain logic algorithms being configured to present a series of questions answerable by "yes" or "no" when said patient assessment stored program is executed by said data processing system, each of the answers to said questions being used by said data processing system when said patient assessment stored program is executed by said data processing system to make a categorization of the patient as either:

(a) having a sufficiently low post-test probability of a specific illness or injury under consideration so as to eliminate possible need for further investigation, medical care, or other health care, for the specific illness or injury under consideration; or (b) not having a sufficiently low post-test probability of the specific illness or injury under consideration so as to eliminate possible need for further investigation, medical care, or other health care, for the specific illness or injury under consideration;

the answers further being used with the categorization to recommend an appropriate intervention for the specific illness or injury under consideration, said data processing system further being configured by said patient assessment stored program and said medical provider information stored program when executed by said data processing system to link said patient assessment stored program to said medical provider information stored program and said medical provider database with said clinical codes or said procedure codes.

3. The article of manufacture as recited in claim 2 in which said patient assessment stored program is configured to make a medical care recommendation and said medical care provider information stored program is configured to make a medical provider selection for the patient based on the medical care recommendation using the clinical codes when said patient assessment stored program and said medical provider stored program are executed on said data processing system.

4. The article of manufacture as recited in claim 2 in which said medical provider information stored program includes software that selects a medical provider for the patient, said data processing system further being configured by said medical provider information stored program when executed by said data processing system to make a medical provider selection for the patient from said medical provider database based on said clinical codes and the patient information.

5. The article of manufacture as recited in claim 4 in which said medical provider information stored program further includes software that refers the patient to the medical provider.

6. An article of manufacture for use with a data processing system, comprising a storage medium having stored therein a medical provider information stored program, said data processing system including a medical care provider database describing providers and clinical services, procedures, or other health care available from each provider by clinical codes or procedure codes stored in said data processing system, wherein providers include physicians, clinics, hospitals, therapists, dentists, and nurses, and providers are described by stored background information in said memory, practice information including at least one of location, billing information, and language spoken, said data processing system being configured by said medical provider information stored program when executed by said data processing system to use at least one of said clinical codes or said procedural codes to identify a medical provider from said medical provider database for providing a specific medical service to a patient, wherein said clinical codes or said procedural codes are based on at least one of the International Classification of Diseases (ICD), the Physician's Current Procedural Terminology (CPT), Current Dental Terminology (CDT), and the Diagnostic and Statistical Manual of Mental Disorders (DSM), and wherein said clinical or procedural codes prospectively describe the availability of said clinical services from each provider or provider location.

7. The article of manufacture as recited in claim 6 in which a patient assessment stored program is additionally provided in said storage medium, said patient assessment stored program including a plurality of patient complaint based branched chain logic algorithms, each of said plurality of patient complaint based branched chain logic algorithms being configured to present a series of questions answerable with "yes" or "no" when said patient assessment stored program is executed by said data processing system, each of the answers to said questions being used by said data processing system when said patient assessment stored program is executed by said data processing system to make a categorization of the patient as either:

(a) having a sufficiently low post-test probability of a specific illness, injury, condition, or etiology under consideration so as to clinically eliminate possible need for further investigation, medical care, or other health care, for the specific illness, injury, condition, or etiology under consideration; or (b) not having a sufficiently low post-test probability of the specific illness, injury, condition, or etiology under consideration so as to clinically eliminate possible need for further investigation, medical care, or other health care, for the specific illness, injury, condition, or etiology under consideration;

the answers further being used with the categorization to identify a set of appropriate interventions for injuries and illnesses which cannot be clinically eliminated, wherein an appropriate intervention in the set of appropriate interventions has at least one characteristic selected from the group consisting of level of intervention, timing of the intervention, place of intervention, nature of intervention, type of provider, said data processing system further being configured by said patient assessment stored program and said medical provider information stored program when executed by said data processing system to link said patient assessment stored program to said medical provider information stored program and said medical provider data base with said clinical codes or said procedure codes, said data processing system further being configured by said medical provider information stored program to make a medical provider or medical provider location selection from said medical provider database based on said clinical codes and the patient information.

* * * * *